US008137923B2

(12) United States Patent
Busfield et al.

(10) Patent No.: US 8,137,923 B2
(45) Date of Patent: Mar. 20, 2012

(54) GLYCOPROTEIN VI AND USES THEREOF

(75) Inventors: Samantha J. Busfield, Cambridge, MA (US); Jean-Luc Villeval, Needham, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 12/690,710

(22) Filed: Jan. 20, 2010

(65) Prior Publication Data

US 2010/0261200 A1 Oct. 14, 2010

Related U.S. Application Data

(60) Continuation of application No. 11/447,460, filed on Jun. 6, 2006, now abandoned, which is a division of application No. 09/503,387, filed on Feb. 14, 2000, now Pat. No. 7,291,714, which is a continuation-in-part of application No. 09/454,824, filed on Dec. 6, 1999, now abandoned, which is a continuation-in-part of application No. 09/345,468, filed on Jun. 30, 1999, now Pat. No. 6,245,527.

(51) Int. Cl.
*G01N 33/53* (2006.01)
*C07K 16/18* (2006.01)
*C07K 16/28* (2006.01)
*C12P 21/08* (2006.01)

(52) U.S. Cl. .................. 435/7.1; 530/387.1; 530/387.3; 530/388.1; 530/388.22; 530/389.1; 530/391.3

(58) Field of Classification Search ........................ None
See application file for complete search history.

(56) References Cited

U.S. PATENT DOCUMENTS

| | | | |
|---|---|---|---|
| 4,474,893 A | 10/1984 | Reading | |
| 4,676,980 A | 6/1987 | Segal et al. | |
| 4,714,681 A | 12/1987 | Reading | |
| 4,816,397 A | 3/1989 | Boss et al. | |
| 4,816,567 A | 3/1989 | Cabilly et al. | |
| 4,925,648 A | 5/1990 | Hansen et al. | |
| 5,223,409 A | 6/1993 | Ladner et al. | |
| 5,225,539 A | 7/1993 | Winter | |
| 5,272,057 A | 12/1993 | Smulson et al. | |
| 5,403,484 A | 4/1995 | Ladner et al. | |
| 5,427,908 A | 6/1995 | Dower et al. | |
| 5,459,039 A | 10/1995 | Modrich et al. | |
| 5,516,637 A | 5/1996 | Huang et al. | |
| 5,545,806 A | 8/1996 | Lonberg et al. | |
| 5,569,825 A | 10/1996 | Lonberg et al. | |
| 5,571,698 A | 11/1996 | Ladner et al. | |
| 5,573,920 A | 11/1996 | Randle | |
| 5,580,717 A | 12/1996 | Dower et al. | |
| 5,585,089 A | 12/1996 | Queen et al. | |
| 5,601,819 A | 2/1997 | Wong et al. | |
| 5,625,126 A | 4/1997 | Lonberg et al. | |
| 5,633,425 A | 5/1997 | Lonberg et al. | |
| 5,658,727 A | 8/1997 | Barbas et al. | |
| 5,661,016 A | 8/1997 | Lonberg et al. | |
| 5,698,426 A | 12/1997 | Huse | |
| 5,733,743 A | 3/1998 | Johnson et al. | |
| 5,780,225 A | 7/1998 | Wigler et al. | |
| 5,821,047 A | 10/1998 | Garrard et al. | |
| 5,854,005 A | 12/1998 | Coller | |
| 5,874,289 A | 2/1999 | Liu et al. | |
| 5,877,289 A | 3/1999 | Thorpe et al. | |
| 5,969,108 A | 10/1999 | McCafferty et al. | |
| 5,976,532 A | 11/1999 | Coller et al. | |
| 6,245,527 B1* | 6/2001 | Busfield et al. | 435/69.1 |
| 6,383,779 B1 | 5/2002 | Busfield et al. | |
| 6,989,144 B1* | 1/2006 | Busfield et al. | 424/130.1 |
| 7,101,549 B2* | 9/2006 | Gill et al. | 424/130.1 |
| 7,291,714 B1* | 11/2007 | Busfield et al. | 530/387.1 |
| 7,597,888 B2* | 10/2009 | Gill et al. | 424/130.1 |
| 2004/0001826 A1* | 1/2004 | Gill et al. | 424/143.1 |
| 2004/0253236 A1* | 12/2004 | Gill et al. | 424/143.1 |
| 2006/0216291 A1* | 9/2006 | Busfield et al. | 424/144.1 |
| 2008/0050380 A1* | 2/2008 | Gill et al. | 424/139.1 |

FOREIGN PATENT DOCUMENTS

| | | |
|---|---|---|
| EP | 0 125 023 A1 | 11/1984 |
| EP | 0 171 496 A2 | 2/1986 |
| EP | 0 173 494 A2 | 3/1986 |
| EP | 0 184 187 A2 | 6/1986 |
| WO | WO-86/01533 A1 | 3/1986 |
| WO | WO-87/02671 A1 | 5/1987 |
| WO | WO-90/02809 A1 | 3/1990 |
| WO | WO-91/00360 A1 | 1/1991 |
| WO | WO-91/10737 A1 | 7/1991 |
| WO | WO-91/17271 A1 | 11/1991 |
| WO | WO-92/01047 A1 | 1/1992 |
| WO | WO-92/05793 A1 | 4/1992 |
| WO | WO-92/08802 A1 | 5/1992 |
| WO | WO-92/09690 A2 | 6/1992 |
| WO | WO-92/15679 A1 | 9/1992 |
| WO | WO-92/18619 A1 | 10/1992 |
| WO | WO-92/20791 A1 | 11/1992 |
| WO | WO-92/22324 A1 | 12/1992 |

(Continued)

OTHER PUBLICATIONS

Adams MD et al., "Initial assessment of human gene diversity and expression patterns based upon 83 million nucleotides of cDNA sequence", Nature. 377(6547 Suppl):3-174 (Sep. 28, 1995).

(Continued)

*Primary Examiner* — Phuong Huynh
(74) *Attorney, Agent, or Firm* — Foley Hoag LLP

(57) ABSTRACT

The invention provides isolated nucleic acid molecules and polypeptide molecules that encode glycoprotein VI, a platelet membrane glycoprotein that is involved platelet-collagen interactions. The invention also provides antisense nucleic acid molecules, expression vectors containing the nucleic acid molecules of the invention, host cells into which the expression vectors have been introduced, and non-human transgenic animals in which a nucleic acid molecule of the invention has been introduced or disrupted. The invention still further provides isolated polypeptides, fusion polypeptides, antigenic peptides and antibodies. Diagnostic, screening and therapeutic methods utilizing compositions of the invention are also provided.

11 Claims, 27 Drawing Sheets

FOREIGN PATENT DOCUMENTS

| | | |
|---|---|---|
| WO | WO-93/01288 A1 | 1/1993 |
| WO | WO-93/11236 A1 | 6/1993 |
| WO | WO-93/17715 A1 | 9/1993 |
| WO | WO-95/11259 A1 | 4/1995 |
| WO | WO-95/15982 A2 | 6/1995 |
| WO | WO-95/20401 A1 | 8/1995 |
| WO | WO-97/13844 A1 | 4/1997 |
| WO | WO-99/11662 A1 | 3/1999 |
| WO | WO-00/68377 A1 | 11/2000 |
| WO | WO-2005/111083 A2 | 11/2005 |

OTHER PUBLICATIONS

Altschul SF et al., "Basic local alignment search tool", J Mol Biol. 215(3):403-10 (Oct. 5, 1990).
Altschul SF et al., "Gapped BLAST and PSI-BLAST: a new generation of protein database search programs", Nucleic Acids Res. 25(17)3389-402 (Sep. 1, 1997).
Ames et al., "Conversion of murine Fabs isolated from a combinatorial phage display library to full length immunoglobulins", J. Immunol. Methods 184:177-186 (1995).
Arai M et al., "Platelets with 10% of the normal amount of glycoprotein VI have an impaired response to collagen that results in a mild bleeding tendency", Br J Haematol. 89(1):124-30 (Jan. 1995).
Arnon et al., "Monoclonal antibodies for immunotargeting of drugs in cancer therapy", in: Monoclonal Antibodies and Cancer Therapy, Reisfeld et al., eds., Alan R. Liss, Inc., pp. 243-256 (1985).
Asselin J et al., "Monomeric (glycine-proline-hydroxyproline)10 repeat sequence is a partial agonist of the platelet collagen receptor glycoprotein VI", Biochem J. 339 (Pt 2):413-8 (Apr. 15, 1999).
Ausubel et al., (eds.), in: Current Protocols in Molecular Biology, Green Publishing Associates, Inc. and John Wiley & Sons, Inc., NY, p. 6.3.1-6.3.6 and 2.10.3 (1989).
Baldwin et al., (eds.), "Analysis, results and future prospective of the therapeutic use of radiolabeled antibody in cancer therapy", in: Monoclonal Antibodies for Cancer Detection and Therapy, Academic Press, pp. 303-316 (1985).
Barany F, "Genetic disease detection and DNA amplification using cloned thermostable ligase", Proc Natl Acad Sci U S A. 88(1):189-93 (Jan. 1, 1991).
Barnes MJ et al., "The collagen-platelet interaction", Curr Opin Hematol. 5(5):314-20 (Sep. 1998).
Beidler et al., "Cloning and high level expression of a chimeric antibody with specificity for human carcinoembryonic antigen", J. Immunol. 141:4053-4060 (1988).
Better et al., "*Escherichia coli* secretion of an active chimeric antibody fragmen", Science 240:1041-1043 (1988).
Briddon SJ et al., "Evidence for the involvement of p59fyn and p53/56lyn in collagen receptor signalling in human platelets", Biochem J. 338 (Pt 1):203-9 (Feb. 15, 1999).
Brinkmann et al., "Phage display of disulfide-stabllized Fv fragments", J. Immunol. Meth. 182:41-50 (1995).
Burton et al, "Human antibodies from combinatorial libraries", Adv. Immunol. 57:191-280 (1994).
Carlsson LE et al., "Heparin-induced thrombocytopenia: new insights into the impact of the FcyRIIa-R-H131 polymorphism", Blood. 92(5):1526-31 (Sep. 1, 1998).
Chiang TM et al., "Isolation and purification of collagen alpha 1(l) receptor from human platelet membrane", J Biol Chem. 257(13):7581-6 (Jul. 10, 1982).
Chiang TM et al., "Cloning, characterization, and functional studies of a nonintegrin platelet receptor for type I collagen", J Clin Invest. 100(3):514-521 (Aug. 1997).
Clemetson JM et al., "The Platelet Collagen Receptor Glycoprotein VI Is a Member of the Immunoglobulin Superfamily Closely Related to FcalphaR and the Natural Killer Receptors", J Biol Chem. 274(41):29019-29024 (Oct. 8, 1999).
Clemetson KJ et al., "Characterization of the platelet membrane glycoprotein abnormalities in Bernard-Soulier syndrome and comparison with normal by surface-labeling techniques and high-resolution two-dimensional gel electrophoresis", J Clin Invest. 70(2):304-11 (Aug. 1982).
Clemetson KJ, "Platelet activation: signal transduction via membrane receptors", Thromb Haemost. 74(1):111-6 (Jul. 1995).

Cole et al., "The EBV-hybridoma technique and its application to human lung cancer", in: Monoclonal Antibodies and Cancer Therapy, Alan R. Liss, Inc., pp. 77-96 (1985).
Coligan et al., (eds.), Current Protocols in Immunology, John Wiley and Sons, New York, p. 2.5.1-2.5.11 (1992).
Coller et al., "A new murine monoclonal antibody reports an activation-dependent change in the conformation and/or microenvironment of the platelet glycoprotein IIb/IIIa complex", J Clin Invest. 76(1):101-8 (1985).
Cotton RG, "Current methods of mutation detection", Mutat Res. 285(1):125-44 (Jan. 1993).
Cotton RG et al., "Reactivity of cytosine and thymine in single-base-pair mismatches with hydroxylamine and osmium tetroxide and its application to the study of mutations", Proc Natl Acad Sci U S A. 85(12):4397-401 (Jun. 1988).
Cronin MT et al., "Cystic fibrosis mutation detection by hybridization to light-generated DNA probe arrays", Hum Mutat. 7(3):244-55 (1996).
Ezumi et al., "Molecular cloning, genomic structure, chromosomal localization, and alternative splice forms of the platelet collagen receptor glycoprotein VI", Biochem Biophys Res Commun 277(1):27-36 (2000).
Ezumi Y et al., "Physical and functional association of the Src family kinases Fyn and Lyn with the collagen receptor glycoprotein VI-Fc receptor gamma chain complex on human platelets", J Exp Med. 188(2):267-76 (Jul. 20, 1998).
Fan et al., "Structure of the inhibitory receptor for human natural killer cells resembles haematopoietic receptors" Nature, 389(6646):96-100 (1987).
Fuchs et al., "Targeting recombinant antibodies to the surface of *Escherichia coli*: fusion to a peptidoglycan associated lipoprotein", Bio/Technology 9:1369-1372 (1991).
Gibbins JM et al., "Glycoprotein VI is the collagen receptor in platelets which underlies tyrosine phosphorylation of the Fc receptor gamma-chain", FEBS Lett. 413(2):255-9 (Aug. 18, 1997).
Gibbins JM et al., "The p85 subunit of phosphatidylinositol 3-kinase associates with the Fc receptor gamma-chain and linker for activitor of T cells (LAT) in platelets stimulated by collagen and convulxin", J Biol Chem. 273(51):34437-43 (Dec. 18, 1998).
Gibbs RA et al., "Detection of single DNA base differences by competitive oligonucleotide priming", Nucleic Acids Res. 17(7):2437-48 (Apr. 11, 1989).
Goto et al., "Involvement of glycoprotein VI in platelet thrombus formation on both collagen and von Willebrand factor surfaces under flow conditions," Circulation 106(2):266-272 (Jul. 9, 2002).
Griffiths et al., "Human anti-self antibodies with high specificity from phage display libraries", EMBO J. 12:725-734 (1993).
Gruner et al, "Anti-glycoprotein VI treatment severely compromises hemostasis in mice with reduced alpha2beta1 levels or concomitant aspirin therapy," Circulation 110(18):2946-2951 (Nov. 2, 2004).
Handa M et al., "Platelet unresponsiveness to collagen: involvement of glycoprotein la-IIa (alpha 2 beta 1 integrin) deficiency associated with a myeloproliferative disorder", Thromb Haemost. 73(3):521-8 (Mar. 1995).
Hanson et al., "Pharmacologic modification of acute vascular graft thrombosis", Scan. Electron Microsc. II:773-779 (1982).
Harlow et al, Antibodies a Laboratory Manual, Cold Spring harbor laboratory publication, Cold Spring Harbor, NY, pp. 321-358 (1988).
Hay et al., "Bacteriophage cloning and *Escherichia coli* expression of a human IgM Fab", Hum. Antibod. Hybridomas 3:81-85 (1992).
Hayashi K. "PCR-SSCP: a method for detection of mutations", Genet Anal Tech Appl. 9(3):73-9 (Jun. 1992).
Heemskerk JW et al., "Function of glycoprotein VI and integrin alpha2beta1 in the procoagulant response of single, collagen-adherent platelets", Thromb Haemost. 81(5):782-92 (May 1999).
Hellstrom et al., "Antibodies for drug delivery", in: Controlled Drug Delivery, 2.sup.nd ed., Robinson et al., eds., Marcel Dekker, Inc., pp. 623-653 (1987).
Horton (ed.), "Preclinical development of c7E3 Fab; a mouse/human chimeric monoclonal antibody fragment that inhibits platelet function by blockade of GpIIb/IIIa receptors with observations on the immunogenicity of c7E3 Fab in humans", in: Adhesion Receptors as Therapeutic Targets, Chapter 15 by Jordan et al., CRC Press, London, England (1995).
Hsu IC et al., "Detection of DNA point mutations with DNA mismatch repair enzymes", Carcinogenesis. 15(8):1657-62 (Aug. 1994).
Huse et al., "Generation of a large combinatorial library of the immunoglobulin repertoire in phage lambda", Science 246:1275-1281 (1989).
Ichinohe T et al., "Collagen-stimulated activation of SyK but not c-Src is severely compromised in human platelets lacking membrane glycoprotein VI", J Biol Chem. 272(1):63-8 (Jan. 3, 1997).
Ichinohe T et al., "Cyclic AMP-insensitive activation of c-Src and Syk protein-tyrosine kinases through platelet membrane glycoprotein VI", J Biol Chem. 272(47):28029-36 (Nov. 24, 1995).
Inoue K et al., "Signal transduction pathways mediated by glycoprotein Ia/IIa in human platelets: comparison with those of glycoprotein VI", Biochem Biophys Res Commun. 256(1):114-20 (Mar. 5, 1999).
Ishibashi T et al, "Purification of p62, a putative platelet collagen receptor, and its functional significance in collagen-induced platelet aggregation." XIVth Congress of the International Society on Thrombosis and Haemostasis, New York. Thrombosis and Haemostasis. Abstract No. 1638 (Jul. 1993).
Ishibashi T et al, "Functional significance of platelet membrane glycoprotein p62 (GP VI), a putative collagen receptor." Int J Hematol. 62(2):107-15 (Aug. 1995).
Jandrot-Perrus M et al., "Adhesion and activation of human platelets induced by convulxin involve glycoprotein VI and integrin alpha2beta1", J Biol Chem. 272(43):27035-41 (Oct. 24, 1997).
Jandrot-Perrus et al., "Cloning, characterization, and functional studies of human and mouse glycoprotein VI: a platelet-specific collagen receptor from the immunoglobulin superfamily", Blood 96(5): 1798-1807 (2000).
Janeway et al., eds., Immunobiology: The Immune System in Health and Disease, 4.sup.th Ed., Current Biology Publications, Elsevier Science, London, UK, p. 87 (1999).
Jespers et al., "Guiding the selection of human antibodies from phage display repertoires to a single epitope of an antigen", Bio/Technology 12:899-903 (1994).
Jones et al., "Replacing the complementarity-determining regions in a human antibody with those from a mouse", Nature 321:552-525 (1986).
Karlin S et al, "Applications and statistics for multiple high-scoring segments in molecular sequences", Proc Natl Acad Sci U S A. 90(12):5873-7 (Jun. 15, 1993).
Karlin S, et al, "Methods for assessing the statistical significance of molecular sequence features by using general scoring schemes", Proc Natl Acad Sci U S A. 87(6):2264-8 (Mar. 1990).
Keen J et al., "Rapid detection of single base mismatches as heteroduplexes on Hydrolink gels", Trends Genet. 7(1):5 (Jan. 1991).
Kehrel B et al., "Glycoprotein VI is a major collagen receptor for platelet activation: it recognizes the platelet-activating quaternary structure of collagen, whereas CD36, glycoprotein IIb/IIIa, and von Willebrand factor do not", Blood. 91(2):491-9 (Jan. 15, 1998).
Kettleborough et al., "Isolation of tumor cell-specific single-chain Fv from immunized mice using phage-antibody libraries and the reconstruction of whole antibodies from these antibody fragments", Eur. J. Immunol. 24:952-958 (1994).
Knight CG et al., "Collagen-platelet interaction: Gly-Pro-Hyp is uniquely specific for platelet Gp VI and mediates platelet activation by collagen", Cardiovasc Res. 41(2):450-7 (Feb. 1999).
Kohler et al, "Continuous cultures of fused cells secreting antibody of predefined specificity", Nature 256:495-497 (1975).
Kostelny et al., "Formation of a bispecific antibody by the use of leucine zippers", J. Immunol. 148:1547-1553 (1992).
Kotite NJ et al, "Specific adsorption of a platelet membrane glycoprotein by human insoluble collagen", J Biol Chem. 261(18):8342-7 (Jun. 25, 1986).
Kozal MJ et al., "Extensive polymorphisms observed in HIV-1 Clade B protease gene using high-density oligonucleotide arrays", Nat Med. 2(7):753-9 (Jul. 1996).
Kuby et al, Immunology, Second edition, pp. 86-96 (1994).

Lagrue AH et al., "Phosphatidylinositol 3'-kinase and tyrosine-phosphatase activation positively modulate Convulxin-induced platelet activation. Comparison with collagen", FEBS Lett. 448(1):95-100 (Apr. 1, 1999).
Lefkovits et al., "Platelet glycoprotein IIb/IIIa receptors in cardiovascular medicine." N Engl J Med. 332(23):1553-9 (1995).
Liu et al., "Chimeric mouse-human IgG1 antibody that can mediate lysis of cancer cells", Proc. Natl. Acad. Sci. USA 84:3439-3443 (1987).
Liu et al., "Production of a mouse-human chimeric monoclonal antibody to CD20 with potent Fc-dependent biologic activity", J. Immunol. 139:3521-3526 (1987).
Lonberg et al, "Human antibodies from transgenic mice", Intern. Rev. Immunol. 13:65-93 (1995).
Loscalzo and Schaefer (eds.), Von Willebrand Factor, in: Thrombosis and Hemorrhage, 2.sup.nd ed., Chapter 16 by Ruggeri et al., Williams & Wilkins, Baltimore, MD, pp. 337-364 (1998).
Maliszewski CR et al., "Expression cloning of a human Fc receptor for IgA", J Exp Med. 172(6):1665-72 (Dec. 1, 1990).
Martin M et al., "Colon-cancer cell variants producing regressive tumors in syngeneic rats, unlike variants yielding progressive tumors, attach to interstitial collagens through integrin alpha2beta1", Int J Cancer. 65(6):796-804 (Mar. 15, 1996).
Miura et al., "Cloning and expression of platelet-specific collagen receptor glycoprotein VI", Thromb Res.98(4):301-9 (2000).
Moroi M et al., "A patient with platelets deficient in glycoprotein VI that lack both collagen-induced aggregation and adhesion", J Clin Invest. 84(5):1440-5 (Nov. 1989).
Moroi M et al, "Analysis of platelet adhesion to a collagen-coated surface under flow conditions: the involvement of glycoprotein VI in the platelet adhesion" Blood. 88(6):2081-92 (Sep. 15, 1996).
Moroi M et al, "Platelet receptors for collagen", Thromb Haemost. 78(1):439-44 (Jul. 1997).
Morrison, "Transfectomas provide novel chimeric antibodies", Science 229:1202-1207 (1985).
Moshfegh K et al., "Association of two silent polymorphisms of platelet glycoprotein Ia/IIa receptor with risk of myocardial infarction: a case-control study", Lancet. 353(9150):351-4 (Jan. 30, 1999).
Mullinax et al., "Expression of a heterodimeric Fab antibody protein in one cloning step", Biotechniques 12:864-869 (1992).
Myers RM et al., "Detection of single base substitutions by ribonuclease cleavage at mismatches in RNA:DNA duplexes", Science. 230(4731):1242-6 (Dec. 13, 1985).
Nakamura T et al., "Platelet adhesion to native type I collagen fibrils. Role of GPVI in divalent cation-dependent and -independent adhesion and thromboxane A2 generation", J Biol Chem. 273(8):4338-44 (Feb. 20, 1998).
Ngo et al, "The Protein Folding Problem and Tertiary Structure Prediction," pp. 492-495 (1994).
Nielsen H et al., "Identification of prokaryotic and eukaryotic signal peptides and prediction of their cleavage sites", Protein Eng. 10(1):1-6 (Jan. 1997).
Nieswandt et al., "Expression and function of the mouse collagen receptor glycoprotein VI is strictly dependent on its association with the FcRgamma chain," J Biol Chem 275(31):23998-24002 (Aug. 4, 2000).
Nishimura et al., "Recombinant human-mouse chimeric monoclonal antibody specific for common acute lymphocytic leukemia antigen", Cancer Res. 47:999-1005 (1987).
Oi et al., "Chimeric Antibodies", Bio/Techniques 4:214-221 (1986).
Orita M et al., "Detection of polymorphisms of human DNA by gel electrophoresis as single-strand conformation polymorphisms", Proc Natl Acad Sci U S A. 86(8):2766-70 (Apr. 1989).
Pearson WR et al, "Improved tools for biological sequence comparison", Proc Natl Acad Sci U S A. 85(8):2444-8 (Apr. 1988).
Persic et al., "An integrated vector system for the eukaryotic expression of antibodies or their fragments after selection from phage display libraries", Gene 187:9-18 (1997).
Pfam: http://pfam.wustl.edu Accession No. PF00047 "Immunoglobulin domain" (Bateman A and Sonnhammer ELL) (1995).
Phillips DR et al, "Platelet plasma membrane glycoproteins. Evidence for the presence of nonequivalent disulfide bonds using nonreduced-reduced two-dimensional gel electrophoresis", J Biol Chem. 252(6):2121-6 (Mar. 25, 1977).

Polgar J et al., "Platelet activation and signal transduction by convulxin, a C-type lectin from *Crotalus durissus terrificus* (tropical rattlesnake) venom via the p62/GPVI collagen receptor", J Biol Chem. 272(21):13576-83 (May 23, 1997).

Poole A et al., "The Fc receptor gamma-chain and the tyrosine kinase Syk are essential for activation of mouse platelets by collagen", EMBO J. 16(9):2333-41 (May 1, 1997).

Quek LS et al., "A role for Bruton's tyrosine kinase (Btk) in platelet activation by collagen", Curr Biol. 8(20):1137-40 (Oct. 8, 1998).

Rosenbaum V et al, "Temperature-gradient gel electrophoresis. Thermodynamic analysis of nucleic acids and proteins in purified form and in cellular extracts", Biophys Chem. 26(2-3):235-46 (May 9, 1987).

Ryo R et al., "Deficiency of P62, a putative collagen receptor, in platelets from a patient with defective collagen-induced platelet aggregation", Am J Hematol. 39(1):25-31 (Jan. 1992).

Saiki RK et al. "Analysis of enzymatically amplified beta-globin and HLA-DQ alpha DNA with allele-specific oligonucleotide probes", Nature. 324(6093):163-6 (Nov. 13-19, 1986).

Saiki RK et al., "Genetic analysis of amplified DNA with immobilized sequence-specific oligonucleotide probes", Proc Natl Acad Sci U S A. 86(16)6230-4 (Aug. 1989).

Saleeba JA et al, "Chemical cleavage of mismatch to detect mutations", Methods Enzymol. 217:286-95 (1993).

Sawai et al., "Direct production of the Fab fragment derived from the sperm immobilizing antibody using polymerase chain reaction and cDNA expression vectors", Am. J. Reprod. Immunol. 34:26-34 (1995).

Schulte et al, "Evidence for two distinct epitopes within collagen for activation of murine platelets," J Biol Chem 276(1):364-368 (Jan. 5, 2001).

Shaw et al., "Mouse/human chimeric antibodies to a tumor-associated antigen: biologic activity of the four human IgG subclasses", J. Natl. Cancer Inst. 80:1553-1559 (1988).

Sixma J.J.et al, "Platelet Adhesion to Collagen," Thrombosis and Haemostasis 74(1):454-459 (1995).

Sugiyama T et al., "A novel platelet aggregating factor found in a patient with defective collagen-induced platelet aggregation and autoimmune thrombocytopenia", Blood. 69(6):1712-20 (Jun. 1987).

Sugiyama T et al, "Functional role of the antigen recognized by an antiplatelet antibody specific for a putative collagen receptor in platelet-collagen interaction:" Int J. Hematol. 58(1-2):99-104 (Aug. 1993).

Sun et al., "Chimeric antibody with human constant regions and mouse variable regions directed against carcinoma-associated antigen 17-1A", Proc. Natl. Acad. Sci. USA 84:214-218 (1987).

Takahashi H et al., "Platelet membrane glycoprotein VI (GPVI) is necessary for collagen-induced aggregation and adhesion and anti-GP VI antibody induces platelet aggregation: An evidence obtained from a patient with systemic lupus erythematosus", Thromb Haemostas. 73:1197 (Abstract) (1995).

Thorpe et al., "The preparation and cytotoxic properties of antibody-toxin conjugates", Immunol. Rev. 62:119-158 (1982).

Tonra et al, "Rabbit IgG distribution in skin, spinal cord and DRG following systemic injection in rat", J. Neuroimmunol. 80:97-105 (1997).

Torelli A et al, "Advance and Adam: to algorithms for the analysis of global similarity between homologous informational sequences." Comput Appl Biosci. 10(1):3-5 (Feb. 1994).

Tsuji M et al., "A novel association of Fc receptor gamma-chain with glycoprotein VI and their co-expression as a collagen receptor in human platelets", J Biol Chem. 272(38):23528-31 (Sep. 19, 1997).

Tutt et al., "Trispecific F(ab.sup.1).sub.3 derivatives that use cooperative signaling via the TCR/CD3 complex and CD2 to activate and redirect resting cytotoxic T cells", J. Immunol. 147:60-69 (1991).

Van Zanten et al., "Increased platelet deposition on atherosclerotic coronary arteries", J. Clin. Invest. 93:615-632 (1994).

Verhoeyen et al., "Reshaping human antibodies: grafting an antilysozyme activity", Science 239:1534-1536 (1988).

Verkleij MW et al., "Simple collagen-like peptides support platelet adhesion under static but not under flow conditions: interaction via alpha2 beta1 and von Willebrand factor with specific sequences in native collagen is a requirement to resist shear forces", Blood. 91(10):3808-16 (May 15, 1998).

Wood et al., "The synthesis and in vivo assembly of functional antibodies in yeast", Nature 314:446-449 (1985).

www.ncbi.nlm.nih.gov Genbank Accession No. AA308708 "EST179519 HCC cell line (matastasis to liver in mouse) II *Homo sapiens* cDNA 5' end similar to EST containing Alu repeat, mRNA sequence" (Adams, M.D. et al.) (Apr. 18, 1997).

www.ncbi.nlm.nih.gov Genbank Accession No. AA494446 "ne38a02.s1 NCI_CGAP_Co3 *Homo sapiens* cDNA clone Image:899594 3', mRNA sequence". (NCI-CGAP http://www.ncbi.nlm.nih.gov/ncicgap). (Mar. 10, 1997).

www.ncbi.nlm.nih.gov. Genbank Accession No. AB035073 "*Homo sapiens* mRNA for platelet glycoprotein VI, complete cds" (Miura, Y.) (Nov. 16, 1999).

www.ncbi.nlm.nih.gov. Genbank Accession No. AB043819 "*Homo sapiens* GPVI mRNA for platelet glycoprotein VI-1, complete cds", (Ezumi and Takayama). (May 25, 2000.).

www.ncbi.nlm.nih.gov. Genbank Accession No. AB043820 "*Homo sapiens* GPVI mRNA for platelet glycoprotein VI-2, complete cds", (Ezumi and Takayama) (May 25, 2000).

www.ncbi.nlm.nih.gov. Genbank Accession No. AB043821 "*Homo sapiens* GPVI mRNA for platelet glycoprotein VI-3, complete cds" (Ezumi and Takayama) (May 25, 2000).

www.ncbi.nlm.nih.gov. Genbank Accession No. AB043943 "*Homo sapiens* GPVI gene for platelet glycoprotein VI, partial cds", (Ezumi and Takayama) (May 27, 2000).

www.ncbi.nlm.nih.gov. Genbank Accession No. AX046772 "Sequence 1 from Patent WO 00/68377" (Clemetson, K.J.) (Nov. 16, 2000).

www.ncbi.nlm.nih.gov. Genbank Accession No. NM_016363 "*Homo sapiens* platelet glycoprotein VI (GPVI), mRNA" (Ezumi et al.) (Oct. 2000).

www.ncbi.nlm.nih.gov. Genbank Accession No. U91928 "Human clone HL9 monocyte inhibitory receptor precursor mRNA, complete cds" (Arm, J.P.) (Mar. 4, 1997).

* cited by examiner

```
                                              M   S   P   S   P   T   A   L   F   C   L    11
GGAGTCGACCCACGCGTCCGCAGGGCTGAGGAACC ATG TCT CCA TCC CCG ACC GCC CTC TTC TGT CTT  68

G   L   C   L   G   R   V   P   A   Q   S   G   P   L   P   K   P   S   L   Q    31
GGG CTG TGT CTG GGG CGT GTG CCA GCG CAG AGT GGA CCG CTC CCC AAG CCC TCC CTC CAG  128

A   L   P   S   S   L   V   P   L   E   K   P   V   T   L   R   C   Q   G   P    51
GCT CTG CCC AGC TCC CTG GTG CCC CTG GAG AAG CCA GTG ACC CTC CGG TGC CAG GGA CCT  188

P   G   V   D   L   Y   R   L   E   K   L   S   S   R   Y   Q   D   Q   A        71
CCG GGC GTG GAC CTG TAC CGC CTG GAG AAG CTG AGT TCC AGC AGG TAC CAG GAT CAG GCA  248

V   L   F   I   P   A   M   K   R   S   L   A   G   R   Y   R   C   S   Y   Q    91
GTC CTC TTC ATC CCG GCC ATG AAG AGA AGT CTG GCT GGA CGC TAC CGC TGC TCC TAC CAG  308

N   G   S   L   W   S   L   P   S   D   Q   L   E   L   V   A   T   G   V   F   111
AAC GGA AGC CTC TGG TCC CTG CCC AGC GAC CAG CTG GAG CTC GTT GCC ACG GGA GTT TTT  368

A   K   P   S   L   S   A   Q   P   G   P   A   V   S   S   G   G   D   V   T   131
GCC AAA CCC TCG CTC TCA GCC CAG CCC GGC CCG GCG GTG TCG TCA GGA GGG GAC GTA ACC  428

L   Q   C   Q   T   R   Y   G   F   D   Q   F   A   L   Y   K   E   G   D   P   151
CTA CAG TGT CAG ACT CGG TAT GGC TTT GAC CAA TTT GCT CTG TAC AAG GAA GGG GAC CCT  488

A   P   Y   K   N   P   E   R   W   Y   R   A   S   F   P   I   I   T   V   T   171
GCG CCC TAC AAG AAT CCC GAG AGA TGG TAC CGG GCT AGT TTC CCC ATC ATC ACG GTG ACC  548

A   A   H   S   G   T   Y   R   C   Y   S   F   S   S   R   D   P   Y   L   W   191
GCC GCC CAC AGC GGA ACC TAC CGA TGC TAC AGC TTC TCC AGC AGG GAC CCA TAC CTG TGG  608

S   A   P   S   D   P   L   E   L   V   V   T   G   T   S   V   T   P   S   R   211
TCG GCC CCC AGC GAC CCC CTG GAG CTT GTG GTC ACA GGA ACC TCT GTG ACC CCC AGC CGG  668

L   P   T   E   P   P   S   S   V   A   E   F   S   E   A   T   A   E   L   T   231
TTA CCA ACA GAA CCA CCT TCC TCG GTA GCA GAA TTC TCA GAA GCC ACC GCT GAA CTG ACC  728

V   S   F   T   N   K   V   F   T   T   E   T   S   R   S   I   T   T   S   P   251
GTC TCA TTC ACA AAC AAA GTC TTC ACA ACT GAG ACT TCT AGG AGT ATC ACC ACC AGT CCA  788

K   E   S   D   S   P   A   G   P   A   R   Q   Y   Y   T   K   G   N   L   V   271
AAG GAG TCA GAC TCT CCA GCT GGT CCT GCC CGC CAG TAC TAC ACC AAG GGC AAC CTG GTC  848

R   I   C   L   G   A   V   I   L   I   I   L   A   G   F   L   A   E   D   W   291
CGG ATA TGC CTC GGG GCT GTG ATC CTA ATA ATC CTG GCG GGG TTT CTG GCA GAG GAC TGG  908

H   S   R   R   K   R   L   R   H   R   G   R   A   V   Q   R   P   L   P   P   311
CAC AGC CGG AGG AAG CGC CTG CGG CAC AGG GGC AGG GCT GTG CAG AGG CCG CTT CCG CCC  968
```

FIG.1A

```
       L   P   P   L   P   Q   T   R   K   S   H   G   G   Q   D   G   G   R   Q   D   331
      CTG CCG CCC CTC CCG CAG ACC CGG AAA TCA CAC GGG GGT CAG GAT GGA GGC CGA CAG GAT 1028

V   H   S   R   G   L   C   *                                                  340
      GTT CAC AGC CGC GGG TTA TGT TCA TGA                                              1055
```

CCGCTGAACCCCAGGCACGGTCGTATCCAAGGGAGGGATCATGGCATGGGAGGCGACTCAAAGACTGGCGTGTGTGGAG 1134

CGTGGAAGCAGGAGGGCAGAGGCTACAGCTGTGGAAACGAGGCCATGCTGCCTCCTCCTGGTGTTCCATCAGGGAGCCG 1213

TTCGGCCAGTGTCTGTCTGTCTGTCTGCCTCTCTGTCTGAGGGCACCCTCCATTTGGGATGGAAGGAATCTGTGGAGAC 1292

CCCATCCTCCTCCCTGCACACTGTGGATGACATGGTACCCTGGCTGGACCACATACTGGCCTCTTTCTTCAACCTCTCT 1371

AATATGGGCTCCAGACGGATCTCTAAGGTTCCCAGCTCTCAGGGTTGACTCTGTTCCATCCTCTGTGCAAAATCCTCCT 1450

GTGCTTCCCTTTGGCCCTCTGTGCTCTTGTCTGGTTTTCCCCAGAAACTCTCACCCTCACTCCATCTCCCACTGCGGTC 1529

TAACAAATCTCCTTTCGTCTCTCAGAACGGGTCTTGCAGGCAGTTTGGGTATGTCATTCATTTTCCTTAGTGTAAAACT 1608

AGCACGTTGCCCGCTTCCCTTCACATTAGAAAACAAGATCAGCCTGTGCAACATGGTGAAACCTCATCTCTACCAACAA 1687

AACAAAAAAACACAAAAATTAGCCAGGTGTGGTGGTGCATCCCTATACTCCCAGCAACTCGGGGGGCTGAGGTGGGAGA 1766

ATGGCTTGAGCCTGGGAGGCAGAGGTTGCAGTGAGCTGAGATCACACCACTGCACTCTAGCTCGGGTGACGAAGCCTGA 1845

CCTTGTCTCAAAAAATACAGGGATGAATATGTCAATTACCCTGATTTGATCATAGCACGTTGTATACATGTACTGCAAT 1924

ATTGCTGTCCACCCCATAAATATGTACAATTATGTATACATTTTTAAAATCATAAAAATAAGATAATGAAAAAAAAAA 2003

AAAAAAAAAAAAAAGGGCGGGCCGCTAGACTAGTCTAGAGAACA 2047

FIG.1B

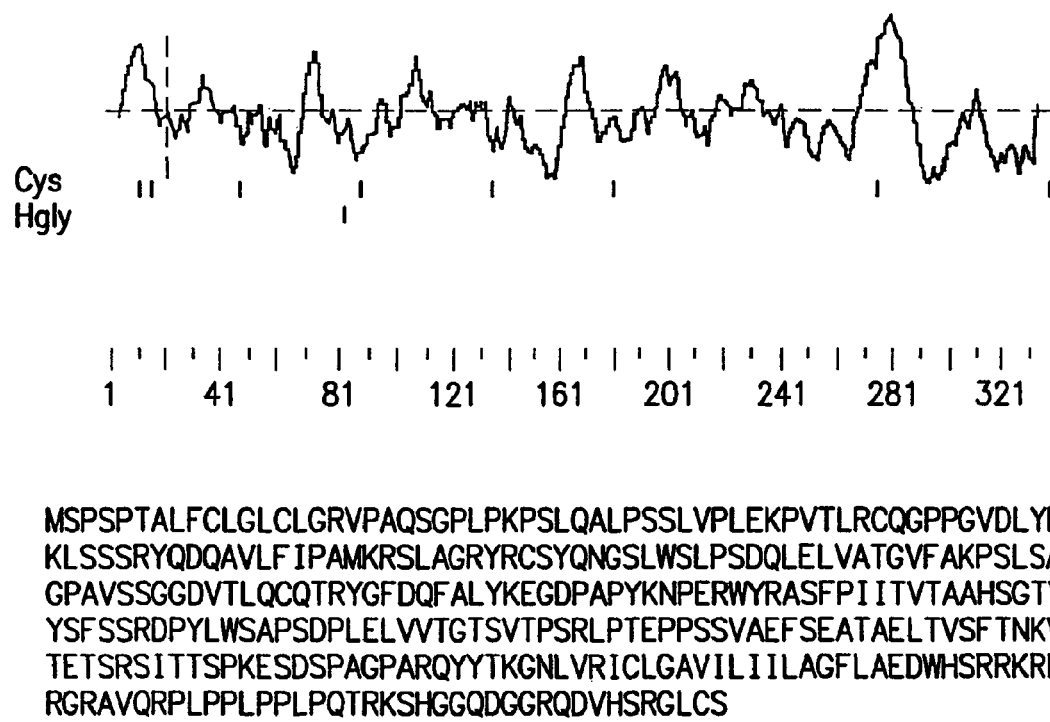

MSPSPTALFCLGLCLGRVPAQSGPLPKPSLQALPSSLVPLEKPVTLRCQGPPGVDLYRLE
KLSSSRYQDQAVLFIPAMKRSLAGRYRCSYQNGSLWSLPSDQLELVATGVFAKPSLSAQP
GPAVSSGGDVTLQCQTRYGFDQFALYKEGDPAPYKNPERWYRASFPIITVTAAHSGTYRC
YSFSSRDPYLWSAPSDPLELVVTGTSVTPSRLPTEPPSSVAEFSEATAELTVSFTNKVFT
TETSRSITTSPKESDSPAGPARQYYTKGNLVRICLGAVILIILAGFLAEDWHSRRKRLRH
RGRAVQRPLPPLPPLPQTRKSHGGQDGGRQDVHSRGLCS

FIG.2

```
         10        20        30        40        50        60        70
inputs ATGACGCCCGCCCTCACAGCCCTGCTCTGCCTTGGGCTGAGTCTGGGCCCCAGGACCCGCGTGCAGGCAG
       :::.: ::   :::   ::  :::::    ::::   ::::::::::.::::::: :   .: .:: :: :::::. .:
       ATGTCTCCATCCCCGACCGCCCTCTTCTGTCTTGGGCTGTGTCTGGGGCG-TGTGCCAGC--GCAGAGTG
         10        20        30        40        50        60

80        90        100       110       120       130
inputs GGCCCTTCCCCAAACCCACCCTCTGGGCTGAGCCAGGCTCTGTGAT-CAGCTGGGGGAGCCCCGTGACCA
       .:::   ::::::::.::::.::::  .::::  .:::   .::::       ::::.:.:::: ::::::
       GACCGCTCCCCAAGCCCTCCCTCCAGGCTCTGCCCAGCTCCCTGGTGCCCCTGGAGAAGCCA-GTGACCC
         70        80        90        100       110       120       130

140       150       160       170       180       190       200
inputs TCTGGTGTCAGGGGAGCCTGGAGGCCCAGGAGTACCGACTGGATAAAGAGGGAAGCCCAGAGCCCTTGGA
       ::  ::::: :::::  .:::           :::.::: ::.  ::: :..      ::: .:::     ...
       TCCGGTGCCAGGG--ACCT------CCGGGCGTG--GACCTGTA--------CCGCCTGGAG-----AAG
         140       150       160       170       180

210       220       230       240       250       260       270
inputs CAGAAATAACCCACTGGAACCCAAGAACAAGGCCAGATTCTCCATCCCCATCCATGACAGAGCACCATGCG
       ::.:..:  ::   ::.::::.:  :.::::: :::  .       :::   ::::.:    ::::.    .. .
       CTGAGTT--CCAGCAGGTACC-AGGATCA-GGCAGTCCTCTTCATCCCGGCCATGAAGAGAAGTCTGGCT
         190       200       210       220       230       240

280       290       300       310       320       330       340
inputs GGGAGATACCGCTGCCACTATTACAGCTCTGCAG--GCTGGTCAGAGCCCAGCGACCCCCTGGAGCTGGT
       ::. : :::::::::   :::    :::  .: : ::  ::::::  .::::::::::: ::::::::: ::
       GGACGCTACCGCTGCTCCTAC--CAGAACGGAAGCCTCTGGTCCCTGCCCAGCGACCAGCTGGAGCTCGT
         250       260       270       280       290       300       310

350       360       370       380       390       400       410
inputs GATGACAGGATTCTACAACAAACCCACCCTCTCAGCCCTGCCCAGCCCTGTGGTGGCCTCAGGGGGGAAT
       .   ::::::  :  ..  .:::::::.: ::::::::::::.::::.::: : :::: :  : :::::.::::
       TGCCACGGGAGTTTTTGCCAAACCCTCGCTCTCAGCCCAGCCCGGCCCGGCGGTGTCGTCAGGAGGGGAC
         320       330       340       350       360       370       380

420       430       440       450       460       470       480
inputs ATGACCCTCCGATGTGGCTCACAGAAGGGATATCACCATTTTTGTTCTGATGAAGGAAGGAGAACACCAGC
       .:::::: :...:: . ..:.::::: :: :.: :::::::::::...:::::::::
       GTAACCCTACAGTGTCAGACTCGGTATGGCTTTGACCAATTTGCTCTGTACAAGGAAGG----------
         390       400       410       420       430       440

490       500       510       520       530       540       550
inputs TCCCCCGGACCCTGGACTCACAGCAGCTCCACAGTGGGGGGTTCCAGGCCCTGTTCCCTGTGGGCCCCGT
       ::::::::       :           :      :::::.       ...
       -----GGACCCTG---------------------C---GCCCTA-------------CAA
            450                         460
```

FIG.3A

```
         560       570       580       590       600       610       620
inputs GAACCCCAGCCACAGGTGGAGGTTCACATGCTATTACTATTATATGAACACCCCCAGGTGTGGTCCCAC
       ::: ::..   .:..:::.:. :::: :         ::            :::::          ::
       GAATCCCGA·····GAGATGGTAC·CGGGCTAGT····TT············CCCCAT·········CAT
         470       480       490                          500

630       640       650       660       670       680       690
inputs CCCAGTGACCCCCTGGAGATTCTGCCCTCAGGCGTGTCTAGGAAGCCCTCCCTCCTGACCCTGCAGGGCC
       : :.:::::: ::           :::: :::
       CACGGTGACCGCC··········GCCCACAG·····································
         510                 520

700       710       720       730       740       750       760
inputs CTGTCCTGGCCCCTGGGCAGAGCCTGACCCTCCAGTGTGGCTCTGATGTCGGCTACGACAGATTTGTTCT
                   :::.:::.     ::::                      :::::         ::::
       ············CGGAACCTA·····CCGATG················CTACAGC·······TTCT
                   530          540                                   550

770       780       790       800       810       820       830
inputs GTATAAGGAGGGGGAACGTGACTTCCTCCAGCGCCCTGGCCAGCAGCCCCAGGCTGGGCTCTCCCAGGCC
                                               ::::::::
       ······································CCAGCAG······················

840       850       860       870       880       890       900
inputs AACTTCACCCTGGGCCCTGTGAGCCCCTCCCACGGGGGCCAGTACAGGTGCTATGGTGCACACAACCTCT
                 ::.:::.                                               .:::
       ··········GGACCCA·············································TACCT··
                 560

910       920       930       940       950       960       970
inputs CCTCCGAGTGGTCGGCCCCCAGCGACCCCCTGAACATCCTGATGGCAGGACAGATCTATGACACCGTCTC
              :::::::::::::::::::::::::::::.:    ::.       !.::          
       ·······GTGGTCGGCCCCCAGCGACCCCCTGGA··········GCT·········TGTG··········
              570       580       590                600

980       990      1000      1010      1020      1030      1040
inputs CCTGTCAGCACAGCCGGGCCCCACAGTGGCCTCAGGAGAGAACGTGACCCTGCTGTGTCAGTCATGGTGG
        ::::       :.::   ::.:.:::.::                 :::::.     :...
       ···GTCA······CAGGAACCTCTGTGACC················CCCAGC·····CGGT········
          610       620                              630

1050      1060      1070      1080      1090      1100      1110
inputs CAGTTTGACACTTTCCTTCTGACCAAAGAAGGGGCAGCCCATCCCCCACTGCGTCTGAGATCAATGTACG
                 :.::..:.: :          ::  ::.:::::                     .:::
       ···········TACCAACAGAAC··········CA··CCTTCC····················TCG
                  640                     650

1120      1130      1140      1150      1160      1170      1180
inputs GAGCTCATAAGTACCAGGCTGAATTCCCCATGAGTCCTGTGACCTCAGCCCACGCGGGGACCTACAGGTG
       :::             :::.:::::::.:         :::.:::::      :::::.      :::: .
       GTA·············GCAGAATTCTC·········AGAAGCCAC······CGCTGA·····ACTG··A
       660                  670                680             690
```

FIG.3B

```
       1190      1200      1210      1220      1230      1240      1250
inputs CTACGGCTCATACAGCTCCAACCCCCACCTGCTGTCTTTCCCCAGTGAGCCCCTGGAACTCATGGTCTCA
       C··CGTCTCATTCA···CAAAC········AAAGTCTT··CACAA·······CTGAGACT·····TCT··
          700            710         720            730
       1260      1270      1280      1290      1300      1310      1320
inputs GGACACTCTGGAGGCTCCAGCCTCCCACCCACAGGGCCGCCCTCCACACCTGGTCTGGGAAGATACCTGG
       ········AGGAGTATC··ACCACCAGTCCAAAGGA··GTCAGACTCTCCAG··CTGG···········
               740         750          760         770
       1330      1340      1350      1360      1370      1380      1390
inputs AGGTTTTGATTGGGGTCTCGGTGGCCTTCGTCCTGCTGCTCTTCCTCCTCCTCTTCCTCCTCCTCCGACG
       ···················TCCTGC··········CCGCCAGTA····CTACACCAAGG
                          780            790             800
       1400      1410      1420      1430      1440      1450      1460
inputs TCAGCGTCACAGCAAACACAGGACATCTGACCAGAGAAAGACTGATTTCCAGCGTCCTGCAGGGGCTGCG
       GCAAC············CTGGTC················CGGATAT···GCCTC·····GGGGCTG··
       810                               820             830
       1470      1480      1490      1500      1510      1520      1530
inputs GAGACAGAGCCCAAGGACAGGGGCCTGCTGAGGAGGTCCAGCCCAGCTGCTGACGTCCAGGAAGAAAACC
       ·····TGATCCTAATAA·····TCCTG··GCGGGGTTTCTG········GCAGA··GGACTGG········C
            840                850    860              870
       1540      1550      1560      1570      1580      1590      1600
inputs TCTATGCTGCCGTGAAGGACACACAGTCTGAGG·ACAGGGTGGAGCTGGACAGT·CAGAGCCCACACGAT
       AC·····AGCCG··GAGGAAGCGC···CTGCGGCACAGGG····GCAGGGCTGTGCAGAGGCCGCT····
              880        890         900              910
       1610      1620      1630      1640      1650      1660      1670
inputs GAAGACCCCCAGGCAGTGACGTATGCCCCGGTGAAACACTCCAGTCCTAGGAGAGAAATGGCCTCTCCTC
       ····TCC················GCCCCTG··············································CCGC····C
           930                        940
       1680      1690      1700      1710      1720      1730      1740
inputs CCTCCTCACTGTCTGGGGAATTCCTGGACACAAAGGACAGACAGGTGGAAGAGGACAGGCAGATGGACAC
       CCTCC·CGCAGAC·········CCGGAAATCA·····CA··CGGG······GGTCAGG···ATGGA···
       950                 960                970            980
       1750      1760      1770      1780      1790      1800      1810
inputs TGAGGCTGCTGCATCTGAAGCCTCCCAGGATGTGACCTACGCCCAGCTGCACAGCTTGACCCTTAGACGG
       ···GGC·····CGAC···········AGGATGTT··············CACAGC············CG·
                                990                1000
       1820      1830      1840      1850      1860      1870      1880
inputs AAGGCAACTGAGCCTCCTCCATCCCAGGAAGGGGAACCTCCAGCTGAGCCCAGCATCTACGCCACTCTGG
       ························CGGGTTATG·················TTCA···········
                                1010
       1890
inputs CCATCCAC
       ········
```

FIG.3C

```
             10        20        30        40        50        60
inputs  MSPSPTALFCLGLCLG-RVPAQSGPLPKPSLQALPSSLVPLEKPVTLRCQGPPGVDLYRLEKLSSS---
        ::.  :::.::::: ::  ..:.::::::.: : :.:..  :::::.:::. ..  ::::. ::.
        MTPALTALLCLGLSLGPRTRVQAGPFPKPTLWAEPGSVISWGSPVTIWCQGSLEAQEYRLDKEGSPEPLD
             10        20        30        40        50        60        70

70        80        90       100       110       120       130
inputs  RYQ-----DQAVLFIPAMKRSLAGRYRCSYQNGSLWSLPSDQLELVATGVFAKPSLSAQPGPAVSSGGDV
        :.     ..: :::. ::::.   ::  :::::::: : .... :: ::::::.:::. :.:.:.:..
        RNNPLEPKNKARFSIPSMTEHHAGRYRCHYYSSAGWSEPSDPLELVMTGFYNKPTLSALPSPVVASGGNM
             80        90       100       110       120       130       140 inputs  TLQCQT----------------------------------------RY-----------------
        :::: .                                        ..
        TLRCGSQKGYHHFVLMKEGEHQLPRTLDSQQLHSGGFQALFPVGPVNPSHRWRFTCYYYYMNTPQVWSHP
             150       160       170       180       190       200       210

140       150
inputs  ----------------------------GFDQFALYKEGDP----------------
                                    .:..:.::::.
        SDPLEILPSGVSRKPSLLTLQGPVLAPGQSLTLQCGSDVGYDRFVLYKEGERDFLQRPGQQPQAGLSQAN
             220       230       240       250       260       270       280

160
inputs  -----------APYK---------------NP--------------------------ERW--
                   ..::                ..                              :
        FTLGPVSPSHGGQYRCYGAHNLSSEWSAPSDPLNILMAGQIYDTVSLSAQPGPTVASGENVTLLCQSWWQ
             290       300       310       320       330       340       350

170       180       190       200
inputs  ------------------------YRASFPIITVTAAHSGTYRCYSFSSRDPYLWSAPSDPLELVVTG
                                :.: ::.  ::.::.:::::::: :.::.:: .:::::::::.:
        FDTFLLTKEGAAHPPLRLRSMYGAHKYQAEFPMSPVTSAHAGTYRCYGSYSSNPHLLSFPSEPLELMVSG
             360       370       380       390       400       410       420

210       220       230       240       250       260
inputs  TSVTPSRLPTEPPSS--VAEFSEATAELTVSFTNKVF--------TTETSRSITTSPKESD--SPAGPA-
        .:: .::::: :::: .  .:.: ::: . . . ..         . ..:.  .:::.::   :...
        HSGGSSLPPTGPPSTPGLGRYLEVLIGVSVAFVLLLFLLLFLLLRRQRHSKHRTSDQRKTDFQRPAGAAE
             430       440       450       460       470       480       490

270       280       290
inputs  RQYYTKGNLVRICLGAVIL-----IILAGFLAEDW--------------------HSRRKR-------
        .:::.  :.:. .: ::   . :  .:: .  . .:.                  ::  :
        TEPKDRGLLRRSSPAADVQEENLYAAVKDTQSEDRVELDSQSPHDEDPQAVTYAPVKHSSPRREMASPPS
             500       510       520       530       540       550       560

300                       310       320       330
inputs  ------LRHRGRAVQ--RPL--------------PPLPPLPQTRK------SHGGQDGGRQDVHSRGLC
              : .:  ..   .:.              :.: .::.: .      :  :.   ::  :. .. 
        SLSGEFLDTKDRQVEEDRQMDTEAAASEASQDVTYAQLHSLTLRRKATEPPPSQEGEPPAEPSIYATLAI
             570       580       590       600       610       620       630 inputs  S
        H
```

FIG.4

```
            *->GesvtLtCsvsgfgppgvsvtWyfkngk.lgpsllgysysrlesgek
              + vtL+C+       + v  y + k  ++        r++ +
hT268   41   EKPVTLRCQGP-----PGVDLY-RLEKISSS--------RYQDQ--  70 anlsegrfsissltLtissvekeDsGtYtCvv<-*
                ++L i    +++  +G Y+C
hT268   71   -----------AVLFIPAMKRSLAGRYRCSY          90
```

FIG.5A

```
            *->GesvtLtCsvsgfgppgvsvtWyfkngk.lgpsllgysysrlesgek
              G++vtL+C+++    + ++ y k+g++ +       y+++
hT268  127   GGDVTLQCQTR---YGFDQFALY-KEGDpAP-----YKNPERWYR--  162 anlsegrfsissltLtissvekeDsGtYtCvv<-*
                ++++i++v++   sGtY+C
hT268  163   -----------ASFPIITVTAAHSGTYRCYS          182
```

FIG.5B

```
                                                                M   S   P   A       4
GAGTCGACCCACGCGTCCGCTTCCCTGCTTGGCCACATAGCTCAGGACTGGGTTGCAGAACC ATG TCT CCA GCC      74

S   P   T   F   F   C   I   G   L   C   V   L   Q   V   I   Q   T   Q   S   G    24
TCA CCC ACT TTC TTC TGT ATT GGG CTG TGT GTA CTG CAA GTG ATC CAA ACA CAG AGT GGC    134

P   L   P   K   P   S   L   Q   A   Q   P   S   S   L   V   P   L   G   Q   S    44
CCA CTC CCC AAG CCT TCC CTC CAG GCT CAG CCC AGT TCC CTG GTA CCC CTG GGT CAG TCA    194

V   I   L   R   C   Q   G   P   P   D   V   D   L   Y   R   L   E   K   L   K    64
GTT ATT CTG AGG TGC CAG GGA CCT CCA GAT GTG GAT TTA TAT CGC CTG GAG AAA CTG AAA    254

P   E   K   Y   E   D   Q   D   F   L   F   I   P   T   M   E   R   S   N   A    84
CCG GAG AAG TAT GAA GAT CAA GAC TTT CTC TTC ATT CCA ACC ATG GAA AGA AGT AAT GCT    314

G   R   Y   R   C   S   Y   Q   N   G   S   H   W   S   L   P   S   D   Q   L   104
GGA CGG TAT CGA TGC TCT TAT CAG AAT GGG AGT CAC TGG TCT CTC CCA AGT GAC CAG CTT    374

E   L   I   A   T   G   V   Y   A   K   P   S   L   S   A   H   P   S   S   A   124
GAG CTA ATT GCT ACA GGT GTG TAT GCT AAA CCC TCA CTC TCA GCT CAT CCC AGC TCA GCA    434

V   P   Q   G   R   D   V   T   L   K   C   Q   S   P   Y   S   F   D   E   F   144
GTC CCT CAA GGC AGG GAT GTG ACT CTG AAG TGC CAG AGC CCA TAC AGT TTT GAT GAA TTC    494

V   L   Y   K   E   G   D   T   G   P   Y   K   R   P   E   K   W   Y   R   A   164
GTT CTA TAC AAA GAA GGG GAT ACT GGG CCT TAT AAG AGA CCT GAG AAA TGG TAC CGG GCC    554

N   F   P   I   I   T   V   T   A   A   H   S   G   T   Y   R   C   Y   S   F   184
AAT TTC CCC ATC ATC ACA GTG ACT GCT GCT CAC AGT GGG ACG TAC CGG TGT TAC AGC TTC    614

S   S   S   P   Y   L   W   S   A   P   S   D   P   L   V   L   V   V   T   204
TCC AGC TCA TCT CCA TAC CTG TGG TCA GCC CCG AGT GAC CCT CTA GTG CTT GTG GTT ACT    674

G   L   S   A   T   P   S   Q   V   P   T   E   E   S   F   P   V   T   E   S   224
GGA CTC TCT GCC ACT CCC AGC CAG GTA CCC ACG GAA GAA TCA TTT CCT GTG ACA GAA TCC    734

S   R   R   P   S   I   L   P   T   N   K   I   S   T   T   E   K   P   M   N   244
TCC AGG AGA CCT TCC ATC TTA CCC ACA AAC AAA ATA TCT ACA ACT GAA AAG CCT ATG AAT    794

I   T   A   S   P   E   G   L   S   P   P   I   G   F   A   H   Q   H   Y   A   264
ATC ACT GCC TCT CCA GAG GGG CTG AGC CCT CCA ATT GGT TTT GCT CAT CAG CAC TAT GCC    854

K   G   N   L   V   R   I   C   L   G   A   T   I   I   I   I   L   L   G   L   284
AAG GGG AAT CTG GTC CGG ATA TGC CTT GGT GCC ACG ATT ATA ATA ATT TTG TTG GGG CTT    914

L   A   E   D   W   H   S   R   K   K   C   L   Q   H   R   M   R   A   L   Q   304
CTA GCA GAG GAT TGG CAC AGT CGG AAG AAA TGC CTG CAA CAC AGG ATG AGA GCT TTG CAA    974

R   P   L   P   P   L   P   L   A   *                                            314
AGG CCA CTA CCA CCC CTC CCA CTG GCC TAG                                           1004

AAATAACTTGGCTTTCAGCAGAGGGATTGACCAGACATCCATGCACAACCATGGACATCACCACTAGAGCCACAGACAT 1083
GGACATACTCAAGAGTGGGGAGGTTATATAAAAAAATGAGTGTGGAGAATAAATGCAGAGCCAACAAGGTGAAAAAAAA 1162
A                                                                               1163
```

FIG.6

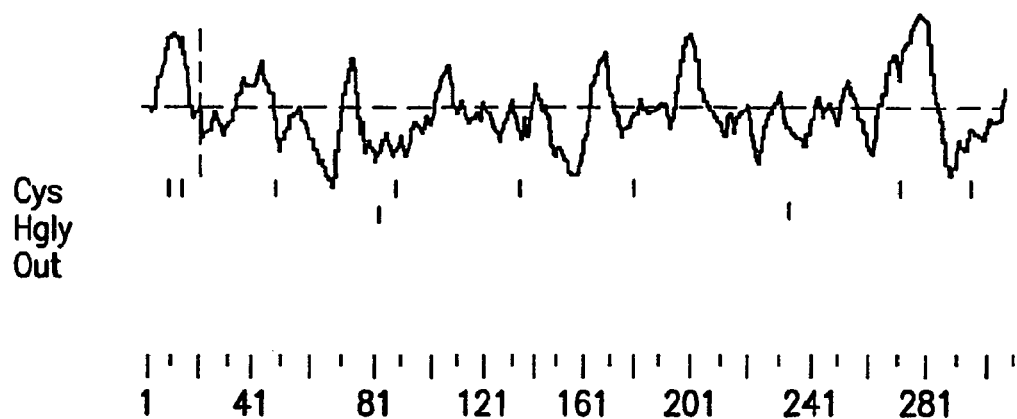

MSPASPTFFCIGLCVLQVIQTQSGPLPKPSLQAQPSSLVPLGQSVILRCQGPPDVDLYRL
EKLKPEKYEDQDFLFIPTMERSNAGRYRCSYQNGSHWSLPSDQLELIATGVYAKPSLSAH
PSSAVPQGRDVTLKCQSPYSFDEFVLYKEGDTGPYKRPEKWYRANFPIITVTAAHSGTYR
CYSFSSSSPYLWSAPSDPLVLVVTGLSATPSQVPTEESFPVTESSRRPSILPTNKISTTE
KPMNITASPEGLSPPIGFAHQHYAKGNLVRICLGATIIIILLGLLAEDWHSRKKCLQHRM
RALQRPLPPLPLA

FIG.7

```
              10        20        30        40        50        60        70
inputs  ATGACGCCCGCCCTCACAGCCCTGCTCTGCCTTGGGCTGAGTCTGGGCCCCAGGACCCGCGTGCAGGCAG
        :::..: :: .::: ::::  ::   .::  :::    :::::..:
        ATGTCTCCAGCC·TCAC··CC·····ACTTTCTT···CTGTAT····························
              10        20          30

80        90       100       110       120       130       140
inputs  GGCCCTTCCCCAAACCCACCCTCTGGGCTGAGCCAGGCTCTGTGATCAGCTGGGGGAGCCCCGTGACCAT
                                    :::::::             :::::..:::
        ·······················TGGGCTG··········TGTGTACTGC·················
                                                    40

150       160       170       180       190       200       210
inputs  CTGGTGTCAGGGGAGCCTGGAGGCCCAGGAGTACCGACTGGATAAAGAGGGAAGCCCAGAGCCCTTGGAC
                                     :.::.:.:::                :::. ::::: :::
        ·····················AAGTGATCC···············AAACACAGAG····TGG··
                                50                                60       70

220       230       240       250       260       270       280
inputs  AGAAATAACCCACTGGAACCCAAGAACAAGGCCAGATTCTCCATCCCATCCATGACAGAGCACCATGCGG
        ::::::    :::   ::::       ::..:::: :::: :
        ········CCCACT····CCC·····CAAG··········CCTTCCC·TCCAGG··············
                        80                        90

290       300       310       320       330       340       350
inputs  GGAGATACCGCTGCCACTATTACAGCTCTGCAGGCTGGTCAGAGCCCAGCGACCCCCTGGAGCTGGTGAT
        : :..::  ::   ::                           :::. :::::.:. :::::::: :.:
        ········CTCAGCC·····················CAGTTCCCTG·GTACCCCTGGGTCAG·····
                 100                                  110       120

360       370       380       390       400       410       420
inputs  GACAGGATTCTACAACAAACCCACCCTCTCAGCCCTGCCCCAGCCCTGTGGTGGCCTCAGGGGGGAATATG
        .::: :: :..::                                    ::..:::: :  ::::::.
        ·TCAG··TTATTC························TGAGGTG·C··CAGGGA·······
        130                                          140       150

430       440       450       460       470       480
inputs  ACCCTCC·GATGTGGCTCACAGAAGGGATATCACCATTTTGTTCTGATGAAGGAAGGAGAACACCAGCTC
        :::::  :::::::::          :   ::::::::.   . ...:::::..
        ··CCTCCAGATGTGG········ATTTATATCGCCTGGAGAAACTGAAA············
           160                  170       180        190

490       500       510       520       530       540       550
inputs  CCCCGGACCCTGGACTCACAGCAGCTCCACAGTGGGGGGTTCCAGGCCCTGTTCCCTGTGGGCCCCGTGA
        :::::     ::                :::. :....:: ::..:    ::: ::         :..:
        ··CCGGA·····GA················AGTATGAAGATCAAGAC···TTTCTCTT········CATT·
                                        200       210            220
```

FIG. 8A

```
        560       570       580       590       600       610       620
inputs ACCCCAGCCACAGGTGGAGGTTCACATGCTATTACTATTATATGAACACCCCCAGGTGTGGTCCCACCC
       :::.:::  .:,...::.    :::::          :.,::      ::::.:
          ---CCAACCATGGAAAGAAGTA---ATGCT------------GGAC--------GGTAT---------
              230       240       250                260

630       640       650       660       670       680       690
inputs CAGTGACCCCCTGGAGATTCTGCCCTCAGGCGTGTCTAGGAAGCCCTCCCTCCTGACCCTGCAGGGCCCT
       :..,::  : ::  .           ::::.      ..::,:: :                .:..: :: :
         CGATG---CTCTTA-----------TCAGA------ATGGGAGTC-------------ACTGGTCTCT
               270                 280                              290

700       710       720       730       740       750       760
inputs GTCCTGGCCCCTGGGCAGAGCCTGACCCTCCAGTGTGGCTCTGATGTCGGCTACGACAGATTTGTTCTGT
                :::..:          :::::  : ..:.:    ::..::     :::::
        --------CCCAAG---------TGACCAGCTTGAG-----CTAATT---GCTAC---------------
                300               310       320

770       780       790       800       810       820       830
inputs ATAAGGAGGGGGAACGTGACTTCCTCCAGCGCCCTGGCCAGCAGCCCCAGGCTGGGCTCTCCCAGGCCAA
       :::.: :   ...:  ..::   ::::                                 .:::::
         ---AGGTGTGTATGCTAAAC--CCTC----------------------------ACTCTC--------
              330       340                                    350

840       850       860       870       880       890       900
inputs CTTCACCCTGGGCCCTGTGAGCCCCTCCCACGGGGGCCAGTACAGGTGCTATGGTGCACACAACCTCTCC
                               ::: : :::::              :::
        ----------------AGCTCATCCCA----------------GCT---------------------
                         360

910       920       930       940       950       960       970
inputs TCCGAGTGGTCGGCCCCCAGCGACCCCCTGAACATCCTGATGGCAGGACAGATCTATGACACCGTCTCCC
                        :::::.. :::      ::   :.::::::  :::   .:::::.: :.
        ----------------CAGCAGTCCC-------TC---AAGGCAGG---GAT--GTGACTCTGA-----
                         370              380           390       400

980       990       1000      1010      1020      1030      1040
inputs TGTCAGCACAGCCGGGCCCCACAGTGGCCTCAGGAGAGAACGTGACCCTGCTGTGTCAGTCATGGTGGCA
       .::     :::.:. :::: :                                 ::::  .:..::.
        AGT------GCCAGAGCCCATA---------------------------------CAGTTTTGATGA--
                  410                                              420

1050      1060      1070      1080      1090      1100      1110
inputs GTTTGACACTTTCCTTCTGACCAAAGAAGGGGCAGCCCATCCCCCACTGCGTCTGAGATCAATGTACGGA
                .:::  :::::..  :::::::::::       ::    ::::  :  ::  :  :..,  : ::
        ---------ATTCGTTCTATACAAAGAAGGGG-------AT------ACTGGGCCTTATA--AGAGACCTGA
                  430       440       450              460             470
```

FIG.8B

```
        1120      1130      1140      1150      1160      1170      1180
inputs GCTCATAAGTACCAGGCTGAATTCCCCATGAGTCCTGTGACCTCAGCCCACGCGGGGACCTACAGGTGCT
       :    :...:::: :.::::: :..:::: .:::... ::::: ::: :::.      :::::  :::.
       G--AAATGGTACCGGGCCAATTTCCCCATCATCACAGTGACTGCTGCTCACAGTGGGACGTACCGGTGTT
          480       490       500       510       520       530       540

1190      1200      1210      1220      1230      1240      1250
inputs ACGGCTCATACAGCTCCAACCCCCACCTGCTGTCTTTCCCCAGTGAGCCCCTGGAACTCATGGTCTCAGG
       ::.:::    :   :::::::  .  :: ::::: :::.  :::  ::::: ::  ::..:.:: .::::  .:.::
       ACAGCTTCTCCAGCTCATCTCCATACCTGTGGTCAGCCCCGAGTGACCCTCTAGTGCTTGTGGTTACTGG
          550       560       570       580       590       600       610

1260      1270      1280      1290      1300      1310      1320
inputs ACACTCTGGAGGCTCCAGCCTCCCACCCACAGGGCCGCCCTCCACACCTGGTCTGGGAAGATACCTGGAG
       :::.:::::      :::   :::::::::   :::  .::::.:        ::.   .::..  :::.::::
       ACTCTCTG------CCA--CTCCCAGCC--AGGT--ACCCAC-------GGA-AGAATCATTTCCTG---
          620         630       640       650                660

1330      1340      1350      1360      1370      1380      1390
inputs GTTTTGATTGGGGTCTCGGTGGCCTTCGTCCTGCTGCTCTTCCTCCTCCTCTTCCTCCTCCTCCGACGTC
        :::          :.:.. :::     :::.: .:  :::::::          ::::: ::      :::. .::..
       ----TGA---------CAGAATCCT----CCAGGAGACCTTCCA-----TCTTAC----CCACAAACAAA
              670             680             690            700

1400      1410      1420      1430      1440      1450      1460
inputs AGCGTCACAGCAAACACAGGACATCTGACCAGAGAAAGACTGATTTCCAGCGTCCTGCAGGGGCTGCGGA
       :     :.:::        .::::       :.:::....::         : :  ::. : :::.: ::::::::::
       A---TATCTACAA---CTGAA----AAGCCTATGAATATC--ACTGCCT-C-TCCAG-AGGGGCTG----
         710       720           730       740            750

1470      1480      1490      1500      1510      1520      1530
inputs GACAGAGCCCAAGGACAGGGGCCTGCTGAGGAGGTCCAGCCCAGCTGCTGACGTCCAGGAAGAAAACCTC
            :::::.          ::          :.  .::  .::  :: ::  :.:::.                  :
       -----AGCCCT----------CC-----AATTGGTTTTGCTCATCAGCA--------------------C
             760            770            780

1540      1550      1560      1570      1580      1590      1600
inputs TATGCTGCCGTGAAGGACACACAGTCTGAGGACAGGGTGGAGCTGGACAGTCAGAGCCCACACGATGAAG
       :::::                           :::.:: :.: :::::.:              :::. ...
       TATGC---------------------------CAAGGGGAATCTGGTC------------CGGATATG
        790                             800                           810

1610      1620      1630      1640      1650      1660      1670
inputs ACCCCCAGGCAGTGACGTATGCCCCGGTGAAACACTCCAGTCCTAGGAGAGAAATGGCCTCTCCTCCCTC
          ::  .:::           ::::: ::::.:                    :: .:  :.....::
       ---CCTTGG---------TGCCACGAT---------------TATAATAATTTTGT-------------
           820                 830                        840

1680      1690      1700      1710      1720      1730      1740
inputs CTCACTGTCTGGGGAATTCCTGGACACAAAGGACAGACAGGTGGAAGAGGACAGGCAGATGGACACTGAG
          ........      ::::::: ::.::.  ::.::::::.::           :::.:.::::::. :
       --------TGGGGCTT--CTAG---CAGAGGATTGGC-----------ACAGTCGGAAGAA-----AT
                 850       860                             870       880
```

FIG.8C

```
        1750      1760      1770      1780      1790      1800      1810
inputs GCTGCTGCATCTGAAGCCTCCCAGGATGTGACCTACGCCCAGCTGCACAGCTTGACCCTTAGACGGAAGG
       ::  ::::::.:.        ::::::::::.::                   ::::  .:          .::::
       GC--CTGCAACA---------CAGGATGAGA-----------------GCTTTGC----------AAAGG
            890                900                          910

1820      1830      1840      1850      1860      1870      1880
inputs CAACTGAGCCTCCTCCATCCCAGGAAGGGGAACCTCCAGCTGAGCCCAGCATCTACGCCACTCTGGCCAT
        : ::::.      ::.::            :::::                      :.::::::::
       CCACTA-----CCACC---------------CCTCC---------------------CACTGGCC--
         920                           930

1890
inputs CCAC
```

FIG. 8D

```
                 10        20        30        40        50        60
inputs  MSPASPTFFCIGLCVLQVIQTQSGPLPKPSLQAQPSSLVPLGQSVILRCQGPPDVDLYRLEKL-KPEKYE
         :.::   ...:.::  . . ...:.::.:::.:  :.:.:...  :  .:.....::.  ...  ::::.:   ::  .
        MTPALTALLCLGLSLGPRTRVQAGPFPKPTLWAEPGSVISWGSPVTIWCQGSLEAQEYRLDKEGSPEPLD
                 10        20        30        40        50        60        70
           70        80        90       100       110       120       130
inputs  DQDFL-------F-IPTMERSNAGRYRCSYQNGSHWSLPSDQLELIATGVYAKPSLSAHPSSAVPQGRDV
         ..  :       : :::.:    .:::::::  :  ...  ::  :::.:::.  ::  .:.:.:::  ::..:.  ..
        RNNPLEPKNKARFSIPSMTEHHAGRYRCHYYSSAGWSEPSDPLELVMTGFYNKPTLSALPSPVVASGGNM
             80        90       100       110       120       130       140 inputs  TLKC--QSPY----------------------------------------------------------
         :::.  :   :
        TLRCGSQKGYHHFVLMKEGEHQLPRTLDSQQLHSGGFQALFPVGPVNPSHRWRFTCYYYYMNTPQVWSHP
               150       160       170       180       190       200       210

140       150
inputs  ----------------------------------SFDEFVLYKEGD--------------------
                                          ..:  :::::::::.
        SDPLEILPSGVSRKPSLLTLQGPVLAPGQSLTLQCGSDVGYDRFVLYKEGERDFLQRPGQQPQAGLSQAN
               220       230       240       250       260       270       280

160
inputs  ----------TGPYK------------------------------RP-------------EKW--
                   :.:..                                  .:                . :
        FTLGPVSPSHGGQYRCYGAHNLSSEWSAPSDPLNILMAGQIYDTVSLSAQPGPTVASGENVTLLCQSWWQ
               290       300       310       320       330       340       350

170       180       190       200
inputs  ----------------------YRANFPIITVTAAHSGTYRCYSFSSSSPYLWSAPSDPLVLVVTG
                               :.::.:.  :..::.::::::.   :::.  :  :  :.:.:  :.:.:
        FDTFLLTKEGAAHPPLRLRSMYGAHKYQAEFPMSPVTSAHAGTYRCYGSYSSNPHLLSFPSEPLELMVSG
               360       370       380       390       400       410       420

210              220
inputs  LSATPSQVPTEES---------------FPV-----------------------------------
         :.  .:  ::  .                 :  .
        HSGGSSLPPTGPPSTPGLGRYLEVLIGVSVAFVLLLFLLLFLLLRRQRHSKHRTSDQRKTDFQRPAGAAE
               430       440       450       460       470       480       490

230       240       250       260       270
input   TESS-----RRPS---------ILPTNKISTTEKPMNI-TASPEGLSP-PIGFAH--QHYAKGNLVR--I
         ::.       ::::           . .    :.   . .    . .:   :   .  :   . ..::
        TEPKDRGLLRRSSPAADVQEENLYAAVKDTQSEDRVELDSQSPHDEDPQAVTYAPVKHSSPRREMASPPS
               500       510       520       530       540       550       560

280       290                  300              310
inputs  CLGATIIIILLGLLAEDWH---------------SRKKCLQHRMRALQRPL-----PP--------LPL
         :::   ...   ......:                :.  :  :  .:   :   ::         :...
        SLSGEFLDTKDRQVEEDRQMDTEAAASEASQDVTYAQLHSLTLRRKATEPPPSQEGEPPAEPSIYATLAI
               570       580       590       600       610       620       630 inputs  A

```
            *->GesvtLtCsvsgfgppgvsvtWyfkngk.lgpsllgysysrlesgek
               G+sv  L+C+         ++v  y +  k ++         +++e +
mT268   42     GQSVILRCQGP------PDVDLY-RLEKIKP---------EKYEDQ-- 71 anlsegrfsissltLtissvekeDsGtYtCvv<-*
                         L i + e++++G Y+C
mT268   72     -----------DFLFIPTMERSNAGRYRCSY        91
```

FIG. 10A

```
            *->GesvtLtCsvsgfgppgvsvtWyfkngk.lgpsllgysysrlesgek
               G +vtL C++         ++  y k+g++ +       Y+r+e  +
mT268   128    GRDVTLKCQSP---YSFDEFVLY-KEGDtGP-------YKRPEKW-Y 162 anlsegrfsissltLtissvekeDsGtYtCvv<-*
               +            ++i++v++  sGtY+C
mT268   163    RA----------NFPIITVTAAHSGTYRCYS        183
```

FIG. 10B

```
              10        20        30        40        50        60
inputs MSPSPTALFCLGLCLGRV-PAQSGPLPKPSLQALPSSLVPLEKPVTLRCQGPPGVDLYRLEKLSSSRYQD
       :::. .:::::.: .: .:::::::::::::  ::::::: ..:::::::::::::::: . .:
       MSPASPTFFCIGLCVLQVIQTQSGPLPKPSLQAQPSSLVPLGQSVILRCQGPPDVDLYRLEKLKPEKYED
              10        20        30        40        50        60        70
          70        80        90       100       110       120       130
inputs QAVLFIPAMKRSLAGRYRCSYQNGSLWSLPSDQLELVATGVFAKPSLSAQPGPAVSSGGDVTLQCQTRYG
       :. :::::.:: :::::::::::::.:::::::::::.:::.::::::..:: :.::::: :::: :
       QDFLFIPTMERSNAGRYRCSYQNGSHWSLPSDQLELIATGVYAKPSLSAHPSSAVPQGRDVTLKCQSPYS
              80        90       100       110       120       130       140
         140       150       160       170       180       190       200
inputs FDQFALYKEGDPAPYKNPERWYRASFPIITVTAAMSGTYRCYSFSSRDPYLWSAPSDPLELVVTGTSVTP
       :: :.::::::. ::: ::::::.:::::::::.::::::::::::..:::::::::: :::::..::
       FDEFVLYKEGDTGPYKRPEKWYRANFPIITVTAAHSGTYRCYSFSSSSPYLWSAPSDPLVLVVTGLSATP
              150       160       170       180       190       200       210
         210       220       230       240       250       260       270
inputs SRLPTEPPSSVAEFSEATAELTVSFTNKVFTTETSRSITTSPKESDSPAGPARQYYTKGNLVRICLGAVI
       : :::: . :.: :  ..:     :::.:.:: :: ..:  ..:  :::: ::::::::::::::.:
       SQVPTEESFPVTESSRRPSILP---TNKISTTEKPMNITASPEGLSPPIGFAHQHYAKGNLVRICLGATI
              220       230       240       250       260       270
         280       290       300       310       320       330
inputs LIILAGFLAEDWHSRRKRLRHRGRAVQRPLPPLPPLPQTRKSHGGQDGGRQDVHSRGLCS
       :::: ..:::::::::.: : ::..:::::::::
       IIILLGLLAEDWHSRKKCLQHRMRALQRPLPPLP-LA-----------------------
              280       290       300       310
```

FIG.11

# GLYCOPROTEIN VI AND USES THEREOF

This application is a continuation of U.S. patent application Ser. No. 11/447,460, filed on Jun. 6, 2006, now abandoned; which is a divisional of U.S. patent application Ser. No. 09/503,387, filed Feb. 14, 2000, now U.S. Pat. No. 7,291,714; which is a continuation-in-part of U.S. patent application Ser. No. 09/454,824, filed Dec. 6, 1999, now abandoned; which is a continuation-in-part of U.S. patent application Ser. No. 09/345,468, filed Jun. 30, 1999, now U.S. Pat. No. 6,245,527. The entire contents of each of these applications are hereby incorporated by reference.

BACKGROUND OF THE INVENTION

The interaction between collagen and platelets is the first event of the normal hemostatic response to injury. Collagen is the major extracellular matrix protein present in the subendothelium of blood vessels. Upon damage to the endothelium lining, as a consequence of injury to the vessel wall, collagen fibers, fibrous collagen I and III are exposed to platelets. This interaction leads to platelet adhesion, activation with a second phase of adhesion, secretion occurrence, and ultimately aggregation and development of a hemostatic plug (Kehrel et al., 1998, *Blood* 91:491-9).

The mechanism of collagen-platelet interactions is complex. It involves, on one hand, direct binding of collagen to specific platelet receptors (e.g., $\alpha_2\beta_1$ integrin, collagen receptor, glycoprotein IV, and glycoprotein VI) and, on the other hand, indirect binding of collagen via bridging proteins (e.g., von Willebrand Factor (vWF)) that bind to both collagen and membrane receptors on platelets. Recent reports support a two-step mechanism of collagen-platelet interaction, consisting a platelet adhesion followed by platelet activation (Verkleij et al., 1998, *Blood* 91:3808-16). The first step involves the binding of collagen-bound vWF by the platelet receptor complex glycoprotein Ib/IX/V, followed by the direct binding of integrin $\alpha_2\beta_1$ to collagen (Moroi et al., 1997, *Thrombosis and Haemostasis* 78:439-444 and Barnes et al., 1998, *Current Opinion in Hematology* 6:314-320). This step results in platelets adhering to the subendothelium of blood vessels under physiological conditions. The second step of collagen-platelet interaction involves another platelet collagen receptor, glycoprotein VI (Barnes et al., 1998, *Current Opinion in Hematology* 6:314-320). This binding leads to strengthening of attachment and platelet activation. It is believed that glycoprotein VI (GPVI) has a minor importance in the first step of adhesion but plays a major role in the second step of collagen-platelet interaction resulting in full platelet activation and consequently the formation of the platelet aggregates (Aria et al., 1995, *British J. of Haematology* 89:124-130).

Glycoprotein VI

Glycoprotein VI (GPVI) is a platelet membrane glycoprotein that is involved in platelet-collagen interactions. In particular, GPVI is a transmembrane collagen receptor expressed on the surface of platelets. GPVI has an apparent molecular mass of 58 kDa in its non-reduced form and 62 kDa after disulfide bond reduction as determined by its migration via SDS-PAGE. Treatment of platelets with N-glycanase has been shown to result in a faster migration of GPVI in SDS-PAGE by two kDa, which probably corresponds to only one N-glycosylation site.

The existence of a 62 kDa protein, later identified as GPVI, was first detected as an antigen recognized by the sera of a patient with steroid-responsive immune thrombocytopenic purpura associated with defective collagen-induced platelet functions (Sugiyama et al., 1987, *Blood* 69: 1712-1720). The patient's plasma, as well as a preparation of full length IgG antibodies, induced irreversible aggregation and ATP release in normal platelet-rich plasma. However, Fab fragments prepared from the serum of this patient blocked platelet aggregation induced by collagen (Sugiyama et al., 1987, *Blood* 69: 1712-172).

The importance of GPVI in platelet/collagen interactions was further confirmed by comparing the expression of platelet collagen receptors from a different patient, with a mild bleeding disorder, to that of a normal individual (Moroi et al., 1989, *J. Clin. Invest.* 84(5):1440-5). The patient's platelets lacked collagen-induced aggregation and adhesion, but retained normal aggregation and release by other agonists. The expression of a 61 kDa membrane glycoprotein was detected on non-reduced, two-dimensional SDS-PAGE, but was reduced compared to the expression levels found in a normal individual. This glycoprotein was termed glycoprotein VI (GPVI). The patient's platelets did not bind to types I and III collagen fibrils suggesting that GPVI functions as a collagen receptor involved in collagen-induced platelet activation and aggregation.

GPVI has been shown to be constitutively associated with the Fc receptor gamma (FcR$\gamma$), and FcR$\gamma$ expression is lacking in GPVI-deficient platelets, suggesting that GPVI and FcR$\gamma$ are co-expressed in platelets (Tsuji et al., 1997, *J. Biol. Chem.* 272:23528-31). Further, cross-linking of GPVI by F(ab')2 fragments of anti-GPVI IgG has been shown to result in the tyrosine phosphorylation of the FcR$\gamma$-chain. FcR$\gamma$ is tyrosine-phosphorylated upon platelet activation by collagen, collagen related peptide (CRP; Gibbins et al., 1997, *FEBS Lett.* 413:255-259) or the snake venom component convulxin that acts as a platelet agonist (Cvx; Lagrue et al., 1999, *FEBS Letts.* 448:95-100). Phosphorylation occurs on the immunoreceptor tyrosine-based activation motifs (ITAM) of FcR$\gamma$ by kinases of the Src family (p59Fyn and p53/56 lyn) (Briddon S J and Watson, 1999, *Biochem J.* 338:203-9). Phosphorylation of FcR$\gamma$ allows Syk, a signaling molecule, to bind and to be in turn phosphorylated and to activate phospholipase C$\gamma$2 (PLC$\gamma$2). Further, platelet stimulation by collagen or Cvx have been shown to involve the association of phosphatidylinositol 3-kinase (PI3 kinase) and the adapter protein linker for activator of T cells (LAT) to the FcR$\gamma$ (Carlsson et al., 1998, *Blood* 92:1526-31). Thus, FcR$\gamma$ appears to interact with GPVI to effect signaling.

The results from the GPVI signal transduction pathway activation studies performed suggest that strong similarities exist between the GPVI signaling pathway in platelets and the one used by receptors for immune complexes, such as the high-affinity and low affinity receptors for IgG (FcR$\gamma$I and FcR$\gamma$III), the high-affinity receptor for IgE (FcR$\epsilon$I) and the receptor for IgA (FcR$\alpha$I) (Maliszewski et al., 1990, *J. Exp. Med.* 172:1665-72). These receptors also signal via the FcR$\gamma$ chain and Syk. Expression of the FcR$\gamma$I, FcR$\gamma$III has not been reported in platelets. The FcR$\gamma$IIa seems to be the only IgG Fc-receptor consistently expressed on platelets, and it contains one ITAM. This receptor has been suggested to be involved in thrombocytopenia and thromboembolic complications of heparin-induced thrombocytopenia (HIT), the most common drug-induced immune thrombocytopenia (Carlsson et al., 1998, *Blood* 92:1526-31) and may also be involved in other immune thrombocytopenia such as immune thrombocytopenia purpura (Loscalzo, J., and Schafer, A. I., 1998, *Thrombosis and Hemorrhage*, J. Loscalzo and A. I. Schafer, eds., Baltimore: Williams and Wilkins).

Since its detection, the function of GPVI in platelet-collagen interactions and the signal transduction pathway induced by GPVI has been studied. However, the molecular cloning of GPVI has been elusive due, at least in part, to its extensive O-linked glycosylation. The inability to clone GPVI has limited the experiments that can be performed to better understand the role of GPVI in collagen-induced platelet activation and aggregation. Further, the development of treatments for disorders, such as bleeding disorders, resulting from mutations in GPVI or its promoter, have been hindered by the lack of knowledge about the nucleic acid and amino acid sequences of GPVI.

SUMMARY OF THE INVENTION

The present invention is based, at least in part, on the discovery of cDNA molecules which encode the TANGO 268 proteins, all of which are transmembrane proteins.

In particular, TANGO 268 represents the platelet-expressed collagen receptor GPVI. This conclusion is based, at least in part, on the following evidence: (1) the glycosylated molecular weights of TANGO 268 and GPVI are identical or similar; (2) TANGO 268 and GPVI are both recognized by anti-GPVI antibodies and bind to Cvx; (3) TANGO 268 and GPVI are both preferentially expressed in the megakaryocytic cells; (4) TANGO 268 and GPVI are both predicted to have a single N-glycosylation site; (5) the molecular mass of the 40 kDa unglycosylated TANGO 268 is predicted to be approximately 62 kDa, the apparent molecular mass of GPVI, upon N- and O-linked glycosylation; (6) the presence of two immunoglobulin-like domains in TANGO 268 indicates that, like GPVI TANGO 268 interacts with the FcRγ; (7) the absence of a large intracytoplasmic tail, suggesting that this membrane-bound glycoprotein has no signaling role but associates with another member of the Ig family (e.g., FcRγ) protein to transduce a signal; and (8) the presence of a charged residue (arginine) in the transmembrane domain of TANGO 268 which is predicted to be present in GPVI based on its association with the FcRγ.

The TANGO 268 proteins are members of the Ig superfamily. The TANGO 268 proteins, fragments, derivatives, and variants thereof are collectively referred to herein as "polypeptides of the invention" or "proteins of the invention." Nucleic acid molecules encoding the polypeptides or proteins of the invention are collectively referred to as "nucleic acids of the invention."

The nucleic acids and polypeptides of the present invention are useful as modulating agents in regulating a variety of cellular processes. Accordingly, in one aspect, this invention provides isolated nucleic acid molecules encoding a polypeptide of the invention or a biologically active portion thereof. The present invention also provides nucleic acid molecules which are suitable for use as primers or hybridization probes for the detection of nucleic acids encoding a polypeptide of the invention.

The invention features nucleic acid molecules which are at least 50%, 55%, 65%, 75%, 85%, 95%, or 98% identical to the nucleotide sequence of SEQ ID NO:1 the nucleotide sequence of the cDNA insert of an EpthEa11d1 clone deposited with ATCC as Accession Number 207180, or a complement thereof.

The invention features nucleic acid molecules which are at least 40%, 45%, 50%, 55%, 65%, 75%, 85%, 95%, or 98% identical to the nucleotide sequence of SEQ ID NO:2 the nucleotide sequence of the cDNA insert of an EpthEa11d1 clone deposited with ATCC as Accession Number 207180, or a complement thereof.

The invention features nucleic acid molecules which are at least 40%, 45%, 50%, 55%, 65%, 75%, 85%, 95%, or 98% identical to the nucleotide sequence of SEQ ID NO:14 the nucleotide sequence of the cDNA insert of an EpTm268 clone deposited with ATCC as PTA-225, or a complement thereof.

The invention features nucleic acid molecules which are at least 35%, 40%, 45%, 50%, 55%, 65%, 75%, 85%, 95%, or 98% identical to the nucleotide sequence of SEQ ID NO:15 the nucleotide sequence of the cDNA insert of an EpTm268 clone deposited with ATCC as PTA-225, or a complement thereof.

The invention features nucleic acid molecules which include a fragment of at least 550, 600, 700, 800, 900, 1000, 1100, 1200, 1300, 1400, 1500, 1600, 1700, 1800, 1900 or 2000 nucleotides of the nucleotide sequence of SEQ ID NO:1 the nucleotide sequence of an EpthEa11d1 cDNA of ATCC Accession Number 207180, or a complement thereof.

The invention features nucleic acid molecules which include a fragment of at least 50, 100, 200, 300, 400, 500, 600, 700, 800, 900, 950 or 1000 nucleotides of the nucleotide sequence of SEQ ID NO:2, or a complement thereof.

The invention features nucleic acid molecules which include a fragment of at least 50, 100, 200, 300, 400, 500, 600, 700, 800, 900, 1000 or 1100 nucleotides of the nucleotide sequence of SEQ ID NO:14 the nucleotide sequence of an EpTm268 cDNA of ATCC PTA-225, or a complement thereof.

The invention features nucleic acid molecules which include a fragment of at least 50, 100, 200, 300, 400, 500, 600, 700, 800, 900, 950 or 1000 nucleotides of the nucleotide sequence of SEQ ID NO:15, or a complement thereof.

The invention also features nucleic acid molecules which include a nucleotide sequence encoding a protein having an amino acid sequence that is at least 30%, 35%, 40%, 45%, 50%, 55%, 60%, 65%, 75%, 85%, 95%, or 98% identical to the amino acid sequence of SEQ ID NO:3, the amino acid sequence encoded by an EpthEa11d1 cDNA of ATCC Accession Number 207180, or a complement thereof.

The invention also features nucleic acid molecules which include a nucleotide sequence encoding a protein having an amino acid sequence that is at least 30%, 35%, 40%, 45%, 50%, 55%, 60%, 65%, 75%, 85%, 95%, or 98% identical to the amino acid sequence of SEQ ID NO:16, the amino acid sequence encoded by an EpTm268 cDNA of ATCC PTA-225, or a complement thereof.

The invention also features nucleic acid molecules which include a nucleotide sequence encoding a protein having an amino acid sequence that is at least 30%, 35%, 40%, 45%, 50%, 55%, 60%, 65%, 75%, 85%, 95%, or 98% identical to the amino acid sequence of SEQ ID NO:3 or 16, the amino acid sequence encoded by EpthEa11d1 or EpTm268 of ATCC Accession Number 207180 or PTA-225, or a complement thereof, wherein the protein encoded by the nucleotide sequence also exhibits at least one structural and/or functional feature of a polypeptide of the invention.

In preferred embodiments, the nucleic acid molecules have the nucleotide sequence of SEQ ID NO:1, 2, 14, 15 or the nucleotide sequence of the cDNA clones of ATCC Accession Number 207180 or PTA-225.

The invention also includes nucleic acid molecules which encode a fragment of a polypeptide having the amino acid sequence of SEQ ID NO:3, or a fragment including at least 15, 25, 30, 50, 75, 100, 125, 150, 175, 200, 225, 250, 275, 300, 315 or 330 contiguous amino acids of SEQ ID NO:3, or the amino acid sequence encoded by an EpthEa11d1 cDNA of ATCC Accession Number 207180.

The invention also includes nucleic acid molecules which encode a fragment of a polypeptide having the amino acid sequence of SEQ ID NO:16, or a fragment including at least 15, 25, 30, 50, 75, 100, 125, 150, 175, 200, 225, 250, 275 or 300 contiguous amino acids of SEQ ID NO:16, or the amino acid sequence encoded by an EpTm268 cDNA of ATCC PTA-225.

The invention also includes nucleic acid molecules which encode a naturally occurring allelic variant of a polypeptide comprising the amino acid sequence of SEQ ID NO:3 or 16, or the amino acid sequence encoded by a cDNA of ATCC Accession Number 207180 or PTA-225, wherein the nucleic acid molecule hybridizes to a nucleic acid molecule consisting of a nucleic acid sequence encoding SEQ ID NO:3 or 16, or the amino acid sequence encoded by a cDNA of ATCC Accession Number 207180 or PTA-225, or a complement thereof under stringent conditions.

The invention also includes isolated polypeptides or proteins having an amino acid sequence that is at least about 30%, preferably 35%, 45%, 55%, 65%, 75%, 85%, 95%, or 98% identical to the amino acid sequence of SEQ ID NO:3, or the amino acid sequence encoded by an EpthEa11d1 cDNA of ATCC Accession Number 207180.

The invention also includes isolated polypeptides or proteins having an amino acid sequence that is at least about 30%, preferably 35%, 40%, 45%, 50%, 55%, 65%, 75%, 85%, 95%, or 98% identical to the amino acid sequence of SEQ ID NO:16, or the amino acid sequence encoded by an EpTm268 cDNA of ATCC PTA-225.

The invention also features nucleic acid molecules which encode a polypeptide fragment of at least 15, 25, 30, 50, 75, 100, 125, 150, 175, 200 or more contiguous amino acids of SEQ ID NO:3 or 16, or the amino acid sequence encoded by EpthEa11d1 or EpTm268 of ATCC Accession Number 207180 or PTA-225, respectively, wherein the fragment also exhibits at least one structural and/or functional feature of a polypeptide of the invention.

The invention also features isolated polypeptides or proteins having an amino acid sequence that is at least about 30%, preferably 35%, 40%, 45%, 50%, 55%, 65%, 75%, 85%, 95% or 98% identical to the amino acid sequence of SEQ ID NO:3 or 16, or the amino acid sequence encoded by EpthEa11a1 or EpTm268 of Accession Number 207180 or PTA-225, respectively, wherein the protein or polypeptides also exhibit at least one structural and/or functional feature of a polypeptide of the invention.

The invention also includes isolated polypeptides or proteins which are encoded by a nucleic acid molecule having a nucleotide sequence that is at least about 50%, preferably 55%, 60%, 65%, 75%, 85%, 95% or 98% identical to the nucleic acid sequence encoding SEQ ID NO:3, and isolated polypeptides or proteins which are encoded by a nucleic acid molecule having a nucleotide sequence which hybridizes under stringent hybridization conditions to a nucleic acid molecule having the nucleotide sequence of SEQ ID NO:1 or 2, a complement thereof, or the non-coding strand of an EpthEa11d1 cDNA of ATCC Accession Number 207180.

The invention also includes isolated polypeptides or proteins which are encoded by a nucleic acid molecule having a nucleotide sequence that is at least about 35%, preferably 40%, 45%, 50%, 55%, 60%, 65%, 75%, 85%, 95% or 98% identical to the nucleic acid sequence encoding SEQ ID NO:16, and isolated polypeptides or proteins which are encoded by a nucleic acid molecule having a nucleotide sequence which hybridizes under stringent hybridization conditions to a nucleic acid molecule having the nucleotide sequence of SEQ ID NO:14 or 15, a complement thereof, or the non-coding strand of an EpTm268 cDNA of ATCC PTA-225.

The invention also features isolated polypeptides or proteins which are encoded by a nucleic acid molecule having a nucleotide sequence that is at least about 30%, preferably 35%, 40%, 45%, 50%, 55%, 60%, 65%, 75%, 85%, 95% or 98% identical to a nucleic acid sequence encoding SEQ ID NO:3 or 16, isolated polypeptides or proteins which are encoded by a nucleic acid molecule having a nucleotide sequence which hybridizes under stringent hybridization conditions to a nucleic acid molecule having the nucleotide sequence of SEQ ID NO:1, 2, 14 or 15, a complement thereof, or the non-coding strand of EpthEa11d1 or EpTm268 of ATCC Accession Number 207180 or PTA-225, respectively, wherein the polypeptides or proteins also exhibit at least one structural and/or functional feature of a polypeptide of the invention.

The invention also includes polypeptides which are naturally occurring allelic variants of a polypeptide that includes the amino acid sequence of SEQ ID NO:3 or 16, or the amino acid sequence encoded by a cDNA of ATCC Accession Number 207180, wherein the polypeptide is encoded by a nucleic acid molecule which hybridizes to a nucleic acid molecule having the sequence of SEQ ID NO:1, 2, 14, 15, or a complement thereof under stringent conditions.

The invention also features nucleic acid molecules that hybridize under stringent conditions to a nucleic acid molecule having the nucleotide sequence of SEQ ID NO:1 or 2, an EpthEa11d1 cDNA of ATCC Accession Number 207180, or a complement thereof. In other embodiments, the nucleic acid molecules are at least 480, 500, 530, 550, 600, 700, 800, 900, 1000, 1100, 1200, 1300, 1400, 1500, 1600, 1700, 1800, 1900 or 2000 nucleotides in length and hybridize under stringent conditions to a nucleic acid molecule comprising the nucleotide sequence of SEQ ID NO:1, an EpthEa11d1 cDNA of ATCC Accession Number 207180, or a complement thereof.

The invention also features nucleic acid molecules that hybridize under stringent conditions to a nucleic acid molecule having the nucleotide sequence of SEQ ID NO:14 or 15, an EpTm268 cDNA of ATCC PTA-225, or a complement thereof. In other embodiments, the nucleic acid molecules are at least 400, 450, 500, 530, 550, 600, 700, 800, 900, 1000, 1100 or 1150 nucleotides in length and hybridize under stringent conditions to a nucleic acid molecule comprising the nucleotide sequence of SEQ ID NO:14, an EpTm268 cDNA of ATCC PTA-225, or a complement thereof.

The invention also features nucleic acid molecules that hybridize under stringent conditions to a nucleic acid molecule having the nucleotide sequence of SEQ ID NO:1, 2, 14 or 15, or a nucleotide sequence of EpthEa11d1 or EpTm268 of ATCC Accession Number 207180 or PTA-225, or complement thereof, wherein such nucleic acid molecules encode polypeptides or proteins that exhibit at least one structural and/or functional feature of a polypeptide of the invention.

In one embodiment, the invention provides an isolated nucleic acid molecule which is antisense to the coding strand of a nucleic acid of the invention.

Another aspect of the invention provides vectors, e.g., recombinant expression vectors, comprising a nucleic acid molecule of the invention. In another embodiment, the invention provides host cells containing such a vector or engineered to contain and/or express a nucleic acid molecule of the invention. The invention also provides methods for producing a polypeptide of the invention by culturing, in a suitable medium, a host cell of the invention such that a polypeptide of the invention is produced.

Another aspect of this invention features isolated or recombinant proteins and polypeptides of the invention. Preferred proteins and polypeptides possess at least one biological activity possessed by the corresponding naturally-occurring human polypeptide. An activity, a biological activity, or a functional activity of a polypeptide or nucleic acid of the invention refers to an activity exerted by a protein, polypeptide or nucleic acid molecule of the invention on a responsive cell as determined in vivo or in vitro, according to standard techniques. Such activities can be a direct activity, such as an association with or an enzymatic activity on a second protein, or an indirect activity, such as a cellular signaling activity mediated by interaction of the protein with a second protein.

For TANGO 268, biological activities include, e.g., (1) the ability to modulate, e.g., stabilize, promote, inhibit or disrupt protein-protein interactions (e.g., homophilic and/or heterophilic), and protein-ligand interactions, e.g., in receptor-ligand recognition; (2) the ability to modulate cell-cell interactions and/or cell-extracellular matrix (ECM) interactions, e.g., by modulating platelet interactions with subendothelial components, e.g., collagen, integrins and other ECM proteins; (3) the ability to modulate the host immune response, e.g., by modulating one or more elements in the inflammatory response; (4) the ability to modulate the proliferation, differentiation and/or activity of megakaryocytes and/or platelets; (5) the ability to modulate intracellular signaling cascades (e.g., signal transduction cascades); (6) the ability to modulate immunoregulatory functions; (7) the ability to modulate platelet morphology, migration, aggregation, degranulation and/or function; (8) the ability to interact with (e.g., bind to directly or indirectly, for example, as part of a complex comprising TANGO 268) one or more collagen molecules; (9) the ability to modulate collagen binding to platelets; (9) the ability to mediate and/or modulate intracellular $Ca^{2+}$ levels, metabolism and/or turnover of phosphatidylinositides, and phosphorylation of proteins (e.g., c-Src, Syk, PLC$\gamma$2 and/or FcR$\gamma$) via, for example, their tyrosine residues; (10) the ability mediate and/or modulate collagen-induced platelet adhesion and aggregation (e.g., thrombus formation), for example, in mediating and/or modulating secretion of the contents of platelet granules; (11) the ability mediate and/or modulate platelet adhesion and aggregation; (12) the ability to interact with (e.g., bind to directly or indirectly, for example, as part of a complex comprising TANGO 268) convulxin; (13) the ability to bind to an antibody from a patient with idiopathic thrombocytopenic purpura (ITP); (14) the ability to associate and/or co-express with FcR$\gamma$, e.g., FcR$\gamma$ in platelets; (15) the ability to induce and/or modulate tumor formation, tumor cell migration, and/or tumor cell metastasis; and (16) the ability to induce and/or modulate coronary diseases (e.g., atherosclerosis).

In one embodiment, a polypeptide of the invention has an amino acid sequence sufficiently identical to an identified domain of a polypeptide of the invention. As used herein, the term "sufficiently identical" refers to a first amino acid or nucleotide sequence which contains a sufficient or minimum number of identical or equivalent (e.g., with a similar side chain) amino acid residues or nucleotides to a second amino acid or nucleotide sequence such that the first and second amino acid or nucleotide sequences have or encode a common structural domain and/or common functional activity. For example, amino acid or nucleotide sequences which contain or encode a common structural domain having about 60% identity, preferably 65% identity, more preferably 75%, 85%, 95%, 98% or more identity are defined herein as sufficiently identical.

In one embodiment a 268 protein includes at least one or more of the following domains: a signal sequence, an extracellular domain, an immunoglobulin-like domain, a transmembrane domain, and an intracellular domain.

The polypeptides of the present invention, or biologically active portions thereof, can be operably linked to a heterologous amino acid sequence to form fusion proteins. The invention further features antibodies, such as monoclonal or polyclonal antibodies, that specifically bind a polypeptide of the invention. In addition, the polypeptides of the invention or biologically active portions thereof can be incorporated into pharmaceutical compositions, which optionally include pharmaceutically acceptable carriers.

In another aspect, the present invention provides methods for detecting the presence, activity or expression of a polypeptide of the invention in a biological sample by contacting the biological sample with an agent capable of detecting an indicator of the presence, activity or expression such that the presence activity or expression of a polypeptide of the invention in the biological sample.

In another aspect, the invention provides methods for modulating activity of a polypeptide of the invention comprising contacting a cell with an agent that modulates (inhibits or stimulates) the activity or expression of a polypeptide of the invention such that activity or expression in the cell is modulated. In one embodiment, the agent is an antibody that specifically binds to a polypeptide of the invention.

In another embodiment, the agent modulates expression of a polypeptide of the invention by modulating transcription, splicing, or translation of an mRNA encoding a polypeptide of the invention. In yet another embodiment, the agent is a nucleic acid molecule having a nucleotide sequence that is antisense to the coding strand of an mRNA encoding a polypeptide of the invention.

In yet a further aspect, the invention provides substantially purified antibodies or fragment thereof, and non-human antibodies or fragments thereof, which antibodies or fragments specifically bind to a polypeptide comprising an amino acid sequence selected from the group consisting of: the amino acid sequence of SEQ ID NO:3 or 16, or the amino acid sequence encoded by the cDNA insert of the plasmid deposited with ATCC as Accession Number 207180, or the amino acid sequence encoded by the cDNA insert of the plasmid deposited with ATCC as PTA-225; a fragment of at least 15 amino acid residues of the amino acid sequence of SEQ ID NO:3 or 16; an amino acid sequence which is at least 95% identical to the amino acid sequence of SEQ ID NO:3 or 16, wherein the percent identity is determined using the ALIGN program of the GCG software package with a PAM120 weight residue table, a gap length penalty of 12, and a gap penalty of 4; and an amino acid sequence which is encoded by a nucleic acid molecule which hybridizes to the nucleic acid molecule consisting of SEQ ID NO:1, 2, 14, or 15 under conditions of hybridization of 6×SSC at 45° C. and washing in 0.2×SSC, 0.1% SDS at 65° C. In various embodiments, the substantially purified antibodies of the invention, or fragments thereof, can be human, non-human, chimeric and/or humanized antibodies.

In another aspect, the invention provides non-human antibodies or fragments thereof, which antibodies or fragments specifically bind to a polypeptide comprising an amino acid sequence selected from the group consisting of: the amino acid sequence of SEQ ID NO:3 or 16, or the amino acid sequence encoded by the cDNA insert of the plasmid deposited with ATCC as Accession Number 207180, or the amino acid sequence encoded by the cDNA insert of the plasmid deposited with ATCC as PTA-225; a fragment of at least 15 amino acid residues of the amino acid sequence of SEQ ID NO:3 or 16; an amino acid sequence which is at least 95% identical to the amino acid sequence of SEQ ID NO:3 or 16, wherein the percent identity is determined using the ALIGN program of the GCG software package with a PAM120 weight residue table, a gap length penalty of 12, and a gap penalty of 4; and an amino acid sequence which is encoded by a nucleic acid molecule which hybridizes to the nucleic acid molecule consisting of SEQ ID NO:1, 2, 14, or 15 under conditions of hybridization of 6×SSC at 45° C. and washing in 0.2×SSC, 0.1% SDS at 65° C. Such non-human antibodies can be goat, mouse, sheep, horse, chicken, rabbit, or rat antibodies. Alternatively, the non-human antibodies of the invention can be chimeric and/or humanized antibodies. In addition, the non-human antibodies of the invention can be polyclonal antibodies or monoclonal antibodies.

In still a further aspect, the invention provides monoclonal antibodies or fragments thereof, which antibodies or fragments specifically bind to a polypeptide comprising an amino acid sequence selected from the group consisting of: the amino acid sequence of SEQ ID NO:3 or 16, or the amino acid sequence encoded by the cDNA insert of the plasmid deposited with ATCC as Accession Number 207180, or the amino acid sequence encoded by the cDNA insert of the plasmid deposited with ATCC as PTA-225; a fragment of at least 15 amino acid residues of the amino acid sequence of SEQ ID NO:3 or 16; an amino acid sequence which is at least 95% identical to the amino acid sequence of SEQ ID NO:3 or 16, wherein the percent identity is determined using the ALIGN program of the GCG software package with a PAM120 weight residue table, a gap length penalty of 12, and a gap penalty of 4; and an amino acid sequence which is encoded by a nucleic acid molecule which hybridizes to the nucleic acid molecule consisting of SEQ ID NO:1, 2, 14, or 15 under conditions of hybridization of 6×SSC at 45° C. and washing in 0.2×SSC, 0.1% SDS at 65° C. The monoclonal antibodies can be human, humanized, chimeric and/or non-human antibodies.

In a particularly preferred embodiment, the substantially purified antibodies or fragments thereof, the non-human antibodies or fragments thereof, and/or the monoclonal antibodies or fragments thereof, of the invention specifically bind to an extracellular domain of the amino acid sequence of SEQ ID NO:3 or 16. Preferably, the extracellular domain to which the antibody, or fragment thereof, binds comprises amino acid residues 21 to 269 of SEQ ID NO:3 or amino acid residues 22 to 267 of SEQ ID NO:16. In an alternative embodiment, the extracellular domain to which the substantially purified antibody binds comprises an immunoglobulin-like domain. In one aspect, such an immunoglobulin-like domain comprises amino acid residues 48 to 88 or 134 to 180 of SEQ ID NO:3 or amino acid residues 49 to 89 or 135 to 181 of SEQ ID NO:16.

Any of the antibodies of the invention can be conjugated to a therapeutic moiety or to a detectable substance. Non-limiting examples of detectable substances that can be conjugated to the antibodies of the invention are an enzyme, a prosthetic group, a fluorescent material, a luminescent material, a bioluminescent material, and a radioactive material.

The invention also provides a kit containing an antibody of the invention conjugated to a detectable substance, and instructions for use. Still another aspect of the invention is a pharmaceutical composition comprising an antibody of the invention and a pharmaceutically acceptable carrier. In preferred embodiments, the pharmaceutical composition contains an antibody of the invention, a therapeutic moiety, and a pharmaceutically acceptable carrier.

Still another aspect of the invention is a method of making an antibody that specifically recognizes GPVI, the method comprising immunizing a mammal with a polypeptide. The polypeptide used as an immungen comprises an amino acid sequence selected from the group consisting of: the amino acid sequence of SEQ ID NO:3 or 16, or the amino acid sequence encoded by the cDNA insert of the plasmid deposited with ATCC as Accession Number 207180, or the amino acid sequence encoded by the cDNA insert of the plasmid deposited with ATCC as PTA-225; a fragment of at least 15 amino acid residues of the amino acid sequence of SEQ ID NO:3 or 16; an amino acid sequence which is at least 95% identical to the amino acid sequence of SEQ ID NO:3 or 16, wherein the percent identity is determined using the ALIGN program of the GCG software package with a PAM120 weight residue table, a gap length penalty of 12, and a gap penalty of 4; and an amino acid sequence which is encoded by a nucleic acid molecule which hybridizes to the nucleic acid molecule consisting of SEQ ID NO:1, 2, 14, or 15 under conditions of hybridization of 6×SSC at 45° C. and washing in 0.2×SSC, 0.1% SDS at 65° C. After immunization, a sample is collected from the mammal that contains an antibody that specifically recognizes GPVI. Preferably, the polypeptide is recombinantly produced using a non-human host cell. Optionally, the antibodies can be further purified from the sample using techniques well known to those of skill in the art. The method can further comprise producing a monoclonal antibody-producing cell from the cells of the mammal. Optionally, antibodies are collected from the antibody-producing cell.

The present invention also provides methods to treat a subject having a disorder characterized by aberrant activity of a polypeptide of the invention or aberrant expression of a nucleic acid of the invention by administering an agent which is a modulator of the activity of a polypeptide of the invention or a modulator of the expression of a nucleic acid of the invention to the subject. In one embodiment, the modulator is a protein of the invention. In another embodiment, the modulator is a nucleic acid of the invention. In other embodiments, the modulator is a peptide, peptidomimetic, or other small molecule.

The present invention also provides diagnostic assays for identifying the presence or absence of a genetic lesion or mutation characterized by at least one of: (i) aberrant modification or mutation of a gene encoding a polypeptide of the invention, (ii) mis-regulation of a gene encoding a polypeptide of the invention, and (iii) aberrant post-translational modification of the invention wherein a wild-type form of the gene encodes a protein having the activity of the polypeptide of the invention.

In another aspect, the invention provides a method for identifying a compound that binds to or modulates the activity of a polypeptide of the invention. In general, such methods entail measuring a biological activity of the polypeptide in the presence and absence of a test compound and identifying those compounds which alter the activity of the polypeptide.

The invention also features methods for identifying a compound which modulates the expression of a polypeptide or nucleic acid of the invention by measuring the expression of the polypeptide or nucleic acid in the presence and absence of the compound.

Other features and advantages of the invention will be apparent from the following detailed description and claims.

BRIEF DESCRIPTION OF THE DRAWINGS

FIGS. 1A-B depict the cDNA sequence of human TANGO 268 (SEQ ID NO:1) and the predicted amino acid sequence of human TANGO 268 (SEQ ID NO:3). The open reading frame of SEQ ID NO:1 extends from nucleotide 36 to nucleotide 1052 of SEQ ID NO:1 (SEQ ID NO:2).

FIG. 2 depicts a hydropathy plot of human TANGO 268. Relatively hydrophobic regions of the protein are above the dashed horizontal line, and relatively hydrophilic regions of the protein are below the dashed horizontal line. The cysteine residues (cys) are indicated by short vertical lines just below the hydropathy trace. The dashed vertical line separates the signal sequence (amino acids 1 to 20 of SEQ ID NO:3; SEQ ID NO:4) on the left from the mature protein (amino acids 21 to 339 of SEQ ID NO:3; SEQ ID NO:5) on the right. Below the hydropathy plot, the amino acid sequence of human TANGO 268 is depicted.

FIGS. 3A-C depict an alignment of the nucleotide sequence of the open reading frame for human monocyte inhibitory receptor precursor (SEQ ID NO:24; GenBank Accession Number U91928) and the nucleotide sequence of the open reading frame for human TANGO 268 (SEQ ID NO:2). The nucleotide sequences of coding regions of human monocyte inhibitory receptor precursor and human TANGO 268 are 37.7% identical. The nucleotide sequences of full-length, including the 5' and 3' untranslated regions (UTRs), human monocyte inhibitory receptor precursor SEQ ID NO:11; GenBank Accession Number U91928) and human TANGO 268 are 49.9% identical. These alignments were performed using the ALIGN alignment program with a PAM120 scoring matrix, a gap length penalty of 12, and a gap penalty of 4.

FIG. 4 depicts an alignment of the amino acid sequence of human monocyte inhibitory receptor precursor (SEQ ID NO:12) and the amino acid sequence of human TANGO 268 (SEQ ID NO:3). The amino acid sequences of human monocyte inhibitory receptor precursor and human TANGO 268 are 23.0% identical. This alignment was performed using the ALIGN alignment program with a PAM120 scoring matrix, a gap length penalty of 12, and a gap penalty of 4.

FIG. 5A depicts an alignment of the amino acid sequence of a typical immunoglobulin domain (SEQ ID NO:13; GenBank Accession Number PF00047) and amino acid residues 41 to 90 of human TANGO 268 (SEQ ID NO:3). This alignments was performed using the ALIGN alignment program with a PAM120 scoring matrix, a gap length penalty of 12, and a gap penalty of 4.

FIG. 5B depicts an alignment of the amino acid sequence of a typical immunoglobulin domain (SEQ ID NO:13; GenBank Accession Number PF00047) and amino acid residues 127 to 182 of human TANGO 268 (SEQ ID NO:3). This alignment was performed using the ALIGN alignment program with a PAM120 scoring matrix, a gap length penalty of 12, and a gap penalty of 4.

FIG. 6 depicts a cDNA sequence of mouse TANGO 268 (SEQ ID NO:14) and the predicted amino acid sequence of mouse TANGO 268 (SEQ ID NO:16). The open reading frame of SEQ ID NO:14 extends from nucleotide 63 to 1001 of SEQ ID NO:14 (SEQ ID NO:15).

FIG. 7 depicts a hydropathy plot of mouse TANGO 268. Relatively hydrophobic regions of the protein are above the dashed horizontal line, and relatively hydrophilic regions of the protein are below the dashed horizontal line. The cysteine residues (cys) are indicated by short vertical lines just below the hydropathy trace. The dashed vertical line separates the signal sequence (amino acids 1 to 21 of SEQ ID NO:16; SEQ ID NO:17) on the left from the mature protein (amino acids 22 to 313 of SEQ ID NO:16; SEQ ID NO:18) on the right. Below the hydropathy plot, the amino acid sequence of mouse TANGO 268 is depicted.

FIGS. 8A-D depict an alignment of the nucleotide sequence of the open reading frame for human monocyte inhibitory receptor precursor (SEQ ID NO:24; GenBank Accession Number U91928) and the nucleotide sequence of the open reading frame for mouse TANGO 268 (SEQ ID NO:15). The nucleotide sequences of coding regions of human monocyte inhibitory receptor precursor and mouse TANGO 268 are 34.4% identical. The nucleotide sequences of full-length, including the 5' and 3' untranslated regions (UTRs), human monocyte inhibitory receptor precursor SEQ ID NO:11; GenBank Accession Number U91928) and mouse TANGO 268 are 35.6% identical. These alignments were performed using the ALIGN alignment program with a PAM120 scoring matrix, a gap length penalty of 12, and a gap penalty of 4.

FIG. 9 depicts an alignment of the amino acid sequence of human monocyte inhibitory receptor precursor (SEQ ID NO:12) and the amino acid sequence of mouse TANGO 268 (SEQ ID NO:16). The amino acid sequences of human monocyte inhibitory receptor precursor and mouse TANGO 268 are 20.3% identical. This alignment was performed using the ALIGN alignment program with a PAM120 scoring matrix, a gap length penalty of 12, and a gap penalty of 4.

FIG. 10A depicts an alignment of the amino acid sequence of immunoglobulin domain (SEQ ID NO:12; GenBank Accession Number PF00047) and amino acid residues 42 to 91 of mouse TANGO 268 (SEQ ID NO:16). This alignment was performed using the ALIGN alignment program with a PAM120 scoring matrix, a gap length penalty of 12, and a gap penalty of 4.

FIG. 10B depicts an alignment of the amino acid sequence of a typical immunoglobulin domain (SEQ ID NO:12; GenBank Accession Number PF00047) and amino acid residues 128 to 183 of mouse TANGO 268 (SEQ ID NO:16). This alignment was performed using the ALIGN alignment program with a PAM120 scoring matrix, a gap length penalty of 12, and a gap penalty of 4.

FIG. 11 depicts an alignment of the amino acid sequence of human TANGO 268 (SEQ ID NO:3) and the amino acid sequence of mouse TANGO 268 (SEQ ID NO:16). The alignment demonstrates that the amino acid sequences of human and mouse TANGO 268 are 64.4% identical. The alignment was performed using the ALIGN program with a PAM120 scoring matrix, a gap length penalty of 12 and a gap penalty of 4. The sequences within the boxes are the signal sequences for human and mouse TANGO 268; the line above the two sequences indicates the Ig-like domains for human and mouse TANGO 268; and the arrow above the sequences points to the charged residue (arginine) in human and mouse TANGO 268.

FIG. 14: Tissue expression of hGPVI and mGPVI using RT-PCR, northern blot and ISH analysis:

FIG. 15: Binding of Cvx to murine hematopoietic cell lines
Hematopoietic cell lines were transduced with a retrovirus expressing rmGPVI. Control cells were transduced with the empty vector. Cells were incubated with FITC-coupled Cvx or FITC-coupled bothrojaracin as a control and analyzed by flow cytometry.

Lysates from GPVI transduced or control U937 cells were incubated with a polyclonal anti-FcRγ antibody and protein A-sepharose. Immunoprecipitated proteins were separated by SDS-PAGE and blotted on PVDF. Membranes were incubated with a mixture of anti-FcRγ and anti-GPVI antibodies revealed with peroxidase-coupled protein A and chemiluminescence.

Figure 18:
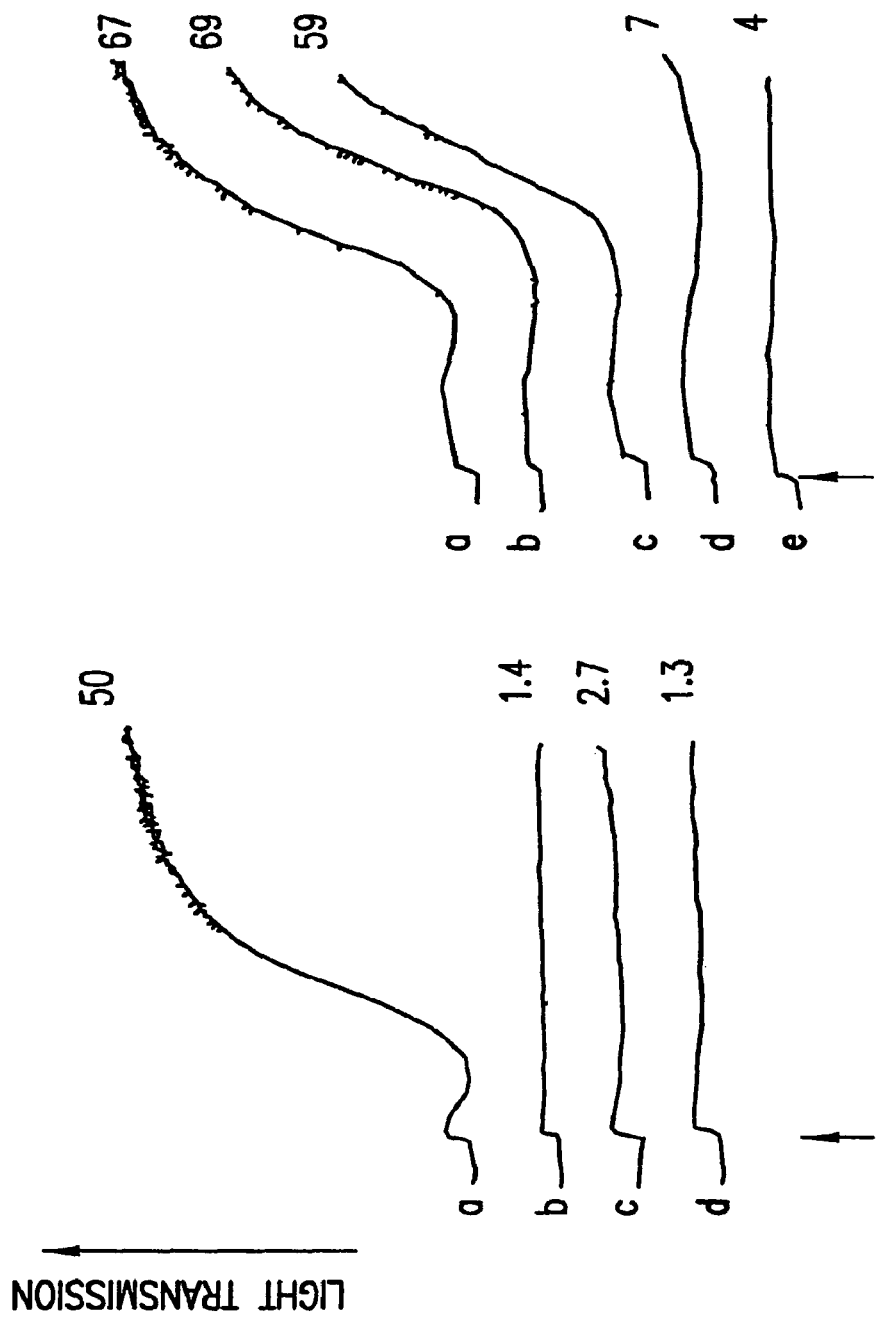

FIG. 18: Inhibition of Cvx- or collagen-induced platelet activation by recombinant human soluble GPVI:Fc.

FIG. 18A: tracing a: platelets were activated by 100 pM Cvx; tracing b: platelet suspension was incubated with 1 µg recombinant human soluble GPVI:Fc for two minutes before the addition of Cvx; tracing c and d: collagen was preincubated with 0.25 µg and 0.5 µg recombinant human soluble GPVI:Fc for two minutes respectively before addition to platelets.

FIG. 18B: tracing a: platelets were activated by collagen type I; tracing b: platelets were preincubated with 5 µg of recombinant soluble GPVI:Fc for two minutes before the addition of collagen; tracings c to e: collagen was preincubated with respectively 1 µg, 2.5 µg and 5 µg of recombinant soluble GPVI:Fc for two minutes before addition to platelets. $^{14}$C 5-HT labeled washed platelets were used. The percentage of $^{14}$C 5-HT release measured in each condition is indicated.

Figure 19:
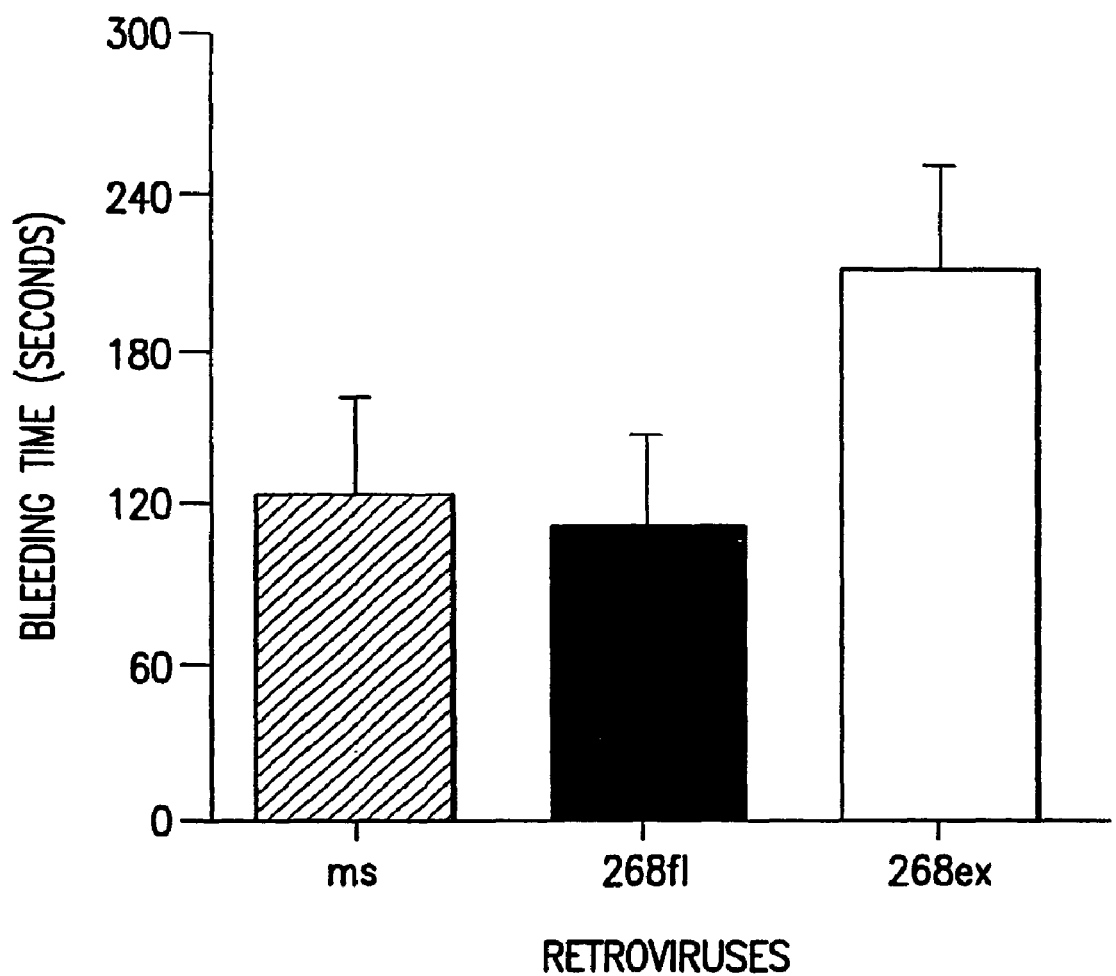

FIG. 19: Bleeding time of mice transplanted with bone marrow cells expressing GPVI. Irradiated mice transplanted with bone marrow cells expressing full length GPVI, the extracellular domain of GPVI, or a control were analyzed two months post-transplantation for the recovery time from a small tail vein incision.

DETAILED DESCRIPTION OF THE INVENTION

The TANGO 268 proteins and nucleic acid molecules comprise a family of molecules having certain conserved structural and functional features. As used herein, the term "family" is intended to mean two or more proteins or nucleic acid molecules having a common structural domain and having sufficient amino acid or nucleotide sequence identity as defined herein. Family members can be from either the same or different species. For example, a family can comprises two or more proteins of human origin, or can comprise one or more proteins of human origin and one or more of non-human origin. Members of the same family may also have common structural domains.

For example, TANGO 268 proteins of the invention have signal sequences. As used herein, a "signal sequence" includes a peptide of at least about 15 or 20 amino acid residues in length which occurs at the N-terminus of secretory and membrane-bound proteins and which contains at least about 70% hydrophobic amino acid residues such as alanine, leucine, isoleucine, phenylalanine, proline, tyrosine, tryptophan, or valine. In a preferred embodiment, a signal sequence contains at least about 10 to 40 amino acid residues, preferably about 19-34 amino acid residues, and has at least about 60-80%, more preferably 65-75%, and more preferably at least about 70% hydrophobic residues. A signal sequence serves to direct a protein containing such a sequence to a lipid bilayer. Thus, in one embodiment, a TANGO 268 protein contains a signal sequence at about amino acids 1 to 20 of SEQ ID NO:3 (SEQ ID NO:4) or at about amino acids 1 to 21 of SEQ ID NO:16 (SEQ ID NO:17). The signal sequence is cleaved during processing of the mature protein.

A TANGO 268 family member consists of one or more of the following domains: (1) an extracellular domain; (2) a transmembrane domain; and (3) a cytoplasmic domain. In one embodiment, a TANGO 268 protein contains an extracellular domain at about amino acid residues 21 to 269 of SEQ ID NO:3 (SEQ ID NO:9), a transmembrane domain at about amino acid residues 270 to 288 of SEQ ID NO:3 (SEQ ID NO:8), and a cytoplasmic domain at about amino acid residues 289 to 339 of SEQ ID NO:3 (SEQ ID NO:10). In this embodiment, the mature TANGO 268 protein corresponds to amino acids 21 to 339 of SEQ ID NO:3 (SEQ ID NO:5). In another embodiment, a TANGO 268 family contains an extracellular domain at about amino acid residues 22 to 267 of SEQ ID NO:16 (SEQ ID NO:19), a transmembrane domain at about amino acid residues 268 to 286 of SEQ ID NO:16 (SEQ ID NO:20), and a cytoplasmic domain at about amino acid residues 287 to 313 of SEQ ID NO:16 (SEQ ID NO:21). In this embodiment, the mature TANGO 268 protein corresponds to amino acids 22 to 313 of SEQ ID NO:16 (SEQ ID NO:18).

A TANGO 268 family member contains a charged residue, such as arginine, lysine, histidine, glutamic acid, and aspartic acid, in its transmembrane domain. In one embodiment, a TANGO 268 protein contains a charged amino acid residue, preferably arginine, at amino acid 272 of SEQ ID NO:3. In another embodiment, a TANGO 268 protein contains a charged amino acid residue, preferably arginine, at amino acid 270 of SEQ ID NO:16.

A TANGO 268 family member includes a signal sequence. In certain embodiment, a TANGO 268 family member has the amino acid sequence of SEQ ID NO:3, and the signal sequence is located at amino acids 1 to 18, 1 to 19, 1 to 20, 1 to 21 or 1 to 22. In an another embodiment, a TANGO 268 family member has the amino acid sequence of SEQ ID NO:16, and the signal sequence is located at amino acids 1 to 19, 1 to 20, 1 to 21, 1 to 22 or 1 to 23. In such embodiments of the invention, the extracellular domain and the mature protein resulting from cleavage of such signal peptides are also included herein. For example, the cleavage of a signal sequence consisting of amino acids 1 to 19 results in an extracellular domain consisting of amino acids 20 to 269 of SEQ ID NO:3 and the mature TANGO 268 protein corresponding to amino 20 to 339.

An Ig domain typically has the following consensus sequence, beginning about 1 to 15 amino acid residues, more preferably about 3 to 10 amino acid residues, and most preferably about 5 amino acid residues from the C-terminal end of a protein: (FY)-Xaa-C-Xaa-(VA)-COO—, wherein (FY) is either a phenylalanine or a tyrosine residue (preferably tyrosine), where "Xaa" is any amino acid, C is a cysteine residue, (VA) is either valine or an alanine residue (preferably alanine), and COO— is the protein C-terminus. An Ig-like domain as described herein has the following consensus sequence, beginning about 1 to 15 amino acid residues, more preferably about 3 to 10 amino acid residues, and most preferably about 5 amino acid residues from the domain C-terminus: (FY)-Xaa-C, wherein (FY) is either a phenylalanine or a tyrosine residue (preferably tyrosine), where "Xaa" is any amino acid, and C is a cysteine residue. In one embodiment, a TANGO 268 family member includes one or more Ig-like domains having an amino acid sequence that is at least about 55%, preferably at least about 65%, more preferably at least about 75%, yet more preferably at least about 85%, and most preferably at least about 95% identical to amino acids 48 to 88 and/or amino acids 134 to 180 of SEQ ID NO:3, which are the Ig-like domains of human TANGO 268 (these Ig-like domains are also represented as SEQ ID NO:6 and 7, respectively).

In another embodiment, a TANGO 268 family member includes one or more Ig-like domains having an amino acid sequence that is at least about 55%, preferably at least about 65%, more preferably at least about 75%, yet more preferably at least about 85%, and most preferably at least about 95% identical to amino acids 48 to 88 and/or amino acids 134 to 180 of SEQ ID NO:3, which are the Ig-like domains of human TANGO 268 (these Ig-like domains are also represented as SEQ ID NO:6 and 7, respectively), includes a conserved cysteine residue about 8 residues downstream from the N-terminus of the Ig-like domain, and has one or more Ig-like domain consensus sequences as described herein.

In another embodiment, a TANGO 268 family member includes one or more Ig-like domains having an amino acid sequence that is at least 55%, preferably at least about 65%, more preferably at least about 75%, yet more preferably at least about 85%, and most preferably at least about 95% identical to amino acids 48 to 88 and/or amino acids 134 to 180 of SEQ ID NO:3, which are the Ig-like domains of human TANGO 268 (SEQ ID NO:6 and 7, respectively), includes a conserved cysteine residue 8 residues downstream from the N-terminus of the Ig-like domain, has one or more Ig-like domain consensus sequences as described herein, and has a conserved cysteine within the consensus sequence that forms a disulfide with said first conserved cysteine.

In another embodiment, a TANGO 268 family member includes one or more Ig-like domains having an amino acid sequence that is at least 55%, preferably at least about 65%, more preferably at least about 75%, yet more preferably at least about 85%, and most preferably at least about 95% identical to amino acids 48 to 88 and/or amino acids 134 to 180 of SEQ ID NO:3, which are the Ig-like domains of human TANGO 268 (SEQ ID NO:6 and 7, respectively), includes a conserved cysteine residue 8 residues downstream from the N-terminus of the Ig-like domain, has one or more Ig-like domain consensus sequences as described herein, and has a conserved cysteine within the consensus sequence that forms a disulfide with said first conserved cysteine.

In yet another embodiment, a TANGO 268 family member includes one or more Ig-like domains having an amino acid sequence that is at least 55%, preferably at least about 65%, more preferably at least about 75%, yet more preferably at least about 85%, and most preferably at least about 95% identical to amino acids 48 to 88 and/or amino acids 134 to 180 of SEQ ID NO:3 (SEQ ID NO:6 and 7, respectively), includes a conserved cysteine residue 8 residues downstream from the N-terminus of the Ig-like domain, has one or more Ig-like domain consensus sequences described herein, has a conserved cysteine within the consensus sequence that forms a disulfide with said first conserved cysteine, and has at least one TANGO 268 biological activity as described herein.

In another embodiment, the Ig-like domain of TANGO 268 is an Ig domain, which has the following consensus sequence at the C-terminus of the domain: (FY)-Xaa-C-Xaa-(VA)-COO—, wherein (FY) is either a phenylalanine or a tyrosine residue (preferably tyrosine), where "Xaa" is any amino acid, C is a cysteine residue, (VA) is a valine or alanine residue, and COO— is the C-terminus of the domain. In this embodiment, a TANGO 268 family member includes one or more Ig-like domains having an amino acid sequence that is at least about 55%, preferably at least about 65%, more preferably at least 75%, yet more preferably at least about 85%, and most preferably at least about 95% identical to amino acids 48 to 90 and/or amino acids 134 to 182 of SEQ ID NO:3.

In another embodiment, a TANGO 268 family member includes one or more Ig-like domains having an amino acid sequence that is at least about 55%, preferably at least about 65%, more preferably at least 75%, yet more preferably at least about 85%, and most preferably at least about 95% identical to amino acids 49 to 89 and/or amino acids 135 to 181 of SEQ ID NO:16, which are the Ig-like domains of mouse TANGO 268 (these Ig-like domains are also represented SEQ ID NO:22 and 23, respectively).

In another embodiment, a TANGO 268 family member includes one or more Ig-like domains having an amino acid sequence that is at least about 55%, preferably at least about 65%, more preferably at least about 75%, yet more preferably at least about 85%, and most preferably at least about 95% identical to amino acids 49 to 89 and/or amino acids 135 to 181 of SEQ ID NO:16 (SEQ ID NO:22 and 23, respectively), includes a conserved cysteine residue about 8 residues downstream from the N-terminus of the Ig-like domain, and has one or more Ig-like domain consensus sequences as described herein.

In another embodiment, a TANGO 268 family member includes one or more Ig-like domains having an amino acid sequence that is at least 55%, preferably at least about 65%, more preferably at least about 75%, yet more preferably at least about 85%, and most preferably at least about 95% identical to amino acids 49 to 89 and/or amino acids 135 to 181 of SEQ ID NO:16 (SEQ ID NO:22 and 23, respectively), includes a conserved cysteine residue 8 residues downstream from the N-terminus of the Ig-like domain, has one or more Ig-like domain consensus sequences as described herein, and has a conserved cysteine within the consensus sequence that forms a disulfide with said first conserved cysteine.

In another embodiment, a TANGO 268 family member includes one or more Ig-like domains having an amino acid sequence that is at least 55%, preferably at least about 65%, more preferably at least about 75%, yet more preferably at least about 85%, and most preferably at least about 95% identical to amino acids 49 to 89 and/or amino acids 135 to 181 of SEQ ID NO:16 (SEQ ID NO:22 and 23, respectively), includes a conserved cysteine residue 8 residues downstream from the N-terminus of the Ig-like domain, has one or more Ig-like domain consensus sequences as described herein, and has a conserved cysteine within the consensus sequence that forms a disulfide with said first conserved cysteine.

In yet another embodiment, a TANGO 268 family member includes one or more Ig-like domains having an amino acid sequence that is at least 55%, preferably at least about 65%, more preferably at least about 75%, yet more preferably at least about 85%, and most preferably at least about 95% identical to amino acids 49 to 89 and/or amino acids 135 to 181 of SEQ ID NO:16 (SEQ ID NO:22 and 23, respectively), includes a conserved cysteine residue 8 residues downstream from the N-terminus of the Ig-like domain, has one or more Ig-like domain consensus sequences as described herein, has a conserved cysteine within the consensus sequence that forms a disulfide with said first conserved cysteine, and has at least one TANGO 268 biological activity as described herein.

In another embodiment, the Ig-like domain of TANGO 268 is an Ig domain, which has the following consensus sequence at the C-terminus end of the domain: (FY)-Xaa-C-Xaa-(VA)-COO—, wherein (FY) is either a phenylalanine or a tyrosine residue (preferably tyrosine), where "Xaa" is any amino acid, C is a cysteine residue, (VA) is a valine or alanine residue, and COO— is the C-terminus of the domain. In this embodiment, a TANGO 268 family member includes one or more Ig-like domains having an amino acid sequence that is at least about 55%, preferably at least about 65%, more preferably at least 75%, yet more preferably at least about 85%, and most preferably at least about 95% identical to amino acids 49 to 91 and/or amino acids 135 to 183 of SEQ ID NO:16, which are the Ig-like domains of mouse TANGO 268.

In a preferred embodiment, a TANGO 268 family member has the amino acid sequence of SEQ ID NO:6, wherein the aforementioned Ig-like domain conserved residues are located as follows: the N-terminal conserved cysteine residue is located at amino acid residue position 48 (within the Ig-like domain SEQ ID NO:3) and the C-terminal conserved cysteine residue is located at amino acid position 88 (within the Ig-like domain SEQ ID NO:3). In another preferred embodiment, a TANGO 268 family member has the amino acid sequence of SEQ ID NO:6, wherein the aforementioned Ig-like domain conserved residues are located as follows: the N-terminal conserved cysteine residue is located at amino acid residue position 135 (within the Ig-like domain SEQ ID NO:3) and the C-terminal conserved cysteine residue is located at amino acid position 180 (within the Ig-like domain SEQ ID NO:3). In another preferred embodiment, a TANGO 268 family member has the amino acid sequence of SEQ ID NO:22, wherein the aforementioned Ig-like domain conserved residues are located as follows: the N-terminal conserved cysteine residue is located at amino acid residue position 49 (within the Ig-like domain of SEQ ID NO:16) and the C-terminal conserved cysteine residue is located at amino acid position 89 (within the Ig-like domain of SEQ ID NO:16). In another preferred embodiment, a TANGO 268 family member has the amino acid sequence of SEQ ID NO:23, wherein the aforementioned Ig-like domain conserved residues are located as follows: the N-terminal conserved cysteine residue is located at amino acid residue position 135 (within the Ig-like domain of SEQ ID NO:16) and the C-terminal conserved cysteine residue is located at amino acid position 181 (within the Ig-like domain of SEQ ID NO:16).

Various features of human and mouse TANGO 268 are summarized below.

Human TANGO 268

A cDNA encoding human TANGO 268 was identified by analyzing the sequences of clones present in a human megakaryocyte cDNA library. This analysis led to the identification of a clone, jthea105e02, encoding full-length human TANGO 268. The human TANGO 268 cDNA of this clone is 2047 nucleotides long (FIGS. 1A-1B; SEQ ID NO:1). The open reading frame of this cDNA, nucleotides 36 to 1052 of SEQ ID NO:1 (SEQ ID NO:2), encodes a 339 amino acid transmembrane protein (FIGS. 1A-1B; SEQ ID NO:3) that, as discussed below, represents a platelet-expressed collagen receptor glycoprotein.

The signal peptide prediction program SIGNALP (Nielsen, et al., 1997, Protein Engineering 10:1-6) predicted that human TANGO 268 includes an 20 amino acid signal peptide (amino acid 1 to about amino acid 20 of SEQ ID NO:3; SEQ ID NO:4) preceding the mature human TANGO 268 protein (corresponding to about amino acid 21 to amino acid 339 of SEQ ID NO:3; SEQ ID NO:5). The molecular weight of human TANGO 268 without post-translational modifications is 36.9 kDa prior to the cleavage of the signal peptide, 34.9 kDa after cleavage of the signal peptide.

Human TANGO 268 is a transmembrane protein that is a collagen receptor expressed on platelets which consists of one or more of the following domains: (1) an extracellular domain; (2) a transmembrane domain; and (3) a cytoplasmic domain. The human TANGO 268 protein contains an extracellular domain at amino acid residues 21 to 269 of SEQ ID NO:3 (SEQ ID NO:9), a transmembrane domain at amino acid residues 270 to 288 of SEQ ID NO:3 (SEQ ID NO:8), and a cytoplasmic domain at amino acid residues 289 to 339 of SEQ ID NO:3 (SEQ ID NO:10).

FIG. 2 depicts a hydropathy plot of human TANGO 268. Relatively hydrophobic regions of the protein are shown above the horizontal line, and relatively hydrophilic regions of the protein are below the horizontal line. The cysteine residues (cys) and potential N-glycosylation sites (Ngly) are indicated by short vertical lines just below the hydropathy trace. The dashed vertical line separates the signal sequence (amino acids 1 to 20 of SEQ ID NO:3; SEQ ID NO:4) on the left from the mature protein (amino acids 21 to 339 of SEQ ID NO:3; SEQ ID NO:5) on the right.

Human TANGO 268 comprises two immunoglobulin-like domain sequences at amino acids 48 to 88 and at amino acids 134 to 180 of SEQ ID NO:3; SEQ ID NO:6 and SEQ ID NO:7. A single N-glycosylation site having the sequence NGSL is present at about amino acids 92 to 95 of SEQ ID NO:3. Nine protein kinase C phosphorylation sites are present in human TANGO 268. The first has the sequence TLR (at amino acids 45 to 47 of SEQ ID NO:3), the second has the sequence SSR (at amino acids 64 to 66 of SEQ ID NO:3), the third has the sequence TYR (at amino acids 177 to 179 of SEQ ID NO:3), the fourth has the sequence SSR (at amino acids 184 to 186 of SEQ ID NO:3), the fifth has the sequence TNK (at amino acids 235 to 237 of SEQ ID NO:3), the sixth has the sequence TSR (at amino acids 243 to 245 of SEQ ID NO:3), the seventh has the sequence SPK (at amino acids 250 to 252 of SEQ ID NO:3), the eighth has the sequence SRR (at amino acids 293 to 295 of SEQ ID NO:3), and the ninth has the sequence TRK (at amino acids 318 to 320 of SEQ ID NO:3). Four casein kinase II phosphorylation sites are present in human TANGO 268. The first has the sequence SGGD (at amino acids 126 to 129 of SEQ ID NO:3), the second has the sequence SSRD (at amino acids 184 to 187 of SEQ ID NO:3), the third has the sequence SVAE (at amino acids 219 to 222 of SEQ ID NO:3), and the fourth has the sequence SPKE (at amino acids 250 to 253 of SEQ ID NO:3). Human TANGO 268 has two tyrosine kinase phosphorylation sites having the sequences KEGDPAPY (at amino acids 147 to 154 of SEQ ID NO:3) and KNPERWY (at amino acids 155 to 161 of SEQ ID NO:3). Human TANGO 268 has five N-myristylation sites. The first has the sequence GLCLGR (at amino acids 12 to 17 of SEQ ID NO:3), the second has the sequence GSLWSL (at amino acids 93 to 98 of SEQ ID NO:3), the third has the sequence GGDVTL (at amino acids 127 to 132 of SEQ ID NO:3), the fourth has the sequence GTYRCY (at amino acids 176 to 181 of SEQ ID NO:3), and the fifth has the sequence GGQDGG (at amino acids 323 to 328 of SEQ ID NO:3). Human TANGO 268 is likely to be involved in cell signaling via interaction with a second receptor component. A charged residue is present in the transmembrane domain of human TANGO 268 (arginine at amino acid 272 of SEQ ID NO:3), which is a hallmark of platelet collagen receptors, and which can function as an interaction site for association with other membrane proteins, a second receptor component, e.g., FcRγ.

FIG. 5A depicts the alignment between the first immunoglobulin-like domain of human TANGO 268 (from amino acid residues 41 to 90 of SEQ ID NO:3) and a typical immunoglobulin domain (SEQ ID NO:13; Accession Number PF00047). FIG. 5B depicts the alignment between the second immunoglobulin-like domain of human TANGO 268 (from amino acid residues 127 to 182 of SEQ ID NO:3) and a typical immunoglobulin domain (SEQ ID NO:13; Accession Number PF00047).

Northern blot analysis of human TANGO 268 expression demonstrates expression in bone marrow, fetal liver, and peripheral blood leukocytes. Fetal liver expression reveals one human TANGO 268 mRNA band that is approximately 2 kb. Human TANGO 268 expression was not detected in the following tissues: spleen, lymph node, thymus, brain, heart, skeletal muscle, colon, kidney, liver, small intestine, placenta, or lung. Further analysis predicts that TANGO 268 is specific to the megakaryocyte lineage of hematopoietic cells.

Clone EpthEa11d1, which encodes human TANGO 268, was deposited with the American Type Culture Collection (10801 University Boulevard, Manassas, Va. 20110-2209) on Mar. 30, 1999 and assigned Accession Number 207180. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

FIGS. 3A-3C shows an alignment of the human TANGO 268 coding region (SEQ ID NO:2) with the human monocyte inhibitory receptor precursor protein coding region (SEQ ID NO:24). The human monocyte inhibitory receptor has been shown to downregulate activation responses by phosphatases. The nucleotide sequences of coding regions of human monocyte inhibitory receptor precursor and human TANGO 268 are 37.7% identical. The full-length nucleic acid sequence of human TANGO 268 (SEQ ID NO: 1) exhibits 49.9% identity to the full-length nucleic acid human monocyte inhibitory receptor precursor (SEQ ID NO: 11; Accession Number U91928).

FIG. 4 shows that there is an overall 23% identity between the amino acid sequence of the human TANGO 268 protein and the amino acid sequence of the human monocyte inhibitory receptor protein (SEQ ID NO:12; Accession Number U91928).

In general, human TANGO 268 has most homology to various members of the immunoglobulin superfamily that include NK inhibitory and activating receptors and Fc receptors. Specifically, TANGO 268 represents a platelet-specific collagen receptor previously described as Glycoprotein VI (GPVI), and thus can be involved in hemostasis and thrombosis. The fact that TANGO 268 represents GPVI was suggested by the following: (1) TANGO 268 and GPVI are both preferentially expressed in the megakaryocytic cells; (2) the molecular mass of the 40 kDa unglycosylated TANGO 268 is predicted to be approximately 62 kDa, the apparent molecular mass of GPVI, upon N- and O-linked glycosylation; (3) the presence of two immunoglobulin-like domains in TANGO 268 indicates that like GPVI, TANGO 268 interacts with the FcRγ; (4) the absence of a large intracytoplasmic tail, suggesting that this membrane-bound glycoprotein has no signaling role but associates with another member of the Ig family (e.g., FcRγ) protein to transduce a signal; and (5) the presence of a charged residue (arginine) in the transmembrane domain of TANGO 268 which is predicted to be present in GPVI based on its association with the FcRγ. Experimental data confirming that TANGO 268 does, indeed, represent GPVI are presented below.

Mouse TANGO 268

A cDNA encoding mouse TANGO 268 was identified by analyzing the sequences of clones present in a mouse megakaryocyte cDNA library. This analysis led to the identification of a clone, jtmea105e02, encoding full-length mouse TANGO 268. The murine TANGO 268 cDNA of this clone is 1163 nucleotides long (FIG. 6; SEQ ID NO:14). The open reading frame of this cDNA, nucleotides 63 to 1001 of SEQ ID NO:14 (SEQ ID NO:15), encodes a 313 amino acid transmembrane protein (FIG. 6; SEQ ID NO:16).

The signal peptide prediction program SIGNALP (Nielsen, et al., 1997, *Protein Engineering* 10:1-6) predicted that mouse TANGO 268 includes a 21 amino acid signal peptide (amino acid 1 to amino acid 21 of SEQ ID NO:16) (SEQ ID NO:17) preceding the mature mouse TANGO 268 protein (corresponding to amino acid 22 to amino acid 313 of SEQ ID NO:16) (SEQ ID NO:18). The molecular weight of mouse TANGO 268 without post-translational modifications is 34.5 kDa prior to the cleavage of the signal peptide, 32.3 kDa after cleavage of the signal peptide.

Mouse TANGO 268 is a transmembrane protein which consists of one or more of the following domains: (1) an extracellular domain; (2) a transmembrane domain; and (3) a cytoplasmic domain. The mouse TANGO 268 protein contains an extracellular domain at amino acid residues 1 to 267 of SEQ ID NO:16 (SEQ ID NO:19), a transmembrane domain at amino acid residues 268 to 286 of SEQ ID NO:16 (SEQ ID NO:20), and a cytoplasmic domain at amino acid residues 287 to 313 of SEQ ID NO:16 (SEQ ID NO:21).

FIG. 7 depicts a hydropathy plot of mouse TANGO 268. Relatively hydrophobic regions of the protein are shown above the horizontal line, and relatively hydrophilic regions of the protein are below the horizontal line. The cysteine residues (cys) and potential N-glycosylation sites (Ngly) are indicated by short vertical lines just below the hydropathy trace. The dashed vertical line separates the signal sequence on the left from the mature protein on the right.

Mouse TANGO 268 comprises two immunoglobulin-like domain sequences at amino acids 49 to 89 and at amino acids 135 to 181 of SEQ ID NO:16; SEQ ID NO:22 and SEQ ID NO:23. Two N-glycosylation sites having the sequences NGSH and NITA are present in mouse TANGO 268 at amino acids 93 to 96 and at amino acids 244 to 247 of SEQ ID NO:16, respectively. Six protein kinase C phosphorylation sites are present in mouse TANGO 268. The first has the sequence TLK (at amino acids 132 to 134 of SEQ ID NO:16), the second has the sequence TYR (at amino acids 178 to 180 of SEQ ID NO:16), the third has the sequence SSR (at amino acids 224 to 226 of SEQ ID NO:16), the fourth has the sequence TNK (at amino acids 233 to 235 of SEQ ID NO:16), the fifth has the sequence TEK (at amino acids 239 to 241 of SEQ ID NO:16), and the sixth has the sequence SRK (at amino acids 291 to 293 of SEQ ID NO:16). Two casein kinase II phosphorylation sites are present in mouse TANGO 268. The first has the sequence SFDE (at amino acids 140 to 143 of SEQ ID NO:16), and the second has the sequence STTE (at amino acids 237 to 240 of SEQ ID NO:16). Mouse TANGO 268 has two tyrosine kinase phosphorylation sites having the sequences KEGDTGPY (at amino acids 148 to 155 of SEQ ID NO:16) and KRPEKWY (at amino acids 156 to 162 of SEQ ID NO:16). Mouse TANGO 268 has two N-myristylation sites. The first has the sequence GSHWSL (at amino acids 94 to 99 of SEQ ID NO:16), and the second has the sequence GTYRCY (at amino acids 177 to 182 of SEQ ID NO:16). A c-AMP- and c-GMP-dependent protein kinase phosphorylation site is present in the mouse TANGO 268 having the sequence RRPS (at amino acids 226 to 229 of SEQ ID NO:16). An ABC transporter family signature is present in mouse TANGO 268 having the sequence YAKGNLVRICL-GATI (at amino acid residues 263 to 277 of SEQ ID NO:16). Mouse TANGO 268 does not include any conspicuous inhibitory or activation motifs in the cytoplasmic domain. Mouse TANGO 268 may be involved in cell signaling via interaction with a second receptor component. A charged residue is present in the transmembrane domain of mouse TANGO 268 (arginine at amino acid 270 of SEQ ID NO:16), which may function as an interaction site for association with other membrane proteins, a second receptor component, e.g., FcRγ.

FIG. 10A depicts the alignment between the first immunoglobulin-like domain of mouse TANGO 268 (from amino acid residues 42 to 91 of SEQ ID NO:16) and a typical immunoglobulin domain (SEQ ID NO:13; Accession No. PF00047). FIG. 10B depicts the alignment between the second immunoglobulin-like domain of mouse TANGO 268 (from amino acid residues 128 to 183 of SEQ ID NO:16) and a typical immunoglobulin domain (SEQ ID NO:13; Accession No. PF00047).

In situ expression experiments with a TANGO 268 antisense probe (nucleotides 69 to 670 of SEQ ID NO:14) reveal that during embryogenesis mouse TANGO 268 is expressed exclusively in the liver. The signal pattern is strong and multifocal, suggestive of expression by a scattered cell population. In adult tissues, expression of TANGO 268 in liver is no longer observed but a strong, multifocal signal is seen in spleen. The number of multifocal signals observed in the spleen is significantly reduced compared to the number observed in embryonic liver. All other adult tissues tested negative for TANGO 268 (i.e., no signal was observed in the brain, eye, harderian gland, submandibular gland, bladder, white fat, stomach, brown fat, heart, adrenal gland, colon, small intestine, liver, placenta, thymus, lymph node, spleen, lung, spinal cord, pancreas, skeletal muscle or testes). A sense probe analogous to the anti-sense TANGO 268 probe tested on the same tissues yielded no signal.

The signal pattern and restricted tissue expression observed during embryogenesis and in adult tissues was identical to that seen with a probe for TANGO 69, a gene known to be expressed by megakaryocytes (PCT Publication Number WO 99/11662, published on Mar. 11, 1999). Like TANGO 69, TANGO 268 was also cloned from a megakaryocyte library. These data, therefore, indicate that TANGO 268 is expressed by megakaryocytes during embryogenesis and in adult mice.

In general, mouse TANGO 268 has most homology to various members of the immunoglobulin superfamily that includes NK inhibitory and activating receptors and Fc receptors. The full-length nucleic acid sequence of mouse TANGO 268 exhibits 35.6% identity to the full-length nucleic acid human monocyte inhibitory receptor precursor (SEQ ID NO:11; Accession Number U91928). FIGS. 8A-8D shows an alignment of the mouse TANGO 268 coding region (SEQ ID NO:15) with the human monocyte inhibitory receptor precursor protein coding region (SEQ ID NO:24). The nucleotide sequences of the coding regions of human monocyte inhibitory receptor precursor and mouse TANGO 268 are 34.4% identical. The nucleotide sequences of the full-length human monocyte inhibitory receptor precursor (SEQ ID NO:11; Accession Number U91928) and full-length mouse TANGO 268 (SEQ ID NO:14) are 35.6% identical. FIG. 9 shows that there is an overall 20.3% identity between the mouse TANOO 268 amino acid sequence and the human monocyte inhibitory receptor protein amino acid sequence (SEQ ID NO:12: Accession Number U91928).

FIG. 11 shows that there is an overall 64.4% identity between the precursor human TANGO 268 amino acid sequence (SEQ ID NO:3) and the precursor mouse TANGO 268 amino acid sequence (SEQ ID NO:16). This homology is spread throughout the molecule, but is slightly higher (78%) over the immunoglobulin-like domains Interestingly, both human and mouse GPVI contain conserved variants of the WSXWS box (residues 96-100 and 192-196). This motif is a signature of class I hematopoietic receptors but variants are also found in the sequences of all Killer-cell Inhibitory receptors (KIR) (Fan et al., 1997, *Nature* 389: 96-100). These motifs have been shown to contribute to tertiary folding. GPVI has a relatively short cytoplasmic tail with no obvious signaling motifs analogous to the ITAM's and immunoreceptor tyrosine-based inhibitory motifs (ITIM's) of other signaling receptors. However, GPVI present a positively charged residue in the transmembrane domain allowing it to form complexes with the FcRγ chain which acts as signaling subunit (Poole et al., 1997, cited below).

Clone EpTm268, which encodes mouse TANGO 268, was deposited with the American Type Culture Collection (10801 University Boulevard, Manassas, Va. 20110-2209) on Jun. 14, 1999 and assigned Accession No. PTA-225. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

Functional and Structural Analyses Demonstrating that TANGO 268 is Glycoprotein VI Described below are both functional (ligand binding, cell adhesion and platelet activation) and structural (immunoblot and tissue expression) analysis demonstrating that TANGO 268 is glycoprotein VI.

A. Ligand Binding Assay

Convulxin (Cvx) is a protein purified from the venom of *Crotallus durissus terrificus*. Cvx is known to act as a potent platelet agonist, and has been shown to bind specifically to GPVI. Described below are Cvx ligand binding studies demonstrating that TANGO 268 specifically binds Cvx.

The ligand binding assay was performed as follows: approximately $5 \times 10^9$ human platelets per milliliter, and $10^6$ expression vector only-transfected CHO cells and full-length TANGO 268 containing expression vector-transfected CHO cells were lysed for 30 min at 4° C. in lysis buffer comprising 10 mM Tris, 100 mM NaCl, 5 mM EDTA, pH 8 containing 0.1% Nonidet P40, 2 mM PMSF, 5KIU aprotinin and 20 µM leupeptin (Jandrot-Perrus et al., 1997, J. Biol. Chem. 272: 27035-27041; Lagrue et al, 1999, FEBS Lett. 448(1):95-100). Approximately 8 µg of platelet lysate and 40 to 80 µg of CHO cell lysates (expression vector only-transfected and TANGO 268-transfected) were separated on 10% acrylamide slab gels (miniprotean II Biorad) in the presence of SDS and then transferred to a PVDF membrane (Amersham). The membrane was saturated with 5% (w/v) non-fat dry milk in PBS. Ligand blotting was performed by the incubating membrane in the presence of $^{125}$I -Cvx ($3 \times 10^5$ cpm/ml) in PBS pH 7.4 containing 0.5% (w/v) dry milk and 0.2% Tween 20 for 4 hours.

The Cvx utilized in the ligand binding assay was purified from the venom of *Crotallus durissus terrificus* by two successive chromatography steps (Francischetti et al., 1997, *Toxicon* 35:121728) and radiolabeled. Briefly, lyophilized venom from *Crotallus durissus terrificus* was solubilized in ammonium formate 0.1M, NaCl 0.3 M, pH 3.1 and proteins were separated on a G75 column equilibrated in the same buffer. Cvx contained in the first eluted peak, as assessed by gel electrophoresis and platelet activating activity, was lyophilized. Second, Cvx was solubilized in Tris 0.1M pH8.5 containing 6 M urea (Tris urea buffer) and further purified by chromatography on a G100 column equilibrated in the same buffer. Fractions containing purified Cvx were pooled, dialyzed and lyophilized. After solubilization in the Tris urea buffer, Cvx was dialyzed against PBS (20 mM phosphate, 150 mM NaCl, pH 7.4). Cvx (100 µg) was radiolabeled with 0.5 mCi Na$^{125}$I (Amersham) using Iodogen (Pierce Chemical Corp.) according to published procedure (Jandrot-Perrus et al., 1997, *J. Biol. Chem.* 272:27035-27041). Iodinated Cvx was separated from free $^{125}$I by gel filtration on a G25 sephadex column (Pharmacia) in PBS. The activity of $^{125}$I-Cvx was tested on human platelet aggregation.

Following the incubation of the membrane with $^{125}$I-Cvx, the membrane was washed and ligand binding was detected by autoradiography on X-Omat MA films (Kodak). Ligand blotting with $^{125}$I-Cvx (FIG. 12) revealed one specific band in platelet lysates at 56-58 kDa (lane 1), which represents a band previously identified as GPVI (Jandrot-Perrus et al., 1997, *J. Biol. Chem.* 272:27035-27041). No positive band was observed in lysates (60 µg) from control expression vector only-transfected cells (lane 2). In lysates from CHO cells transfected with TANGO 268 expression vector (60 µg), a positive band migrating at 52-54 kDa was clearly observed (lane 3).

Figure 12:
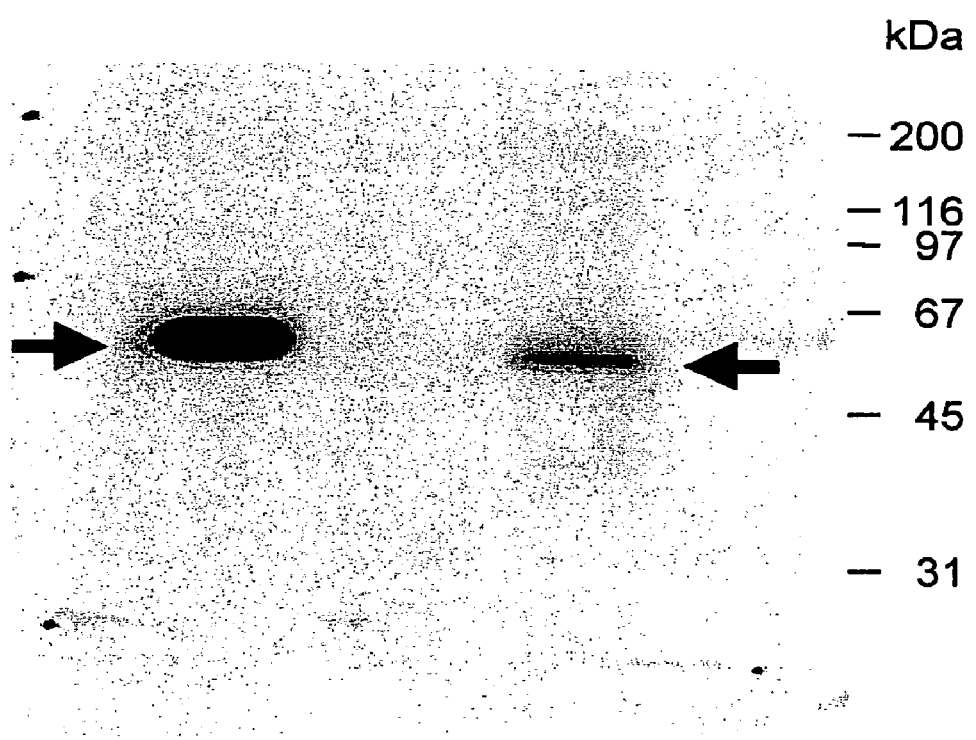
FIG. 12 depicts the results from the ligand blotting assay with $^{125}$I-convulxin (Cvx), demonstrating that TANGO 268 specifically binds Cvx. Lane 1 contains platelet lysate, lane 2 contains lysate from expression vector-only transfected CHO cells, and lane 3 contains TANGO 268-transfected CHO cell lysate. The cell lysates were separated on polyacrylamide gels, transferred to PVDF membranes, and the membranes were incubated with $^{125}$I-Cvx. The interaction between $^{125}$I-Cvx and TANGO 268 was detected by autoradiography.

The ligand binding studies demonstrate that convulxin binds to a molecule present on TANGO 268 transfected cells (and not on vector only transfected cells), which has a molecular weight very similar to the molecular weight of GPVI (FIG. 12). The small apparent difference in size between the band in platelet lysates and in CHO lysates can be accounted for by cell-type specific discrepancies in protein glycosylation.

This result demonstrates that convulxin binds to TANGO 268 and that TANGO 268 has a similar or identical molecular weight as GPVI. Since GPVI is the platelet receptor for Cvx (Jandrot-Perrus et al., 1997, *Journal of Biological Chemistry* 272:27035-27041) and TANGO 268 is preferentially expressed in megakaryocytes, this functional evidence indicates that TANGO 268 is GPVI.

B. Immunoblotting Assay

Structural evidence is presented herein that further supports TANGO 268 as corresponding to GPVI. In particular, the immunoblotting results presented herein demonstrate that an IgG preparation containing antibodies directed against GPVI binds specifically to TANGO 268 polypeptide. These studies further demonstrate that binding is successfully competed away when Cvx is introduced.

The immunoblotting assay was performed as follows: platelet, expression vector-only transfected and TANGO 268 containing expression vector-transfected CHO cell lysates were generated as described in A. above. Approximately 8 µg of platelet lysate and 40 to 80 µg of CHO cell lysate (either expression vector-only transfected or TANGO 268-transfected) were separated on 10% acrylamide slab gels (miniprotean II Biorad) in the presence of SDS and then transferred to a PVDF membrane (Amersham). The membrane was saturated with 5% (w/v) non-fat dry milk in PBS, and then incubated for 2 hours at room temperature with 9 µg/ml anti-GPVI IgG in PBS, pH 8.6 containing 0.02% (v/v) Tween 20.

Alternatively, for the competition assay, the membrane was incubated for 2 hours at room temperature with 9 µg/ml anti-GPVI IgG in PBS, pH 8.6 containing 0.02% (v/v) Tween 20 in the presence of a high concentration of cold Cvx (0.5 µM).

The IgG preparation utilized in this assay was generated by purifying IgG from serum of a patient exhibiting idiopathic thrombocytopenic purpura (ITP) (Sugiyama et al., 1987, *Blood* 69: 1712-1720) as described in Jandrot-Perrus et al., 1997, *J. Biol. Chem.* 272:27035-27041. Following the incubation with the antibody composition, the membrane was washed and incubated with peroxidase-coupled protein A (Amersham) for 2 hours at room temperature. The immunoblots were developed using enhanced chemiluminescence detection (Amersham).

Figure 13A:
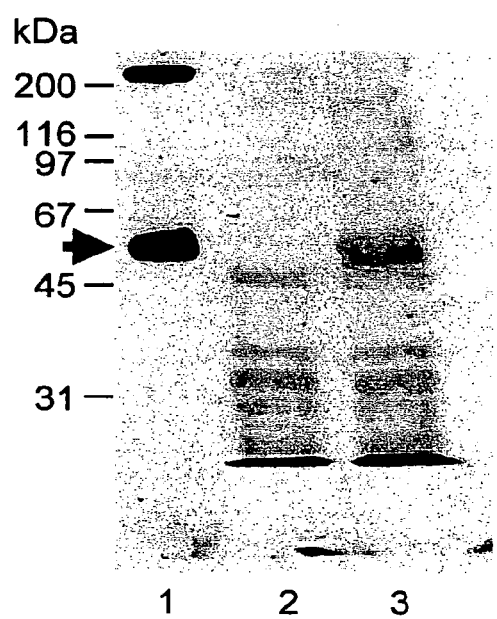
FIG. 13A depicts the results from the immunoblotting assay with anti-GPVI Ig antibody, demonstrating that TANGO 268 specifically binds to anti-GPVI Ig antibody. The cell lysates were separated on polyacrylamide gels, transferred to PVDF membranes, the membranes were incubated with anti-GPVI IgG antibody followed by an incubation with peroxidase-coupled protein A, and TANGO 268 expression was detected by enhanced chemiluminescence.

As shown in FIG. 13A, immunoblotting with the IgG revealed a 56-58 kDa in platelet lysates (lane 1), which corresponds to the molecular mass of GPVI. The high molecular weight band detected in platelet lysates corresponds to platelet IgGs revealed by protein A. The presence of a 52-54 kDa band was detected in TANGO 268-transfected CHO cell lysates (FIG. 13A, lane 3) but not in expression vector only-transfected CHO cell lysates (lane 2) demonstrating that TANGO 268 shares epitope similarities with GPVI. The low molecular weight bands of moderate intensity observed in FIG. 13A, lanes 2 and 3 are non-specific bands since they were detected in both control, expression vector only-transfected and TANGO 268 transfected CHO cell lysates.

Figure 13B:
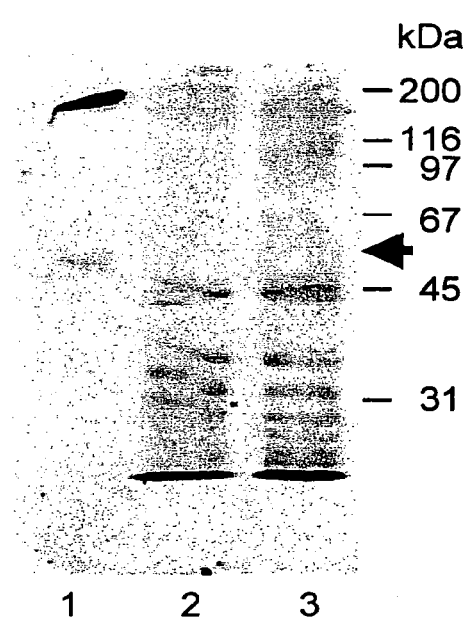
FIG. 13B depicts the results of anti-GPVI IgG binding following competition with Cvx, which demonstrates that Cvx competes with anti-GPVI Ig antibody for binding to TANGO 268. Lane 1 contains platelet lysate, lane 2 contains lysate from expression vector-only transfected CHO cells, and lane 3 contains TANGO 268-transfected CHO cell lysate. The cell lysates were separated on polyacrylamide gels, transferred to PVDF membranes, the membranes were incubated with anti-GPVI IgG antibody in the presence of Cvx followed by an incubation with peroxidase-coupled protein A, and TANGO 268 expression was detected by enhanced chemiluminescence.

The results from the competition assay performed further demonstrate the similarities between TANGO 268 and GPVI. In particular, as shown in FIG. 13B, cold 0.5 µM Cvx successfully competes with and inhibits anti-GPVI binding to GPVI on platelet lysates (lane 1), and likewise, the 52-54 kDa band revealed by the anti-GPVI IgG in TANGO 268-tranfected cells lysates (lane 3), was inhibited in the presence of 0.5 µM Cvx.

In summary, the results from both the ligand binding assays and immunblotting assays described above provide both functional (i.e., binding of Cvx to TANGO 268) and immunological evidence (i.e., recognition by anti-GPVI IgG) that TANGO 268 does, indeed, represent GPVI polypeptide.

C. Tissue Expression of Tango 268/GPVI

To further study tissue distribution of both mouse and human Tango 268/GPVI, Northern blot, RT-PCR and in situ hybridizations were performed. The results presented herein confirm and extend the experimental results presented above.

Materials & Methods

In situ hybridization: In situ hybridization (ISH) was performed with day 12.5 C57BIJB6 mouse embryos and normal 4- to 6-week-old C57BL/6 mouse femurs. Tissues were fixed in 10% formalin, paraffin embedded and subsequently sectioned at 4 µm onto Superfrost/plus slides. Femurs were decalcified in TBD-2 (Shandon, Pittsburgh, Pa.) prior to paraffin embedding. Sections were deparaffinized in xylene, hydrated through a series of graded ethanol washes and placed in DEPC-treated phosphate-buffered saline (PBS) pH7.4 before being processed for ISH. Sections were incubated in 20 ug/ml proteinase K (Sigma) in DEPC-PBS for 15 minutes at 37° C. and then immersed in 4% formaldehyde/PBS for 5 minutes. Sections were treated with 0.2N HCl for 10 minutes followed by DEPC-PBS. Sections were rinsed in 0.1M triethanolamine-HCl (TEA, pH 8.0), incubated in 0.25% acetic anhydride-TEA for 10 minutes, rinsed in DEPC-PBS, dehydrated through a series of graded ethanol washes and air dried. Labeling and hybridization of $^{35}$S-radiolabeled ($2.5 \times 10^7$ cpm/ml) cRNA antisense and sense RNA probes encoding a 599 pb fragment of the 5' end of the GPVI gene (generated with the PCR primers forward 5'CAGCCTCACCCACTTTCTTC-3' (SEQ ID NO:25), nt 8-27 and reverse 5'-CCACAAGCACTAGAGGGTCA 3' (SEQ ID NO:26), nt 607-588) were performed as previously described (Busfield et al., 1997, *Mol. Cell. Biol.* 17: 4007-14). Following hybridization, sections were dehydrated rapidly through serial ethanol-0.3 M sodium acetate before being air dried, dipped in a nuclear track emulsion (NTB-2: Eastman Kodak, Rochester, N.Y.) and exposed for 60 days at room temperature. Slides were developed with D-19 (Kodak, Rochester, N.Y.), stained with hematoxylin and eosin-Y, and coverslipped.

Cell lines: The HEL (erythroid/MK), U937 (monoblast), K562 (erythroid), CEM (T cell), HEPG2 and Hela cell lines were obtained from American Type Culture Collection (ATCC, Manassas, Va.) and the FDC-P1 and 32D cells from D. Metcalf (The Walter and Eliza hall Institute, Melbourne, Australia). The UT7 (erythroid/MK) transduced by c-mpl (Hong et al., 1998, *Blood* 91:813-822) TF1 (erythroid), KG1 (myeloblast), HL60 (myeloblast/promyelocyte), MO-7E (MK), Meg-01 (MK) and DAMI (MK) were obtained from the different laboratories which derived them (Avanzi et al., 1988, *Br. J. Haematol.* 69: 359-366) (Collins et al., 1977, *Nature* 270: 347-349) (Greenberg et al., 1988, *Blood* 72: 1968-1977) (Kitamura et al., 1989, *J. Cell Physiol.* 140: 323-334) (Koeffler and Golde, 1977, *Science* 200:1153-1155.) (Komatsu et al., 1991, *Cancer Res.* 51: 341-348) (Ogura et al., 1985, *Blood* 66:1364-1392).

HEL, U937 HL60, Meg-01, KG1 and K562 human cell lines were cultured in IMDM (Gibco/BRL, Grand Island, N.Y.), 10% FCS (Stem cell technology, Vancouver, BC, Canada). The c-mpl UT7, TF1 and MO-7E are factor dependent and were grown either in the presence of 2 ng/ml GM-CSF or 10 ng/ml PEG-rHuMGDF in IMDM 10% FCS. CEM and Hela were grown in RPMI (Gibco/BRL, Grand Island, N.Y.). FDC-P1, 32D and Ba/F3 murine cell lines were cultured in DMEM (Gibco/BRL, Grand Island, N.Y.), 10% FCS (Stem cell technology, Vancouver, BC, Canada). Cultures were performed at 37° C. in a fully humidified atmosphere of 5% CO2.

Samples: Human megakaryocytes were obtained as described for the human libraries from mobilized or cord blood CD34$^+$ cord blood. A fetal liver was obtained from abortion at 12-week gestation after obtaining informed consent.

Northern Blot/RT PCR analysis: Human multiple tissue northern blots, purchased from Clontech (Palo Alto, Calif.) were hybridized to a 1.0 kb human GPVI probe as described by the manufacturer. Total RNA was isolated using RNA PLUS (Bioprobe systems, France), a modification of the acid-guanidinium thiocyanate-phenol-chloroform extraction method of Chomczynski et Sacchi (Chomczynski and Sacchi 1987). RNA was reverse transcribed with random hexamers using SUPERSCRIPT reverse transcriptase (Gibco BRL/Life Technologies, Cergy Pontoise, France).

For human cell lines and tissues, after reverse transcription, each sample was subjected to a specific amplification of GP VI and $\beta_2$ microglobulin cDNA. The sequences of the specific primers were: for GP VI sense primer 5'-TTCTGTCT-TGGGCTGTGTCTG-3' (SEQ ID NO:27) and anti-sense primer 5'-CCCGCCAGGATTATTAGGATC-3' (SEQ ID NO:28), for $\beta_2$ microglobulin sense primer 5'-CCT-GAAGCTGACAGCATTCGG-3' (SEQ ID NO:29) and anti-sense primer CTCCTAGAGCTACCTGTGGAG-3' (SEQ ID NO:30). PCR was performed in 25 µl reaction mixture containing 0.3 U Taq polymerase (ATGC Noisy-le-Grand, France), 200 µM dNTP, 30 pmol of oligonucleotide sense and 30 pmol of antisense for GP VI amplification and 10 pmol of oligonucleotide sense and 10 pmol of antisense for $\beta_2$ microglobulin amplification, in ATGC buffer. The reaction mixture was subjected to denaturation for 5 min at 95° C. amplified by 35 cycles as follows: denaturation for 30 seconds at 94° C., annealing for 30 seconds at 60° C. and extension at 72° C. for 1 min, with a final 7 min extension at 72° C. in a thermocycler 2400 (Perkin Elmer Co, Courtaboeuf, France). PCR products (9 µl) were electrophoresed on a 2% agarose gel. Fragments were visualized by illumination after ethidium bromide staining. MassRuler DNA Ladder, low Range (MBI Fermentas, Amherst, N.Y.) is used as marker.

Results

Figure 14A:
FIG. 14A: In situ hybridization of a day 12.5 mouse embryo. Hybridization is exclusively observed in the liver during embryogenesis. No signal was seen with the sense probe (data not shown). High magnitude resolution shows that the only positive cell population corresponded to fetal megakaryocytes (data not shown). In adult, expression in liver was no longer observed but a strong, multifocal signal was seen in spleen and in the bone marrow.
Figure 14B:
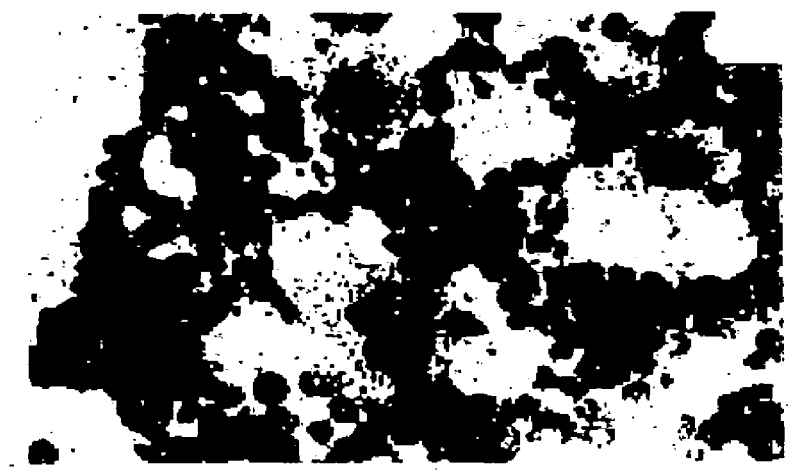
FIG. 14B: high magnitude resolution from a photoemulsion processing carried out on a 6-week-old mouse femur section shows expression restricted to megakaryocytes. No signal was observed in any other adult tissues analyzed (see results).

Human tissues were studied using Northern blot or RT-PCR analysis. Northern blots (FIG. 14D) revealed no specific message in brain, heart, skeletal muscle, colon, thymus, spleen, kidney, liver, small intestine, placenta, lung or lymph nodes. A 2 kb transcript was only observed in bone marrow and fetal liver. A signal was inconsistently observed with peripheral blood cells, probably due to platelet RNA contamination in some samples. Indeed, transcripts for platelet glycoprotein IIb (GPIIb), a platelet specific protein, were also detected in these positive samples.

Figure 14C:
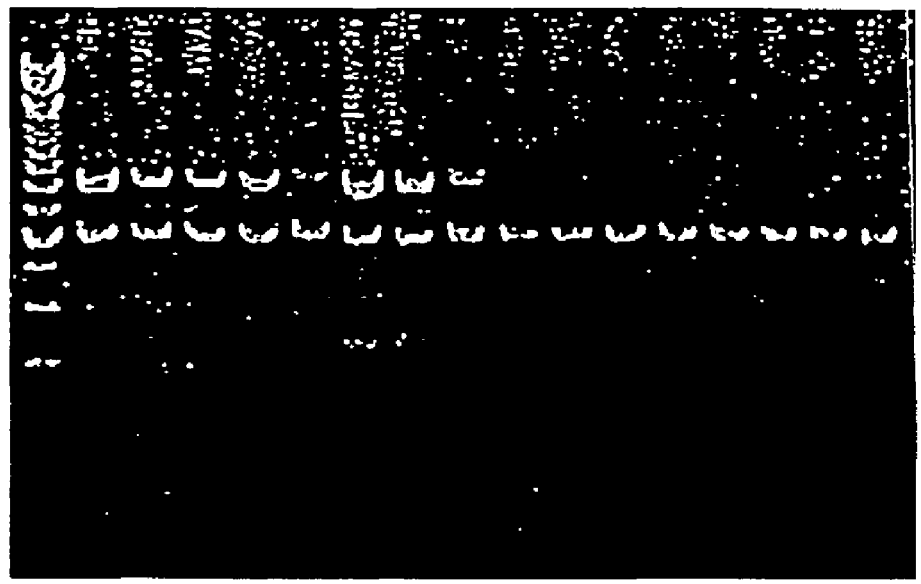
FIG. 14C: RT-PCR analysis from human samples. $\beta_2$ microglobulin and GPVI transcripts were co-amplified. The high molecular weight fragment (830 bp) is generated from the GPVI primers and the low molecular weight fragment (603 bp) is generated from the $\beta_2$ microglobulin primers. The $\beta_2$ microglobulin PCR product, used as a loading control, is present in all the samples in similar quantity. In contrast, GPVI is only amplified in megakaryocyte-enriched samples (adult and newborn), in cell lines displaying strong MKC features (HEL, MEG01, DAMI, MO7E, mpl-UT7) and at a lesser extend in fetal liver cells. A very low signal is also detected in the K562 and KG1 cell lines, two cell lines which also express GPIIb at low level, but no expression was detected in the other samples.
Figure 14D:
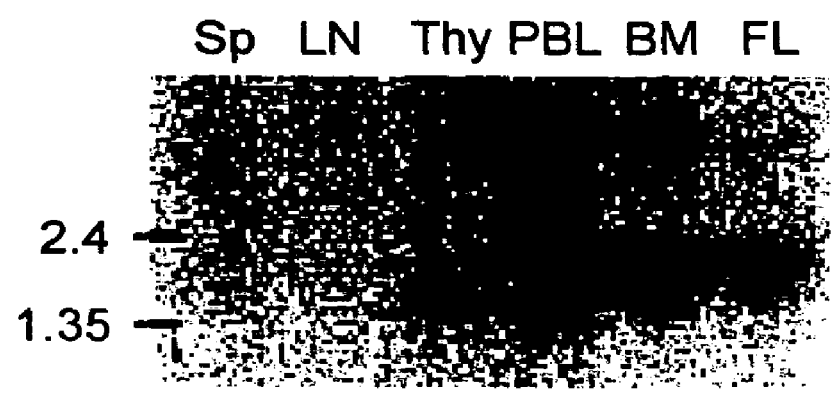
FIG. 14D: Northern blot analysis of human tissues. A 2 kb transcript is only observed in bone marrow and fetal liver. A signal is also observed with peripheral blood leucocytes (PBL). However, when the same blot was hybridized with a GPIIb probe, a platelet protein absent in PBL, transcripts were also detected suggesting that the signal was due to platelet RNA contamination. No signal was observed in a different PBL sample but also in brain, heart, skeletal muscle, colon, thymus, spleen, kidney, liver, small intestine, placenta, lung or lymph nodes (data not shown).

Using RT-PCR analysis, no GPVI transcript was detected in blood cells except in platelets. In cell lines, a strong PCR signal was observed in the HEL, MEG01, DAMI and TPO-stimulated MO7E and mpl transduced UT7 cell lines (Hong et al., 1998, *Blood* 91:813-822). A very low signal was also detected in the K562 and KG1 cell lines, two cell lines also expressing GPIIb at low level, but no expression was detected in the HEPG2, CEMT, TF1, U937, HL60 and Hela cells. CD41 positive cells (including more than 95% megakaryocytes) isolated from normal cord blood or chemotherapy-induced mobilized peripheral blood displayed a strong RT-PCR signal. Fetal liver cells expressed a moderate level of expression compared to megakaryocyte-enriched samples (FIG. 14C)

Mouse tissues were studied using northern blot and ISH analysis. ISH reveals that GPVI was exclusively found in the liver during embryogenesis (FIG. 14A). The signal pattern was strong and multifocal, suggestive of expression by a scattered cell population. This signal was observed at embryonic day 13.5, 14.5, 16.5 and decreased in intensity at day 18.5 and in 1.5 day old new born. In adult, expression in liver was no longer observed but a strong, multifocal signal was seen in spleen and in the bone marrow. No signal was observed in any other tissues including brain, eye, harderian gland, submandibular gland, bladder, white fat, stomach, brown fat, heart, adrenal gland, colon, small intestine, liver, placenta, thymus, lymph node, lung, spinal cord, pancreas, skeletal muscle, testes. Photoemulsion processing of the spleen and bone marrow showed that this expression was restricted to megakaryocytes (FIG. 14B).

In conclusion, despite screening a large number of human and mouse tissues, GPVI expression was only detected in megakaryocytes/platelets. This result strongly suggests that GPVI is restricted to this hematopoietic lineage. Presently there are very few molecules that are specific to the megakaryocyte lineage. GPIIb (integrin αIIb), which was long considered to be the prototypic megakaryocyte marker, is also expressed on a subset of hematopoietic progenitors. Other megakaryocyte proteins such as GPIbα, β and GPIX (CD42) are also expressed by activated endothelial cells. Only PF4 appears to be specific to the megakaryocyte/platelet lineage. For this reason the PF4 promoter has been used to target the megakaryocytes in various transgenic models (Ravid et al., 1991, *Proc. Nat'l. Acad. Sci. USA* 88:1521-5.). Thus, the GPVI promoter can also be used to target specifically the megakaryocyte lineage. For example, the polynucleotides of the invention can be used to specifically target, via homologous recombination, a gene of interest into the GPVI locus under the control of the GPVI promoter. Alternatively, the GPVI promoter region can be cloned using standard techniques known to those in the art (e.g., probing a genomic library by hybridization to the 5' end of the cDNAs of the invention, and more specifically, detecting hybridization of the human TANGO 268 clone to a human genomic library of chromosome 19 in particular).

D. Flow Cytometry To Study Cell Surface Expression of Tango 268/GPVI

In order to determine whether the recombinant GPVI was expressed at the cell surface, different human or murine hematopoietic cell lines were transduced with recombinant retroviruses expressing human or murine GPVI and with the control retrovirus.

Materials & Methods

GPVI expressing cell lines: CHO cells were transfected using lipofectamine (Gibco-BRL, Grand Island, N.Y.), according to manufacturer's instructions. The expression vector (pMET, Millennium Pharmaceuticals, Cambridge, Mass.) containing the full length GPVI cDNA, driven by a SRalpha promoter, was isolated from the cDNA library. Control CHO cells were transfected with the empty vector. Cells were collected 2 days after transfection and lysed in 12 mM Tris, 300 mM NaCl, 12 mM EDTA, containing 2 µM leupeptin, 2 mM PMSF, 5 KIU aprotinin, and 0.2% (v/v) NP40 (Sigma, St. Louis, Mo.). After 20 min at 4° C. under agitation, samples were centrifuged at 13,000 g for 15 min at 4° C. and the supernatants frozen at −80° C. for analysis.

The human cell lines HEL, U937 and K562 and the murine cell lines FDC-P1, 32D and Ba/F3 murine cell lines were engineered (Burns et al., 1993, *Proc. Nat'l Acad. Sci. USA* 90: 8033-7) to express GPVI using the pMSCVpac retrovirus (Hawley et al., 1994, *Gene Ther.* 1: 136-8). Briefly, viruses carrying the full length cDNA encoding human GPVI or murine GPVI were constructed using base perfect PCR amplified fragments of the cDNAs (Clontech laboratories Inc, Palo Alto, Calif.). Viral supernatants were generated into the 293-EBNA cells (Invitrogen, Carlsbad, Calif.) by transfecting the retroviral construct and two pN8epsilon vectors containing the gag/pol genes from the murine moloney leukemia virus (MMLV) or the Vesicular Stomatitis Virus envelope glycoprotein G (VSV-G) gene. Concentrated viral supernatants were prepared by centrifugation at 4° C. using a SW28 rotor at 50,000×g (25,000 rpm) for 2 hr. Pellets were resuspended in 1.5 ml of DMEM for 24 hr at 4° C., shaken at 4° C. for 24 hours and frozen at −80° C. For transduction, cell lines were incubated with the viral supernatant over-night in 24 well plates, 10×10$^5$ cell/ml, and selected during one week using puromycin (4 µg/ml, Sigma, St. Louis, Mo.). Human and murine GPVI were transduced in human and murine cell lines, respectively. Expression of the genes was verified using PCR analysis. The control cells were transduced with the empty virus.

Convulxin and Bothrojaracin preparation: Convuixin (Cvx) was purified from the venom of *Crotalus durissus terrificus* mainly as described by Francischetti et al, using a two step gel filtration procedure of sephadex G75 (Pharmacia Biotech, Uppsala, Sweden) followed by sephacryl 5100 (Pharmacia Biotech, Uppsala, Sweden). Cvx was labeled with $^{125}$I using the iodogen procedure (Pierce Chemical Co, Rockford, Ill.) and Na$^{125}$I (Amersham, Les Ulis, France). Cvx was coupled to FITC by mixing Cvx in 50 mM NaHCO3, 150 mM NaCl, pH 9.5 with a 100 fold molar excess of FITC (Aldrich, St Quentin Fallavier, France) overnight at 4° C. FITC-coupled Cvx was separated from free FITC by chromatography on a sephadex G25 column (PD10 Pharmacia Biotech, Uppsala, Sweden) in 20 mM phosphate, 150 mM NaCl pH 7.4 (PBS). Bothrojaracin, a specific thrombin inhibitor purified from the venom of Bothrops jararaca as previously described (Arocas et al., 1996, *Biochemistry* 35: 9083-9) was coupled to FITC using the same procedure.

Flow cytometry: Cells transduced with the human or murine GPVI viruses or the control virus were incubated in the presence of 20 nM FITC-Cvx or FITC-bothrojaracin for 60 min. at room temperature. After dilution in PBS cells were analyzed by FACSort flow cytometer (Becton Dickinson, Franklin Lakes, N.J.).

Results

It was observed that the cell lines used for this study express FcRγ-chain, as indicated by immunoblotting studies using a polyclonal anti-FcRγ antibody. Functional characterization of recombinant GPVI was performed using transfected cells which have either no (U937, FDC-P1) or low (HEL) levels of endogenous GPVI. Unlike DAMI cells which do express GPVI mRNA, this allowed us to measure responses independent of endogenous GPVI.

Figure 15A:
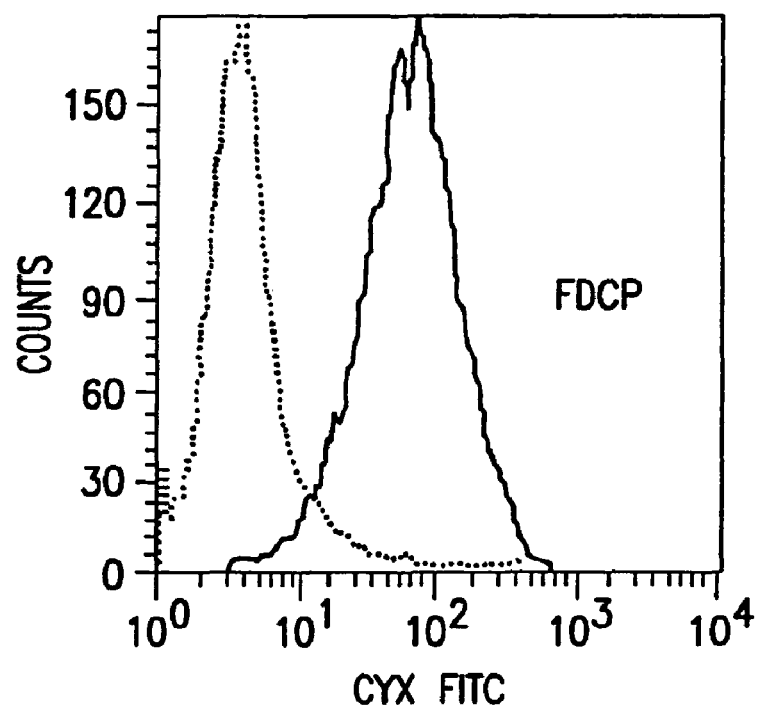
FIG. 15A: FDC-P1.
Figure 15B:
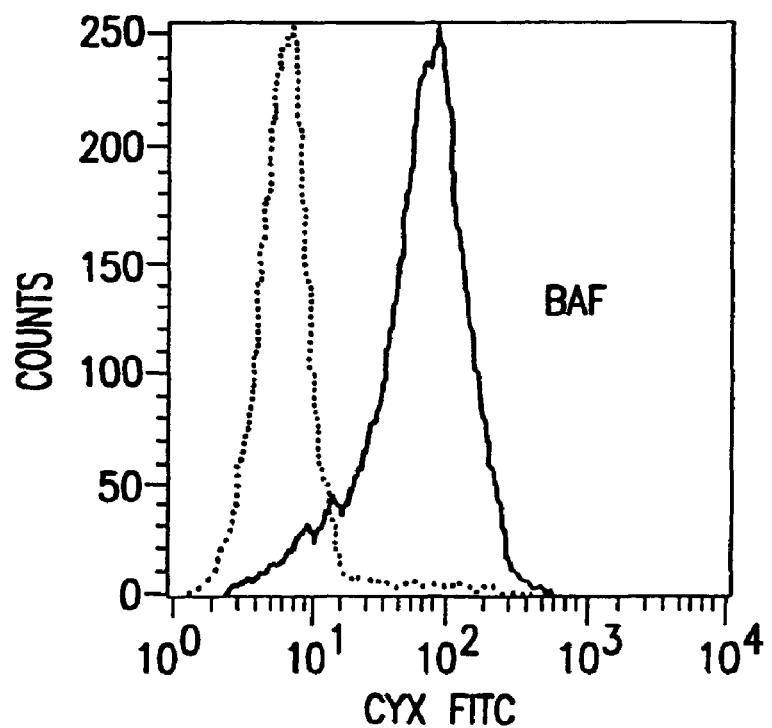
FIG. 15B: Ba/F3.
Figure 15C:
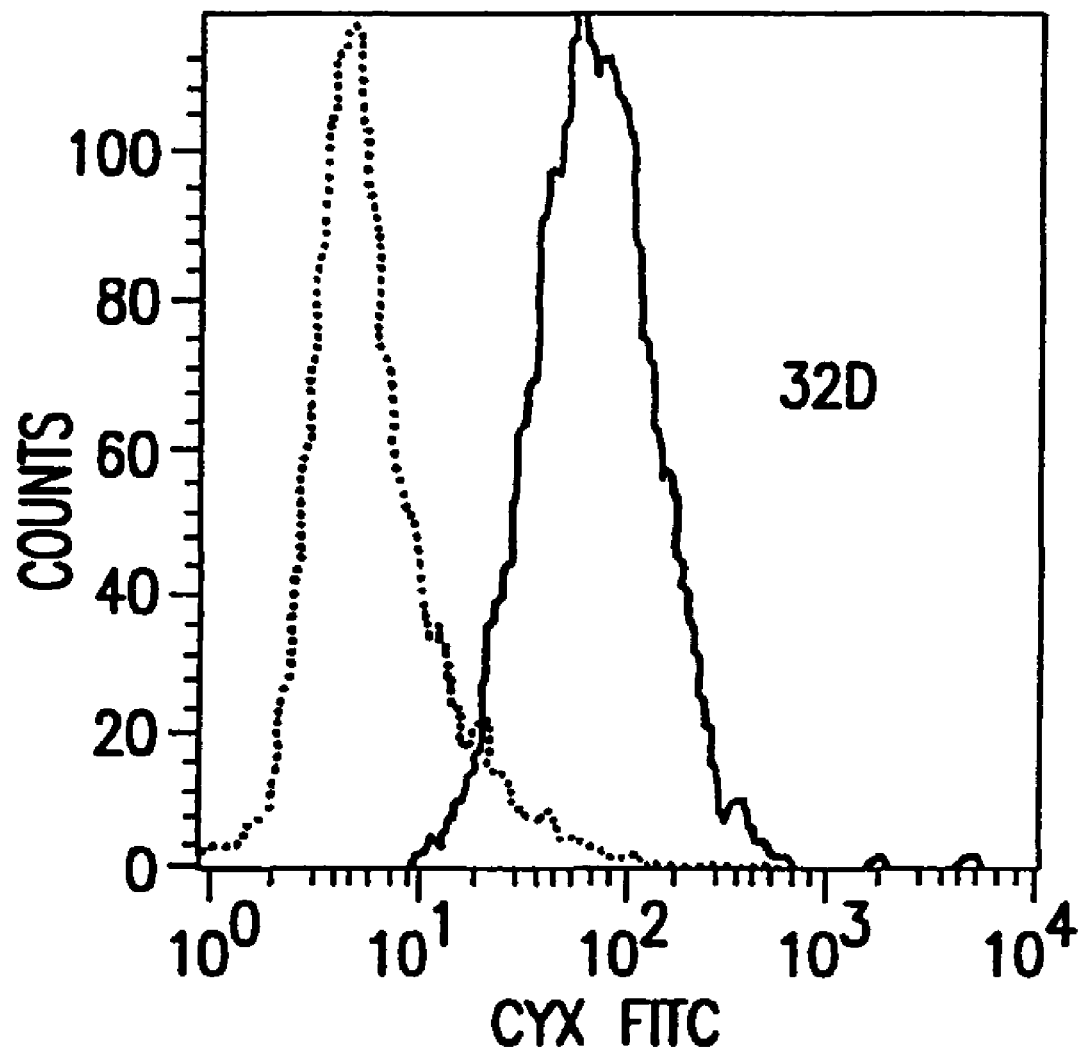
FIG. 15C: 32D. Dotted line: control cells transduced with the empty vector, plain line cells transduced with the retrovirus carrying rmGPVI.

Transduced cells were analyzed by flow cytometry using FITC conjugated Cvx. As a control, we used FITC conjugated bothrojaracin, another snake venom protein structurally very close to Cvx but a pure thrombin inhibitor that does not bind to platelets. Transduction of murine 32D cells with a retrovirus expressing murine GPVI resulted in a strong Cvx-associated staining compared to cells transduced with the control virus, indicating that these cells express GPVI at their surface (FIG. 15). Similar results were obtained with FDC-P1, and Ba/F3 (all murine cell lines) and with K562 and U937, indicating that murine or human GPVI are expressed at the surface of all these cell lines after transduction. Cvx was found to bind to the wild type HEL cells but the binding was clearly increased after retroviral transduction indicating an increased expression in cells already constitutively expressing GPVI.

Discussion

This ligand binding fluorescence analysis shows that Cvx binds to the human recombinant protein in U937 and K562 cells and to the mouse recombinant protein in FDC-P1, 32D and Ba/F3. It is known that Cvx recognized mouse GPVI from studies showing that Cvx is a potent platelet activator of both human and mouse platelets. Expression of recombinant GPVI at the cell surface may have been facilitated by the coexpression of the FcRγ chain in these cells. It has been shown previously that expression of the FcRγ chain is required for surface expression of the FcγRI, FcγRIII, FcεRI, and for activation of platelets by collagen (Poole et al., 1997, *EMBO J.* 16(9):2333-2341) in mice lacking the FcRγ.

E. Cell Adhesion

Since GPVI was expressed at the cell surface of transfected cells, its capacity to promote cell adhesion in a static system, to either immobilized Cvx or collagen, was tested, and then this result was compared this to immobilized BSA.

Materials & Methods

Cell adhesion: Collagen type I (2 µg, Chrono-log corp. Haverton, Pa.), Cvx (1.4 µg) or BSA (2 µg, Sigma, St Louis, Mo.) in 100 µl PBS were immobilized on Immulon II plates (Dynatech, St Cloud, France) overnight at 4° C. Plates were then saturated with 2 mg/ml BSA in PBS for one hour and washed with PBS. Cells in culture medium were labeled with $^{51}$Cr (CIS Bio International, Gif sur Yvette, France) for one hour at 37° C. after centrifugation at 150 g for 10 min, cells were washed with Hanks buffer containing BSA (2 mg/ml) and resuspended in the same buffer. Cells were added to the wells. After 60 min. at room temperature, wells were emptied and washed and the samples counted for $^{51}$Cr.

Results

Figure 16A:
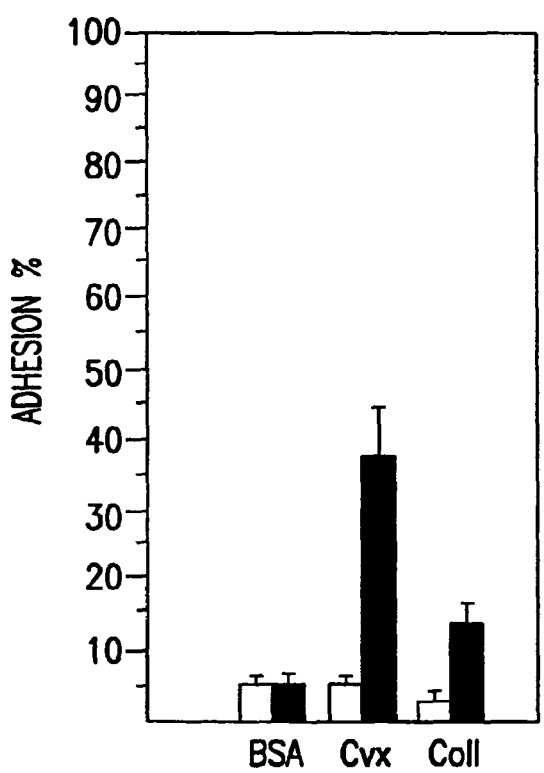
FIG. 16: Adhesion of cells expressing rhGPVI or rmGPVI to immobilized Cvx or collagen. BSA, Cvx or collagen type I were immobilized on microtitration plates. GPVI transduced or control U937 (FIG. 16A) or FDC-P1 (FIG. 16B) cells were labeled with $^{51}$Cr and incubated for 60 min in the wells. After aspiration of the non-bound cells and washing, radioactivity associated to the wells was counted to determine adherent cell number. Results are expressed as the percentage of the cells added to the wells and are the mean+/−SEM of three determinations. Empty bars: control cells; filled bars: GPVI expressing cells.
Figure 16B:
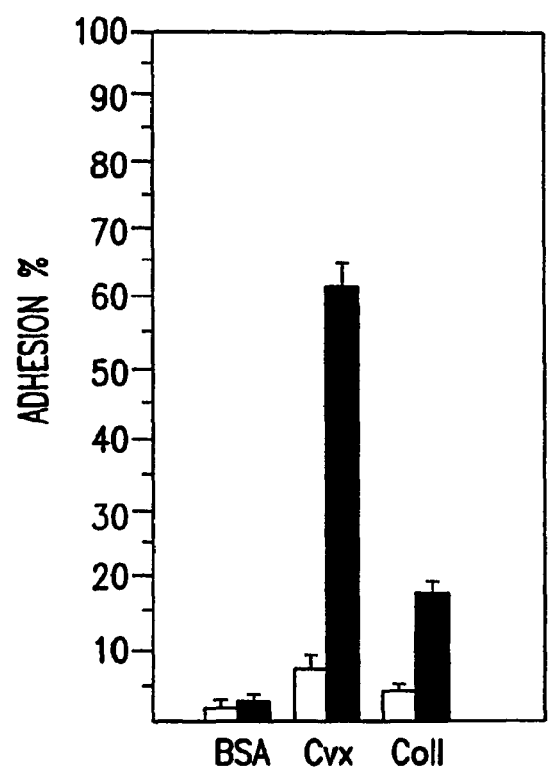

Two cell lines were tested: U937 and FDC-P 1. Neither the cells expressing GPVI, nor the control cells bound to immobilized BSA. However, expression of recombinant human or mouse GPVI in U937 or FDCP-1, respectively, clearly promotes the adhesion of these cells to immobilized collagen and to a greater extent to immobilized Cvx (FIG. 16). This result indicates that GPVI protein functions as a receptor for collagen I. In addition, GPVI is a receptor for collagen III.

F. Association of Recombinant GPVI with FcRγ Chain

To analyze whether recombinant GPVI was expressed associated with FcRγ chain we performed immunoprecipitation studies with an anti-FcRγ polyclonal antibody on lysates of U937 transduced cells compared to platelets.

Materials & Methods

Protein analysis: The different cells (platelets, megakaryocytes and cell lines) were lysed in a buffer composed of 12 mM Tris, 300 mM NaCl, 12 mM EDTA, containing 2 µM leupeptin, 2 mM PMSF, 5 KIU aprotinin, and 0.2% (v/v) NP40. After 20 min at 4° C. under agitation, samples were centrifuged at 13,000 g for 15 min at 4° C. and the supernatants was frozen at −80° C. Protein concentration was determined using the Bio-Rad protein assay (Bio-Rad, Ivry-sur-seine, France). For blotting experiments, proteins were further solubilized with 2% SDS for 5 min at 100° C. Proteins were separated by electrophoresis on acrylamide slab gels (Mini protean II, Bio-Rad Laboratories, Ivry-sur-seine, France) and transferred on PVDF. Membranes were soaked with 5% non-fat dry milk and incubated with $^{125}$I-Cvx (6×10$^3$ Bq/ml) in PBS pH 7.4 containing 0.1% (v/v) tween 20, or with anti-GPVI IgGs (9 µg/ml in PBS pH 8, containing 0.02% (v/v) tween 20 in the absence or the presence of 0.5 µM cold Cvx. Anti-GPVI IgGs were obtained as previously described (Jandrot-Perrus et al., 1997, *J. Biol. Chem.* 272:27035-27041) from the patient's plasma kindly provided by Pr. M. Okuma (Kyoto, Japan). Antibodies were revealed using peroxydase-coupled protein A (Amersham Pharmacia Biotech, Uppsala, Sweden) and enhanced chemiluminescence (Amersham Pharmacia Biotech, Uppsala, Sweden). For immunoprecipitations, cell lysates were precleared by incubation with protein A-sepharose at 4° C. for 30 min. and centrifugation. Cleared lysates were incubated overnight at 4° C. with 10 µg/ml polyclonal anti FcRγ chain antibodies (Upstate Biotechnology, NY) followed by the addition of protein A/G-sepharose (Pharmacia Biotech, Uppsala, Sweden) for 2 hours at room temperature. Immunoprecipitated proteins were eluted with 2% SDS and subjected to SDS-PAGE followed by blotting onto PVDF membranes and then probed using anti-GPVI and anti-FcRγ chain antibodies as described above.

Results

Figure 17:
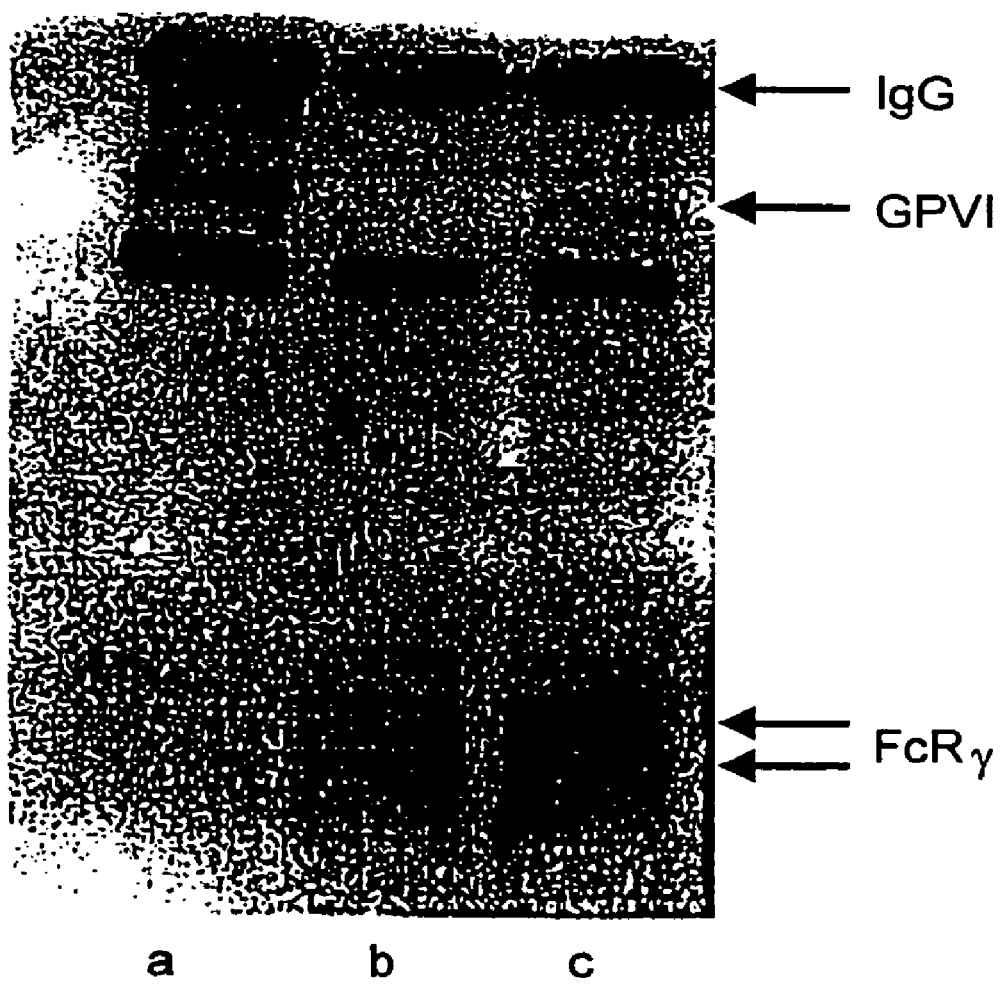
FIG. 17: Coexpression of recombinant human GPVI with FcRγ chain.

FIG. 17 shows the analysis of the precipitated proteins by immunoblotting with a mixture of anti-FcRγ antibodies and an IgG preparation containing antibodies directed against GPVI. Three bands were observed in all samples: a high molecular weight band corresponding to IgGs, a ~50 kDa non-identified band and a 14 kDa doublet corresponding to FcRγ chain. In addition, one band corresponding to GPVI is present in platelets and is also observed in U937 transduced with the GPVI virus but not in cell transduced with the control virus, indicating that recombinant GPVI is physically associated with FcRγ chain. As with FcαRI, the linkage probably involves charged residues within the transmembrane domain: R272 or R270 respectively for hGPVI and mGPVI and D11 in the FcRγ chain.

G. Inhibition of Collagen and Cvx-induced Platelet Activation by rhusGPVI:Fc

An Fc fusion human soluble GPVI (rhusGPVI:Fc) protein was produced and purified to investigate its ability to compete with membrane-bound platelet GPVI.

Materials & Methods

Protein preparation: The open-reading frame of the predicted extracellular domain of T268 was PCR amplified from the Kozak sequence before the first methionine to asparagine 269 immediately prior to the predicted transmembrane sequence. The PCR fragment was ligated into a pCDM8 host vector containing the genomic sequence of the human IgG1 Fc domain such that the extracellular part of the hGPVI cDNA was fused at its C-terminus via a 3 alanine linker to the hFc sequence. The sequenced DNA construct was transiently transfected into HEK 293T cells in 150 mm plates using Lipofectamine (Gibco/BRL, Grand Island, N.Y.) according to the manufacturer's protocol. After 72 hour post-transfection, the serum-free conditioned medium (OptiMEM, Gibco/BRL, Grand Island, N.Y.) was harvested, spun and filtered. The cells were refed with fresh medium and harvested as above a further 72 hours later. Analysis of supernatants on Western blot after reducing SDS-PAGE using an anti-human IgG Fc polyclonal antibody showed significant amounts of the recombinant human soluble GPVI fusion protein (rhusG-PVI:Fc) in the supernatants with a relative molecular mass of approximately 75-80 kDa relative to Mark 12 molecular weight standards cocktail (Novex, San Diego, Calif.).

The conditioned media was passed over a Prosep-G protein G column (10 mL, Bioprocessing Inc., Princeton, N.J.); the column was then washed with PBS, pH 7.4 and eluted with 200 mM glycine, pH 3.0 at 7 mL/min. Fractions from the 280 nm elution peak containing human rhusGPVI:Fc were pooled and dialyzed in 8000 MWCO dialysis tubing against 2 changes of 4 L PBS, pH 7.4 at 4° C. with constant stirring. The buffered exchanged material was then sterile filtered (0.2 m, Millipore Corporation, Bedford. Mass.) and frozen at −80° C.

Platelet preparation: Blood from healthy volunteers was collected by venepuncture on acid-citrate-dextrose anticoagulant (ACD-A). When needed, platelets were labeled by incubating the platelet rich plasma (PRP) with 0.6 μM ($^{14}$C) 5-hydroxytryptamine for 30 min. at 37° C. Platelet pellets were obtained by centrifugation of the platelet rich plasma (PRP) and were washed two times as previously described (Jandrot-Perrus et al., 1997, *J. Biol. Chem.* 272:27035-27041).

Platelet aggregation and secretion: Aggregation of washed platelets ($3 \times 10^8$/ml) in reaction buffer was initiated by collagen type I (Bio/Data corp, Horsham, Pa.) or Cvx. Experiments were performed with stirring at 37° C. in a Chrono-Log aggregometer (Chrono-log corp. Haverton, Pa.). Release of ($^{14}$C) 5-hydroxytryptamine was measured as described previously (Jandrot-Perrus et al., 1997, *J. Biol. Chem.* 272: 27035-27041).

Results rhusGPVI:Fc did not induce platelet aggregation or granule secretion by itself. When platelets were incubated with Cvx, addition of rhusGPVI:Fc (0.25 to 5 μg/ml) fully inhibited platelet aggregation and dense granule secretion (FIG. 18). In addition, when rhusGPVI:Fc was added to the platelet suspension prior to Cvx, it also inhibited aggregation and secretion, indicating that it could compete with platelet GPVI for Cvx (FIG. 18A). Incubation of collagen with rhusGPVI:Fc induces a loss in its ability to induce platelet aggregation and secretion (FIG. 18B). However, a tenfold higher concentration of rhusGPVI:Fc than required for Cvx was needed to produce this inhibitory effect. Furthermore, when recombinant soluble GPVI was added to platelets prior to collagen, no inhibition was observed (FIG. 18B). These results demonstrate that the extracellular domain of GPVI is active in blocking Cvx- and collagen-induced platelet aggregation.

Discussion

GPVI, despite its essential role in collagen-induced platelet aggregation, is described as having a minor role in platelet adhesion to collagen. Other receptors such as the GPIb-IX-V complex or the integrin α2β1 are major players responsible for platelet adhesion to collagen. However, immobilized Cvx is able to induce platelet adhesion indicating that GPVI may be involved in adhesion in these conditions. The above results demonstrate that expression of GPVI in U937 and FDCP-1 cells induces cell adhesion to a collagen- or Cvx-coated surface. The number of cells that bound to immobilized Cvx was significantly higher than those bound to collagen. This result indicates differences in the density of GPVI binding sites on the two surfaces. Cvx is a pure GPVI ligand and when immobilized it produces a highly reactive surface while GPVI binding sites should be disseminated on collagen fibers resulting in a less reactive surface.

Nevertheless, these results indicate that recombinant GPVI mimics the physiological function of platelet GPVI (i.e., binding to collagen). The difference in reactivity between collagen and Cvx is further emphasized by the differences in the inhibitory effect that the recombinant soluble GPVI has on collagen and Cvx-induced platelet activation. Indeed, soluble recombinant GPVI inhibits Cvx-induced platelet activation in the absence of preincubation with Cvx whilst it requires a preincubation with collagen to inhibit collagen-induced platelet activation. This probably reflects the rapid kinetics of interaction between GPVI and Cvx compared to those between GPVI and collagen. The affinity of recombinant soluble GPVI for Cvx is probably very high for two reasons: (i) soluble GPVI is expressed in a divalent Fc fusion form and (ii) Cvx is multivalent due to its hexameric structure. Thus, GPVI binding sites on collagen fibers are probably dispersed and poorly accessible. Alternatively, these observations could also suggest that binding of collagen to its other receptors, including the integrin α2β1, promotes its subsequent interaction with GPVI.

GPVI plays an important role in the development of thrombi probably because it is the receptor that appears to govern platelet activation at the contact of collagen and thus which induces platelet recruitment. Indeed, patients with GPVI deficiency or anti-GPVI-containing sera displayed bleeding disorders (see Background, above). The molecular cloning of GPVI provides the opportunity to characterize the mechanism of these deficiencies, the precise interaction between GPVI and the integrin α2β1 in collagen-induced platelet activation but also the role of GPVI in thromboembolic diseases. GPIIb-IIIa (integrin αIIb β3) is the only platelet receptor against which efficient antagonists have been so far developed (Lefkovits et al., 1995, *N. Engl. J. Med.* 332: 1553-9). Even if GPIIb-IIIa may be involved in platelet adhesion, its principal role is to bind fibrinogen allowing platelet aggregation and serving as the final common pathway of platelet thrombus formation regardless of the metabolic pathway initiating platelet activation. In contrast, GPVI is involved in an early step of platelet activation occurring immediately when platelets enter in contact with the subendothelial matrix.

GPVI represents an alternative and more specific target for new anti-thrombotic compounds. Antagonist can be directed against either of the two players, i.e., collagen GPVI binding sites or GPVI itself. Because these observations suggest that the GPVI binding sites are not easily accessible on collagen fibers, an antagonist directed against GPVI may be more efficient than an antagonist directed against collagen.

H. Bleeding Time of Mice Transplanted With Bone Marrow Cells Expressing GPVI

The results presented herein support the role of GPVI in the formation of platelet aggregates and the development of a hemostatic plug.

Materials & Methods

Isolation of Lin$^-$ bone marrow cells: Bone marrow cells were collected from mice that had been administered 150 mg/kg of 5-fluorouracil (5-FU) intravenously for four days. The cells were resuspended in phosphate buffered saline (PBS), 0.5% fetal calf serum (FCS) and incubated for 20 minutes at 4° C. with a mixture of four fluorescent fluorescein isothiocyanate (FITC)-conjugated rat monoclonal antibodies directed against mouse CD3e, CD11b, CD45R, and Ly-6G (Pharmingen, San Diego, Calif.). After labeling, cells were washed and incubated at 4° C. with anti-FITC microbeads (Miltenyi Biotech, Auburn, Calif.). After a 15 minute incubation, cells were washed, filtered through a large pore size filter and applied onto a magnetic cell sorting depletion column (types BS, Miltenyi Biotech) held onto a magnetic separator (Super MACS, Miltenyi Biotech). Depletion of the magnetically labeled cells (lineage positive) out of the bone marrow sample was done according to the manufacturer's instructions. In some experiments, Sca-1$^+$/Lin$^-$ cells were isolated using a Sca-1 multiSort Kit (Miltenyi Biotech). After separation, cells (Lin$^-$ or Sca-1$^+$/Lin$^-$) were washed and resuspended in DMEM, 10% FCS (Stem Cell Technologies, Vancouver, Canada).

Infection procedure: Isolated Lin$^-$ or Sca-1$^+$/Lin$^-$ bone marrow cells were stimulated at 37° C., 10% $CO^2$ with 10 ng/ml of recombinant mouse interleukin-3 (rmIL-3; Endogen, Woburn, Mass.), 10 ng/ml recombinant mouse interleukin-6 (rmIL-6; Endogen), 100 ng/ml recombinant mouse stem cell factor (rmSCF; R&D Systems, Inc., Mineapolis, Minn.), 100 ng/ml recombinant mouse fms-like tyrosine kinase-3 ligand (rmFlt-3 L; R&D Systems, Inc), and 1% of a conditioned medium containing mouse thrombopoietin (mTPO). The mTPO conditioned medium (containing approximately $10^4$ U/ml of mTPO) was collected from confluent MPZenTPO-virus producing cells, filtered and virus-inactivated at 56° C. for 1 hour. After two days of stimulation, bone marrow cells were infected with recombinant retrovirus containing the cDNA encoding murine full length GPVI, recombinant retrovirus containing the cDNA encoding the extracellular domain of murine GPVI, or a control retrovirus.

Bleeding assay: Infected bone marrow cells were transplanted into lethally irradiated mice, and two months post-transplantation mice were analyzed for the recovery time from a small tail vein incision. The blood flow from the incision was measured at 37° C. in saline.

Results and Discussion:

FIG. 19 depicts the bleeding time of lethally irradiated mice transplanted with bone marrow cells engineered to express full length GPVI, the extracellular domain of GPVI, or a control. Mice transplanted with bone marrow cells engineered to express the extracellular domain of GPVI, a soluble product, had the longest recovery time from a small tail vein incision. No significant difference in the recovery time from an incision in the tail vein was observed in mice transplanted with bone marrow cells engineered to express the full length GPVI from the control. These results suggest that the soluble form of GPVI inhibits the collagen-platelet interaction necessary for platelet aggregation and development of a hemostatic plug.

Uses of TANGO 268 Nucleic Acids, Polypeptides, and Modulators Thereof

As TANGO 268 was originally found in an megakaryocyte library, and in light of the fact that TANGO 268 has been shown herein to be GPVI, TANGO 268 nucleic acids, proteins, and modulators thereof can be used to modulate the proliferation, morphology, migration, differentiation, and/or function of megakaryocytes and platelets, including during development, e.g., embryogenesis. TANGO 268 nucleic acids, proteins, and modulators thereof can also be used to modulate leukocyte-platelet and platelet-endothelium interactions in inflammation and/or thrombosis. Further, TANGO 268 nucleic acids, proteins, and modulators thereof can be used to modulate platelet aggregation and degranulation. For example, antagonists to TANGO 268 action, such as peptides, antibodies or small molecules that decrease or block TANGO 268 binding to extracellular matrix components (e.g., collagen or integrins) or antibodies preventing TANGO 268 signaling, can be used as collagen or platelet release and aggregation blockers. In a specific example, a polypeptide comprising the extracellular domain of TANGO 268 can be used to decrease or block TANGO 268 binding to extracellular matrix components (i.e., collagen), or to prevent platelet aggregation. In another example, agonists that mimic TANGO 268 activity, such as peptides, antibodies or small molecules, can be used to induce platelet release and aggregation.

In further light of the fact that TANGO 268 represents GPVI, and its expression is restricted to cells of the megakaryocyte lineage, TANGO 268 nucleic acids, proteins, and modulators thereof can be used to modulate disorders associated with abnormal or aberrant megakaryocyte and/or platelet proliferation, differentiation, morphology, migration, aggregation, degranulation and/or function. Examples of these disorders include, but are not limited to, bleeding disorders (e.g., bleeding tendency and/or prolonged bleeding time) such as thrombocytopenia (e.g., idiopathic thrombocytopenic purpura (ITP) or immune thrombocytopenia or thrombocytopenia induced by chemotherapy or radiation therapy).

As TANGO 268 represents GPVI, and GPVI is a component in processes involving platelet binding to the vascular subendothelium, platelet activation and inflammation processes, TANGO 268 nucleic acids, proteins, and modulators thereof can be used to modulate thrombotic disorders (e.g., thrombotic occlusion of coronary arteries), hemorrhagic disorders, diseases exhibiting quantitative or qualitative platelet dysfunction and diseases displaying endothelial dysfunction (endotheliopathies). These diseases include, but are not limited to, coronary artery and cerebral artery diseases. Further, TANGO 268 nucleic acids, proteins, and modulators thereof can be used to modulate cerebral vascular diseases, including stroke and ischemia, venous thromboembolism diseases (e.g., diseases involving leg swelling, pain and ulceration, pulmonary embolism, abdominal venous thrombosis), thrombotic microangiopathies, vascular purpura, and GPVI deficiencies as described, e.g., in Moroi and Jung, 1997, *Thrombosis and Haemostasis* 78:439-444. TANGO 268 nucleic acids, proteins, and modulators thereof can be used to modulate symptoms associated with platelet disorders and/or diseases (e.g., bleeding disorders). In particular, TANGO 268 nucleic acids, proteins, and modulators thereof can be used to modulate symptoms associated with ITP such as purpura and severe bleeding problems.

As GPVI has been shown to be important for platelet adhesion and aggregation, and platelet adhesion and aggregation play an important role in acute coronary diseases, TANGO 268 nucleic acids, proteins and modulators thereof can be used to modulate coronary diseases (e.g., cardiovascular diseases including unstable angina pectoris, myocardial infarction, acute myocardial infarction, coronary artery disease, coronary revascularization, coronary restenosis, ventricular thromboembolism, atherosclerosis, coronary artery disease (e.g., arterial occlusive disorders), plaque formation, cardiac ischemia, including complications related to coronary procedures, such as percutaneous coronary artery angioplasty (balloon angioplasty) procedures). With respect to coronary procedures, such modulation can be achieved via administration of GPVI modulators prior to, during, or subsequent to the procedure. In a preferred embodiment, such administration can be utilized to prevent acture cardiac ischemia following angioplasty.

TANGO 268 nucleic acids, proteins and modulators thereof can, therefore, be used to modulate disorders resulting from any blood vessel insult that can result in platelet aggregation. Such blood vessel insults include, but are not limited to, vessel wall injury, such as vessel injuries that result in a highly thrombogenic surface exposed within an otherwise intact blood vessel e.g., vessel wall injuries that result in release of ADP, thrombin and/or epinephrine, fluid shear stress that occurs at the site of vessel narrowing, ruptures and/or tears at the sites of atherosclerotic plaques, and injury resulting from balloon angioplasty or atherectomy.

Preferably, the TANGO 268 nucleic acids, proteins and modulators (e.g., anti-TANGO 268 antibodies) thereof do not effect initial platelet adhesion to vessel surfaces, or effect such adhesion to a relatively lesser extent than the effect on platelet-platelet aggregation, e.g., unregulated platelet-platelet aggregation, following the initial platelet adhesion. Further, in certain embodiments, it is preferred that the TANGO 268 nucleic acids, proteins and modulators (e.g., anti-TANGO 268 antibodies) thereof do not effect other platelet attributes or functions, such as agonist-induced platelet shape change (e.g., GPIb-vWF-mediated platelet agglutination induced by ristocetin), release of internal platelet granule components, activation of signal transduction pathways or induction of calcium mobilization upon platelet activation.

Further, polymorphisms associated with particular TANGO 268 alleles, such as those in platelet receptor glycoprotein Ia/IIa that are associated with risk of coronary disease (see, e.g., Moshfegh et al., 1999, *Lancet* 353:351-354), can be used as a marker to diagnose abnormal coronary function (e.g., coronary diseases such as myocardial infarction, atherosclerosis, coronary artery disease, plaque formation).

In further light of the fact that TANGO 268 is GPVI, TANGO 268 nucleic acids, proteins and modulators thereof can be used to modulate disorders associated with aberrant signal transduction in response to collagen or other extracellular matrix proteins.

In addition to the above, TANGO 268 nucleic acids, proteins and modulators thereof can be utilized to modulate disorders associated with aberrant levels of TANGO 268 expression and/or activity either in cells that normally express TANGO 268 or in cells that do not express TANGO 268. For example, TANGO 268 nucleic acids, proteins and modulators thereof can be used to modulate disorders associated with aberrant expression of TANGO 268 in cancerous (e.g., tumor) cells that do not normally express TANGO 268. Such disorders can include, for example, ones associated with tumor cell migration and progression to metastasis.

In light of the fact that TANGO 268 (i.e., GPVI) has been shown to interact with collagen, and the progression, migration and metastasis of cancer cells has been shown to correlate with the attachment of cancer cells to interstitial collagen (see, e.g., Martin et al., 1996, *Int. J. Cancer* 65:796-804), abnormal and/or aberrant TANGO 268 expression (e.g., expression of TANGO 268 in cells, such as tumor cells, that do not normally express it or increased expression of TANGO 268 in cells that do normally express it) can be used as a marker for the progression, migration and metastasis of cancerous cells. In particular, abnormal and/or aberrant TANGO 268 expression can be used as a marker for the progression, migration and metastasis of colon cancer and liver cancer.

In light of TANGO 268 exhibiting homology to human monocyte inhibitory receptor, TANGO 268 nucleic acids, proteins and modulators thereof can be used mediate the downregulation of cell activation via phosphatases. In light of TANGO 268 containing two Ig-like domains, TANGO 268 nucleic acids, proteins and modulators thereof can be used to modulate immunoregulatory functions. Further, as TANGO 268 is expressed in the liver, embryo, bone marrow, and peripheral blood, TANGO 268 nucleic acids, proteins, and modulators thereof can be used to treat disorders of these cells, tissues or organs, e.g., liver disorders and immunological disorders.

TANGO 268 is expressed on the surface of platelets. As such, a cellular and therapeutic target of modulators of TANGO 268 (e.g., anti-TANGO 268 antibodies) is readily available for testing and analysis (e.g., for in vitro testing and analysis). This coupled with the availability of several different relevant platelet assays (see below) provides an unusual drug development opportunity for TANGO 268 modulators. For example, the in vivo pharmacodynamic characterization of TANGO 268 modulators can be facilitated via the availability of various platelet assays (e.g., prolongation of bleeding time, quantitative measurement of TANGO 268 receptor blockade, inhibition of ex vivo platelet aggregation) that can be correlated with each other to permit more effective assessment of a modulator's functional consequences. The correlation available for such assays, therefore, allows for the in vitro characterization of a TANGO 268 modulator to more directly apply to the measurement of the modulator's therapeutic effect.

In addition to utilizing the availability of platelets and platelet assays for assessing the therapeutic efficacy, including clinical efficacy, of a TANGO 268 modulator, this availability can also be utilized for preclinical drug development aspects such as determining modulator dosage response, toxicology, magnitude of effect (e.g., magnitude of initial effect and magnitude of effect's duration), function, specificity (e.g., specificity with respect to particular platelet functions), receptor specificity, and species specificity (which, in turn, can identify appropriate animal models for pharmacology studies).

Modulators of TANGO 268 platelet aggregation can also be utilized, e.g., for ex vivo procedures, e.g., ex vivo inhibition of platelet aggregation.

Assays for the Detection of TANGO 268 Expression or Activity

The expression of TANGO 268 can be readily detected, e.g., by quantifying TANGO 268 protein and/or RNA. Many methods standard in the art can be thus employed, including, but not limited to, immunoassays to detect and/or visualize gene expression (e.g., Western blot, immunoprecipitation followed by sodium dodecyl sulfate polyacrylamide gel electrophoresis (SDS-PAGE), immunocytochemistry, etc) and/or hybridization assays to detect gene expression by detecting and/or visualizing respectively mRNA encoding a gene (e.g., Northern assays, dot blots, in situ hybridization, etc), etc. Ligand binding assays, such as described above, can be performed to assess the function of TANGO 268.

The activity of a TANGO 268 protein can be measured by employing methods known to those of skill in the art. For example, the activity of a TANGO 268 protein can be analyzed by treating of platelets or TANGO 268-transfected cells with collagen or convulxin and measuring the effect of such treatment on the level of tyrosine phosphorylation of signaling molecules, such as FcRγ, Syk, and PLCγ2 (e.g., tyrosine phosphorylation can be detected by immunoprecipitation followed by SDS-PAGE, kinase assays, etc.). The activity of a TANGO 268 protein can also be analyzed by measuring changes in the concentration of free intracellular $Ca^{2+}$ induced by the treatment of platelets or TANGO 268 transfected cells with collagen or convulxin. Briefly, platelets or TANGO 268 transfected cells are incubated with fura-2 fluorescence at 37° C. and, then incubated with 2 mM $CaCl_2$ prior to incubation with convulxin, collagen or thrombin (an agent that does not activate TANGO 268). The cells are lysed in lysis buffer, and the concentration of free intracellular $Ca^{2+}$ is measured by fluorescence at 37° C. using a spectrophotometer (see, e.g., Jandrot-Perrus et al., 1997, *J. of Biol. Chem.* 272:27035-27041).

The activity of a TANGO 268 protein can also be analyzed by a platelet adhesion assay. Briefly, the adhesion assay is performed as follows: $^{51}$Cr-labeled platelets are incubated in microtiter plates that have collagen, convulxin or BSA immobilized to the surface of the wells, the cells are washed, 2% SDS is added to each well, and the number of adherent platelets is determined by counts for $^{51}$Cr using a scintillation counter (see, e.g., Jandrot-Perrus et al., 1997, *J. of Biol. Chem.* 272:27035-27041). Further, the activity of a TANGO 268 protein can be analyzed by platelet aggregation assays or secretion assays known to those of skill in the art (see, e.g., Moroi et al., 1989, *J. Clin. Invest.* 84:1440-1445 and Poole et al., 1997, *EMBO J.* 16(9):2333-2341). Briefly, the platelet aggregation is performed as follows: platelets are incubated with collagen or convulxin in a cuvette at 37° C. while being stirred, and the cell suspension is monitored by a lumiaggregometer.

Such assays may be utilized as part of TANGO 268 diagnostic assays. In addition, such assays may be utilized as part of screening methods for identifying compounds that modulate the activity and/or expression of TANGO 268.

Assays for the Function of TANGO 268

The function of a TANGO 268 protein can be analyzed by transplanting hematopoietic cells engineered to express TANGO 268 or a control into lethally irradiated mice. The affect of TANGO 268 expression on the function, development and proliferation of hematopoietic cells, specifically platelets, can be determined by comparing mice transplanted with hematopoietic cells expressing TANGO 268 to mice transplanted with hematopoietic cells expressing a control. For example, the role of TANGO 268 in platelet aggregation can be analyzed by transplanting mice with hematopoietic cells engineered to express TANGO 268 or fragments thereof. The irradiated mice may be normal, transgenic or knockout mice, and the hematopoietic cells may be obtained from normal, transgenic or knockout mice.

The efficacy of using TANGO 268 nucleic acids, proteins or modulators thereof to modulate the expression of a given gene can be analyzed using irradiated mice transplanted with hematopoietic cells engineered to express TANGO 268 or modulators thereof. The affect of TANGO 268 nucleic acids, proteins or modulators thereof on the expression of a gene of interest can be measured by analyzing the RNA or protein levels of the gene of interest. Techniques known to those of skill can be used to measure RNA and protein levels in vivo and in vitro. For example, RNA expression can be detected in vivo by in situ hybridization. Further, the efficacy of using TANGO 268 nucleic acids, proteins or modulators thereof to treat, inhibit or prevent a particular disease or disorder can be analyzed by using irradiated mouse or rat models of a disease or disorder transplanted with hematopoietic cells engineered to express TANGO 268 or modulators thereof.

Assays for Analysis of TANGO 268 Modulators

A variety of assays can be utilized to analyze a TANGO 268 protein, nucleic acid or modulator thereof. Such assays can include in vivo, ex vivo and in vitro assays, as described herein. See, also, e.g., Loscalzo and Schaefer (eds), 1998, Thrombosis and Hemorrhage $2^{nd}$ Edition, Chapter 16, Williams and Wilkins: Baltimore, Md.; Horton (ed), 1995, Adhesion Receptors as Therapeutic Targets, Chapter 15, CRC Press, Inc.: London, United Kingdom, and U.S. Pat. No. 5,976,532.

For example, in view of the fact that TANGO 268 is a cell surface receptor, in particular, a platelet receptor, standard quantitative binding studies can be utilized to measure modulator binding to platelets. Horton (ed), 1995, Adhesion Receptors as Therapeutic Targets, Chapter 15, CRC Press, Inc.: London, United Kingdom. Such binding assays can also be utilized to perform receptor blockade studies to measure the number of cellular sites available for binding modulator by comparing the number of molecules of labeled modulator molecules (e.g., labeled anti-TANGO 268 antibodies) bound per platelet at a series of concentrations with the number of modulator molecules bound at saturation. See, e.g., Coller et al., 1985, J. Clin. Invest. 76: 101 or U.S. Pat. No. 5,854,005.

The reversibility of modulator molecule (e.g., anti-TANGO 268 antibodies) binding on platelets can also be tested, using, e.g., techniques such as those described in Coller et al., 1985, J. Clin. Invest. 76: 101, and U.S. Pat. No. 5,976,532. In addition, under non-competitive conditions, the rate of modulator dissociation can be assessed by, e.g., flow cytometry analysis of platelets when fluorescently labeled modulator (e.g., anti-TANGO 268 antibody)-coated platelets are mixed with an equal number of untreated platelets and incubated at physiological temperature. In instances wherein appreciable reversibility indicates that inhibitory effects of single in vivo injection can be relatively short-lived, suggesting that an administration regimien involving an initial bolus followed by continuous infusion may be most effective.

In vitro and ex vivo assays for inhibition of platelet aggregation can also be utilized. Such assays are well known to those of skill in the art and include, but are not limited to the turbidometric method, in which aggregation is measured as an increase in transmission of visible light through a stirred or agitated platelet suspension. See, e.g., Chanarin, L., 1989, Laboratory Haematology, Chapter 30, Churchill, Livingstone, London; and Schmidt, R. M. (ed), 1979, CRC Handbook Series in Clinical Laboratory Science, CRC Press, Inc.: Boca Raton, Fla.

Platelet aggregation can also be assayed via methods such as those described in U.S. Pat. No. 5,976,532. For example, in a non-limiting example of such a method, the platelet concentration in platelet-rich plasma obtained (PRP) obtained from normal or patient blood samples is adjusted to 200,000 to 300,000/mm$^3$. In an in vitro assay, the PRP is aliquoted and incubated in the presence or absence of a TANGO 268 modulator (e.g., an anti-GPVI antibody) for a period of time (e.g., 15 minutes at 37° C.) prior to the addition of a platelet inducing agonist (e.g., ADP, thrombin, collagen, epinephrine, and ristocetin). In an ex vivo assay, the PRP obtained from individuals treated with TANGO 268 or a placebo is aliquoted and incubated in the presence of a platelet inducing agonist (e.g., ADP, thrombin, collagen, epinephrine, and ristocetin). Platelet aggregation is measured by assessing an increase in the transmission of visible light through a platelet suspension using a spectrophotometer.

In certain embodiments, it is preferred that the TANGO 268 modulator not effect platelet attributes or functions other than platelet aggregation. Such other platelet attributes or functions, include, for example, agonist-induced platelet shape change (e.g., GPIb-vWF-mediated platelet agglutination induced by ristocetin), release of internal platelet granule components, activation of signal transduction pathways or induction of calcium mobilization upon platelet activation. Assays for these platelet attributes and functions are well known to those of skill in the art and can be utilized to routinely test, develop and identify TANGO 268 modulators exhibiting a specificity for modulation of platelet aggregation.

The shape of a platelet can be analyzed in any in vitro assay known to those of skill in the art. Briefly, platelets are contacted in the presence or absence of a TANGO 268 modulator with a platelet inducing agonist (e.g., ADP, thrombin, collagen, epinephrine, and ristocetin) and the shape of the platelets are assessed by microscopy or by flow cytometry. Platelet degranulation can be analyzed, for example, by measuring the presence of ATP in vitro following stimulation with a platelet inducing agonist in the presence or absence of a TANGO 268 modulator (see, e.g., Loscalzo and Schaefer (eds), 1998, Thrombosis and Hemorrhage $2^{nd}$ Edition, Chapter 16, Williams and Wilkins: Baltimore, Md.). The activation of platelet signal transduction pathways can be analyzed in in vitro and ex vivo assays using assays known to those of skill in the art. For example, the activation of signal transduction pathways in vitro can be analyzed by contacting platelet-rich plasma samples with platelet agonists (e.g., collagen and convulxin) in the presence or absence of a TANGO 268 modulator and measuring the effect of such treatment on the level of tyrosine phosphorylation of signaling molecules, such as FcRγ, Syk, and PLCγ 2 (e.g., tyrosine phosphorylation can be detected by immunoprecipitation followed by SDS-PAGE, kinase assays, etc.). In an ex vivo assay, the activation of signal transduction pathways can be analyzed by contacting platelet-rich plasma samples obtained from individuals treated with TANGO 268 or a placebo with a platelet agonist (e.g., collagen and convulxin) and measuring the effect of such treatment on the level of tyrosine phosphorylation of signaling molecules, such as FcRγ, Syk, and PLCγ 2 (e.g., tyrosine phosphorylation can be detected by immunoprecipitation followed by SDS-PAGE, kinase assays, etc.). The effect of platelet activation on calcium mobilization can also be analyzed by measuring changes in the concentration of free intracellular $Ca^{2+}$ induced in in vitro and ex vivo assays using assays known to those of skill in the art. Briefly, platelet-rich platelets are incubated with fura-2 fluorescence at 37° C. and then incubated with 2 mM $CaCl_2$ in the presence or absence of a TANGO 268 modulator prior to incubation with a platelet agonist (e.g., convulxin, collagen and thrombin). The cells are lysed in lysis buffer, and the concentration of free intracellular $Ca^{2+}$ is measured by fluorescence at 37° C. using a spectrophotometer (see, e.g., Jandrot-Perrus et al., 1997, *J. of Biol. Chem.* 272:27035-27041).

Other assays for platelets include, in vivo assays such as assessment of prolongation of bleeding time. For example, the bleeding time resulting from an injury (e.g., a small tail vein incision) in an animal model treated with a TANGO 268 modulator can be compared to an animal model treated with a placebo. In humans, the number of bleeding episodes and the length of the bleeding time during a bleeding episode for a human treated with a TANGO 268 modulator can be compared to a human treated with a placebo.

The efficacy of TANGO 268 modulators can be assessed in a variety of animal models of arterial thrombosis, including, but not limited to, the Folts model, the electrolytic injury model, the thrombin-induced arterial thrombosis model, and a model of acute thrombosis resulting from injury induced by coronary balloon angioplasty (see, e.g., Loscalzo and Schaefer (eds), 1998, Thrombosis and Hemorrhage $2^{nd}$ Edition, Chapter 16, Williams and Wilkins: Baltimore, Md.). The Folts model, which is the most widely used animal model of coronary and carotid artery thrombosis, is produced by mechanical concentric vessel narrowing using a cylinder placed around the artery. The electrolytic model, which is used for deep arterial injury, is produced by introducing an electric current via an electrode to the intimal layer of a stenosed vessel. By applying species specificity data that can readily be obtained using, e.g., the platelet aggregation assays described herein, animal models particularly well suited to study of any given TANGO 268 modulator can be chosen.

Tables 1 and 2 below provide a summary of the sequence information for TANGO 268.

TABLE 1

Summary of TANGO 268 Sequence Information

| Gene | cDNA | ORF | Figure | Accession Number |
|---|---|---|---|---|
| Human TANGO 268 | SEQ ID NO: 1 | SEQ ID NO: 2 | FIGS. 1A-1B | 207180 |
| Mouse TANGO 268 | SEQ ID NO: 14 | SEQ ID NO: 15 | FIG. 6 | PTA-225 |

TABLE 2

Summary of Domains of TANGO 268 Proteins

| Protein | Signal Sequence | Mature Protein | Extracellular | Ig-like | Transmembrane | Cytoplasmic |
|---|---|---|---|---|---|---|
| HUMAN TANGO 268 | aa 1-20 of SEQ ID NO: 3 (SEQ ID NO: 4) | aa 21-339 of SEQ ID NO: 3 (SEQ ID NO: 5) | aa 21-269 of SEQ ID NO: 3 (SEQ ID NO: 9) | aa 48-88; 134-180 of SEQ ID NO: 3 (SEQ ID NO: 6; SEQ ID NO: 7) | aa 270-288 of SEQ ID NO: 3 (SEQ ID NO: 8) | aa 289-339 of SEQ ID NO: 3 (SEQ ID NO: 10) |
| MOUSE TANGO 268 | aa 1-21 of SEQ ID NO: 16 (SEQ ID NO: 17) | aa 22-313 of SEQ ID NO: 16 (SEQ ID NO: 18) | aa 22-267 of SEQ ID NO: 16 (SEQ ID NO: 19) | aa 49-89; 135-181 of SEQ ID NO: 16 (SEQ ID NO: 22; SEQ ID NO: 23) | aa 268-286 of SEQ ID NO: 16 (SEQ ID NO: 20) | aa 287-313 of SEQ ID NO: 16 (SEQ ID NO: 21) |

Various aspects of the invention are described in further detail in the following subsections:

I. Isolated Nucleic Acid Molecules

One aspect of the invention pertains to isolated nucleic acid molecules that encode a polypeptide of the invention or a biologically active portion thereof, as well as nucleic acid molecules sufficient for use as hybridization probes to identify nucleic acid molecules encoding a polypeptide of the invention and fragments of such nucleic acid molecules suitable for use as PCR primers for the amplification or mutation of nucleic acid molecules. As used herein, the term "nucleic acid molecule" is intended to include DNA molecules (e.g., cDNA or genomic DNA) and RNA molecules (e.g., mRNA)

and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. Preferably, an "isolated" nucleic acid molecule is free of sequences (preferably protein encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. As used herein, the term "isolated" when referring to a nucleic acid molecule does not include an isolated chromosome.

A nucleic acid molecule of the present invention, e.g., a nucleic acid molecule having the nucleotide sequence of SEQ ID NO:1, 2, 14, or 15 or a complement thereof, can be isolated using standard molecular biology techniques and the sequence information provided herein. Using all or a portion of the nucleic acid sequences of SEQ ID NO:1, 2, 14 or 15 as a hybridization probe, nucleic acid molecules of the invention can be isolated using standard hybridization and cloning techniques (e.g., as described in Sambrook et al., eds., *Molecular Cloning: A Laboratory Manual*, 2nd ed., *Cold Spring Harbor Laboratory*, Cold Spring Harbor Laboratory Press, Cold Spring Harbor, N.Y., 1989).

A nucleic acid molecule of the invention can be amplified using cDNA, mRNA or genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to all or a portion of a nucleic acid molecule of the invention can be prepared by standard synthetic techniques, e.g., using an automated DNA synthesizer.

In another preferred embodiment, an isolated nucleic acid molecule of the invention comprises a nucleic acid molecule which is a complement of the nucleotide sequence of SEQ ID NO:1, 2, 14 or 15 or a portion thereof. A nucleic acid molecule which is complementary to a given nucleotide sequence is one which is sufficiently complementary to the given nucleotide sequence that it can hybridize to the given nucleotide sequence thereby forming a stable duplex.

Moreover, a nucleic acid molecule of the invention can comprise only a portion of a nucleic acid sequence encoding a full length polypeptide of the invention for example, a fragment which can be used as a probe or primer or a fragment encoding a biologically active portion of a polypeptide of the invention. The nucleotide sequence determined from the cloning one gene allows for the generation of probes and primers designed for use in identifying and or cloning homologues in other cell types, e.g., from other tissues, as well as homologues from other mammals. The probe/primer typically comprises substantially purified oligonucleotide. In one embodiment, the oligonucleotide comprises a region of nucleotide sequence that hybridizes under stringent conditions to at least about 12, preferably about 25, more preferably about 50, 75, 100, 125, 150, 175, 200, 250, 300, 350 or 400 consecutive nucleotides of the sense or anti-sense sequence of SEQ ID NO:1, 2, 14 or 15 or of a naturally occurring mutant of SEQ ID NO:1, 2, 14 or 15. In another embodiment, the oligonucleotide comprises a region of nucleotide sequence that hybridizes under stringent conditions to at least 400, preferably 450, 500, 530, 550, 600, 700, 800, 900, 1000 or 1150 consecutive oligonucleotides of the sense or antisense sequence of SEQ ID NO:1, 2, 14 or 15 of a naturally occurring mutant of SEQ ID:1,2 14 or 15.

Probes based on the sequence of a nucleic acid molecule of the invention can be used to detect transcripts or genomic sequences encoding the same protein molecule encoded by a selected nucleic acid molecule. The probe comprises a label group attached thereto, e.g., a radioisotope, a fluorescent compound, an enzyme, or an enzyme co-factor. Such probes can be used as part of a diagnostic test kit for identifying cells or tissues which mis-express the protein, such as by measuring levels of a nucleic acid molecule encoding the protein in a sample of cells from a subject, e.g., detecting mRNA levels or determining whether a gene encoding the protein has been mutated or deleted.

A nucleic acid fragment encoding a biologically active portion of a polypeptide of the invention can be prepared by isolating a portion of any of SEQ ID NO:3 or 16 expressing the encoded portion of the polypeptide protein (e.g., by recombinant expression in vitro) and assessing the activity of the encoded portion of the polypeptide.

The invention further encompasses nucleic acid molecules that differ from the nucleotide sequence of SEQ ID NO:1, 2, 14 or 15 due to degeneracy of the genetic code and thus encode the same protein as that encoded by the nucleotide sequence of SEQ ID NO:3 or 16.

In addition to the nucleotide sequences of SEQ ID NO:3 or 16, it will be appreciated by those skilled in the art that DNA sequence polymorphisms that lead to changes in the amino acid sequence may exist within a population (e.g., the human population). Such genetic polymorphisms may exist among individuals within a population due to natural allelic variation. An allele is one of a group of genes which occur alternatively at a given genetic locus. For example, human TANGO 268 has been mapped to chromosome 19, and therefore TANGO 268 family members can include nucleotide sequence polymorphisms (e.g., nucleotide sequences that vary from SEQ ID NO:1 and SEQ ID NO:2) that map to this chromosomal locus (e.g., region of chromosome 19q13) and such sequences represent TANGO 268 allelic variants. As used herein, the phrase "allelic variant" refers to a nucleotide sequence which occurs at a given locus or to a polypeptide encoded by the nucleotide sequence. As used herein, the terms "gene" and "recombinant gene" refer to nucleic acid molecules comprising an open reading frame encoding a polypeptide of the invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention. In one embodiment, polymorphisms that are associated with a particular disease and/or disorder are used as markers to diagnose said disease or disorder. In a preferred embodiment, polymorphisms are used as a marker to diagnose abnormal coronary function (e.g., coronary diseases such as myocardial infarction, atherosclerosis, coronary artery disease, plaque formation).

Moreover, nucleic acid molecules encoding proteins of the invention from other species (homologues), which have a nucleotide sequence which differs from that of the human or mouse protein described herein are intended to be within the scope of the invention. Nucleic acid molecules corresponding to natural allelic variants and homologues of a cDNA of the invention can be isolated based on their identity to the human nucleic acid molecule disclosed herein using the human cDNAs, or a portion thereof, as a hybridization probe according to standard hybridization techniques under stringent hybridization conditions. For example, a cDNA encoding a soluble form of a membrane-bound protein of the invention isolated based on its hybridization to a nucleic acid molecule encoding all or part of the membrane-bound form. Likewise, a cDNA encoding a membrane-bound form can be isolated based on its hybridization to a nucleic acid molecule encoding all or part of the soluble form.

Accordingly, in another embodiment, an isolated nucleic acid molecule of the invention is at least 500, 600, 700, 800, 900, 1000, 1100, 1200, 1300, 1400, 1500, 1600, 1700, 1800, 1900 or 2000 nucleotides in length and hybridizes under stringent conditions to the nucleic acid molecule comprising the nucleotide sequence, preferably the coding sequence, of SEQ ID NO:1, or a complement thereof.

Accordingly, in another embodiment, an isolated nucleic acid molecule of the invention is at least 50, 100, 200, 300, 400, 500, 600, 700, 800 or 900 nucleotides in length and hybridizes under stringent conditions to the nucleic acid molecule comprising the nucleotide sequence, preferably the coding sequence, of SEQ ID NO:2, or a complement thereof.

Accordingly, in another embodiment, an isolated nucleic acid molecule of the invention is at least 50, 100, 200, 300, 400, 500, 600, 700, 800, 900, 1000, 1100, 1200, 1300, 1400 or 1500 nucleotides in length and hybridizes under stringent conditions to the nucleic acid molecule comprising the nucleotide sequence, preferably the coding sequence, of SEQ ID NO:14, or a complement thereof.

Accordingly, in another embodiment, an isolated nucleic acid molecule of the invention is at least 50, 100, 200, 300, 400, 500, 600, 700, 800 or 900 nucleotides in length and hybridizes under stringent conditions to the nucleic acid molecule comprising the nucleotide sequence, preferably the coding sequence, of SEQ ID NO:15, or a complement thereof.

As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in *Current Protocols in Molecular Biology*, John Wiley & Sons, N.Y. (1989), 6.3.1-6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50-65° C. Preferably, an isolated nucleic acid molecule of the invention that hybridizes under stringent conditions to the sequence of SEQ ID NO:1, 2, 14 or 15, or a complement thereof, corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of a nucleic acid molecule of the invention sequence that may exist in the population, the skilled artisan will further appreciate that changes can be introduced by mutation thereby leading to changes in the amino acid sequence of the encoded protein, without altering the biological activity of the protein. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologues of various species may be non-essential for activity and thus would be likely targets for alteration. Alternatively, amino acid residues that are conserved among the homologues of various species (e.g., mouse and human) may be essential for activity and thus would not be likely targets for alteration.

Accordingly, another aspect of the invention pertains to nucleic acid molecules encoding a polypeptide of the invention that contain changes in amino acid residues that are not essential for activity. Such polypeptides differ in amino acid sequence from SEQ ID NO:3, yet retain biological activity. In one embodiment, the isolated nucleic acid molecule includes a nucleotide sequence encoding a protein that includes an amino acid sequence that is at least about 30%, 35%, 40%, 45%, 50%, 55%, 60%, 65%, 75%, 85%, 95%, or 98% identical to the amino acid sequence of SEQ ID NO:3.

Accordingly, another aspect of the invention pertains to nucleic acid molecules encoding a polypeptide of the invention that contain changes in amino acid residues that are not essential for activity. Such polypeptides differ in amino acid sequence from SEQ ID NO:16, yet retain biological activity. In one embodiment, the isolated nucleic acid molecule includes a nucleotide sequence encoding a protein that includes an amino acid sequence that is at least about 30%, 35%, 40%, 45%, 50%, 55%, 60%, 65%, 75%, 85%, 95%, or 98% identical to the amino acid sequence of SEQ ID NO:16.

An isolated nucleic acid molecule encoding a variant protein can be created by introducing one or more nucleotide substitutions, additions or deletions into the nucleotide sequence of SEQ ID NO:1, 2, 14 or 15 such that one or more amino acid substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

In a preferred embodiment, a mutant polypeptide that is a variant of a polypeptide of the invention can be assayed for: (1) the ability to form protein: protein interactions with proteins in a signaling pathway of the polypeptide of the invention; (2) the ability to bind a ligand of the polypeptide of the invention; or (3) the ability to bind to an intracellular target protein of the polypeptide of the invention. In yet another preferred embodiment, the mutant polypeptide can be assayed for the ability to modulate cellular proliferation, cellular migration or chemotaxis, or cellular differentiation.

The present invention encompasses antisense nucleic acid molecules, i.e., molecules which are complementary to a sense nucleic acid encoding a polypeptide of the invention, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire coding strand, or to only a portion thereof, e.g., all or part of the protein coding region (or open reading frame). An antisense nucleic acid molecule can be antisense to all or part of a non-coding region of the coding strand of a nucleotide sequence encoding a polypeptide of the invention. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45 or 50 nucleotides or more in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a selected polypeptide of the invention to thereby inhibit expression, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330).

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585-591)) can be used to catalytically cleave mRNA transcripts to thereby inhibit translation of the protein encoded by the mRNA. A ribozyme having specificity for a nucleic acid molecule encoding a polypeptide of the invention can be designed based upon the nucleotide sequence of a cDNA disclosed herein. For example, a derivative of a *Tetrahymena* L-19 IVS RNA can be constructed in which the nucleotide sequence of the active site is complementary to the nucleotide sequence to be cleaved in a Cech et al. U.S. Pat. No. 4,987,071; and Cech et al. U.S. Pat. No. 5,116,742. Alternatively, an mRNA encoding a polypeptide of the invention can be used to select a catalytic RNA having a specific ribonuclease activity from a pool of RNA molecules. See, e.g., Bartel and Szostak (1993) *Science* 261:1411-1418.

The invention also encompasses nucleic acid molecules which form triple helical structures. For example, expression of a polypeptide of the invention can be inhibited by targeting nucleotide sequences complementary to the regulatory region of the gene encoding the polypeptide (e.g., the promoter and/or enhancer) to form triple helical structures that prevent transcription of the gene in target cells. See generally Helene (1991) *Anticancer Drug Des.* 6(6):569-84; Helene (1992) *Ann. N.Y. Acad. Sci.* 660:27-36; and Maher (1992) *Bioassays* 14(12):807-15.

In various embodiments, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93: 14670-675.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup (1996), supra; or as probes or primers for DNA sequence and hybridization (Hyrup (1996), supra; Perry-O'Keefe et al. (1996) *Proc. Natl. Acad. Sci. USA* 93: 14670-675).

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996), supra). The synthesis of PNA-DNA chimeras can be performed as described in Hyrup (1996), supra, and Finn et al. (1996) *Nucleic Acids Res.* 24(17):3357-63. For example, a DNA chain can be synthesized on a solid support using standard phosphoramidite coupling chemistry and modified nucleoside analogs. Compounds such as 5'-(4-methoxytrityl) amino-5'-deoxy-thymidine phosphoramidite can be used as a link between the PNA and the 5' end of DNA (Mag et al. (1989) *Nucleic Acids Res.* 17:5973-88). PNA monomers are then coupled in a stepwise manner to produce a chimeric molecule with a 5' PNA segment and a 3' DNA segment (Finn et al. (1996) *Nucleic Acids Res.* 24(17):3357-63). Alternatively, chimeric molecules can be synthesized with a 5' DNA segment and a 3' PNA segment (Peterser et al. (1975) *Bioorganic Med. Chem. Lett.* 5:1119-11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553-6556; Lemaitre et al. (1987) *Proc. Natl. Acad. Sci. USA* 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al. (1988) *Bio/Techniques* 6:958-976) or intercalating agents (see, e.g., Zon (1988) *Pharm. Res.* 5:539-549). To this end, the oligonucleotide may be conjugated to another molecule, e.g., a peptide, hybridization triggered cross-linking agent, transport agent, hybridization-triggered cleavage agent, etc.

II. Isolated Proteins and Antibodies

One aspect of the invention pertains to isolated proteins, and biologically active portions thereof, as well as polypeptide fragments suitable for use as immunogens to raise antibodies directed against a polypeptide of the invention. In one embodiment, the native polypeptide can be isolated from cells or tissue sources by an appropriate purification scheme using standard protein purification techniques. In another embodiment, polypeptides of the invention are produced by recombinant DNA techniques. Alternative to recombinant expression, a polypeptide of the invention can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a polypeptide of the invention include polypeptides comprising amino acid sequences sufficiently identical to or derived from the amino acid sequence of the protein (e.g., the amino acid sequence shown in any of SEQ ID NO:6, 7, 9, 10, 19, 20, 21, 22 or 23, which include fewer amino acids than the full length protein, and exhibit at least one activity of the corresponding full-length protein. Typically, biologically active portions comprise a domain or motif with at least one activity of the corresponding protein. A biologically active portion of a protein of the invention can be a polypeptide which is, for example, 10, 25, 50, 100 or more amino acids in length. Moreover, other biologically active portions, in which other regions of the protein are deleted, can be prepared by recombinant techniques and evaluated for one or more of the functional activities of the native form of a polypeptide of the invention.

Preferred polypeptides have the amino acid sequence of SEQ ID NO:6, 7, 8, 9, 10, 19, 20, 21, 22 or 23. Other useful proteins are substantially identical (e.g., at least about 45%, preferably 55%, 65%, 75%, 85%, 95%, or 99%) to any of SEQ ID NO:6, 7, 8, 9, 10, 19, 20, 21, 22 or 23, and retain the functional activity of the protein of the corresponding naturally-occurring protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (, % identity=# of identical positions/total # of positions (e.g., overlapping positions)×100). In one embodiment, the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul, et al. (1990) *J. Mol. Biol.* 215:403-410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al. (1997) *Nucleic Acids Res.* 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. See http://www.ncbi.nlm.nih.gov.

Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the CGC sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti (1994) *Comput. Appl. Biosci.*, 10:3-5; and FASTA described in Pearson and Lipman (1988) *Proc. Natl. Acad. Sci.* 85:2444-8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA. For a further description of FASTA parameters, see http://bioweb.pasteur.fr/docs/man/man/fasta.1.html#sect2, the contents of which are incorporated herein by reference.

The percent identity between two sequences can be determined using techniques similar to those described above, with or without allowing gaps. In calculating percent identity, typically exact matches are counted.

The invention also provides chimeric or fusion proteins. As used herein, a "chimeric protein" or "fusion protein" comprises all or part (preferably biologically active) of a polypeptide of the invention operably linked to a heterologous polypeptide (i.e., a polypeptide other than the same polypeptide of the invention). Within the fusion protein, the term "operably linked" is intended to indicate that the polypeptide of the invention and the heterologous polypeptide are fused in-frame to each other. The heterologous polypeptide can be fused to the N-terminus or C-terminus of the polypeptide of the invention.

One useful fusion protein is a GST fusion protein in which the polypeptide of the invention is fused to the C-terminus of GST sequences. Such fusion proteins can facilitate the purification of a recombinant polypeptide of the invention.

In another embodiment, the fusion protein contains a heterologous signal sequence at its N-terminus. For example, the native signal sequence of a polypeptide of the invention can be removed and replaced with a signal sequence from another protein. For example, the gp67 secretory sequence of the baculovirus envelope protein can be used as a heterologous signal sequence (*Current Protocols in Molecular Biology*, Ausubel et al., eds., John Wiley & Sons, 1992). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Sambrook et al., supra) and the protein A secretory signal (Pharmacia Biotech; Piscataway, N.J.).

In yet another embodiment, the fusion protein is an immunoglobulin fusion protein in which all or part of a polypeptide of the invention is fused to sequences derived from a member of the immunoglobulin protein family. The immunoglobulin fusion proteins of the invention can be incorporated into pharmaceutical compositions and administered to a subject to inhibit an interaction between a ligand (soluble or membrane-bound) and a protein on the surface of a cell (receptor), to thereby suppress signal transduction in vivo. The immunoglobulin fusion protein can be used to affect the bioavailability of a cognate ligand of a polypeptide of the invention. Inhibition of ligand/receptor interaction may be useful therapeutically, both for treating proliferative and differentiative disorders and for modulating (e.g., promoting or inhibiting) cell survival. Moreover, the immunoglobulin fusion proteins of the invention can be used as immunogens to produce antibodies directed against a polypeptide of the invention in a subject, to purify ligands and in screening assays to identify molecules which inhibit the interaction of receptors with ligands.

Chimeric and fusion proteins of the invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide of the invention can be cloned into such an expression vector such that the fusion moiety is linked in-frame to the polypeptide of the invention.

A signal sequence of a polypeptide of the invention (SEQ ID NO:4 or 17) can be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the invention pertains to the described polypeptides having a signal sequence, as well as to the signal sequence itself and to the polypeptide in the absence of the signal sequence (i.e., the cleavage products). In one embodiment, a nucleic acid sequence encoding a signal sequence of the invention can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

In another embodiment, the signal sequences of the present invention can be used to identify regulatory sequences, e.g., promoters, enhancers, repressors. Since signal sequences are the most amino-terminal sequences of a peptide, it is expected that the nucleic acids which flank the signal sequence on its amino-terminal side will be regulatory sequences which affect transcription. Thus, a nucleotide sequence which encodes all or a portion of a signal sequence can be used as a probe to identify and isolate signal sequences and their flanking regions, and these flanking regions can be studied to identify regulatory elements therein.

The present invention also pertains to variants of the polypeptides of the invention. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a protein of the invention which function as either agonists (mimetics) or as antagonists can be identified by screening combinatorial libraries of mutants, e.g., truncation mutants, of the protein of the invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the polypeptides of the invention from a degenerate oligonucleotide sequence. Methods for synthesizing degenerate oligonucleotides are known in the art (see, e.g., Narang (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477).

In addition, libraries of fragments of the coding sequence of a polypeptide of the invention can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan (1992) *Proc. Natl. Acad. Sci. USA* 89:7811-7815; Delgrave et al. (1993) *Protein Engineering* 6(3):327-331).

The polypeptides of the invention can exhibit post-translational modifications, including, but not limited to glycosylations, (e.g., N-linked or O-linked glycosylations), myristylations, palmitylations, acetylations and phosphorylations (e.g., serine/threonine or tyrosine). In one embodiment, the TANGO 268 polypeptide of the invention exhibit reduced levels of O-linked glycosylation and/or N-linked glycosylation relative to endogenously expressed TANGO 268 polypeptides. In another embodiment, the TANGO 268 polypeptides of the invention do not exhibit O-linked glycosylation or N-linked glycosylation.

An isolated polypeptide of the invention, or a fragment thereof, can be used as an immunogen to generate antibodies using standard techniques for polyclonal and monoclonal antibody preparation. The full-length polypeptide or protein can be used or, alternatively, the invention provides antigenic peptide fragments for use as immunogens. The antigenic peptide of a protein of the invention comprises at least 8 (preferably 10, 15, 20, or 30) amino acid residues of the amino acid sequence of SEQ ID NO:3 or 16, and encompasses an epitope of the protein such that an antibody raised against the peptide forms a specific immune complex with the protein.

Epitopes encompassed by the antigenic peptide are regions that are located on the surface of the protein, e.g., hydrophilic regions. Alternatively, epitopes encompassed by the antigenic peptides are regions that are located within the proteins, and/or epitopes exposed in denatured or partially denatured forms of the polypeptides of the invention. FIGS. 2 and 7 are hydropathy plots of the proteins of the invention. These plots or similar analyses can be used to identify hydrophilic regions. In addition, an epitope can encompass, in addition to a polypeptide or polypeptides of the invention, a post-translational modification (e.g., glycosylation, such as, for example, N- and/or O-linked glycosylation of the polypeptide or polypeptides).

An immunogen typically is used to prepare antibodies by immunizing a suitable subject, (e.g., rabbit, goat, mouse or other mammal). An appropriate immunogenic preparation can contain, for example, recombinantly expressed or chemically synthesized polypeptide. The preparation can further include an adjuvant, such as Freund's complete or incomplete adjuvant, or similar immunostimulatory agent.

Accordingly, another aspect of the invention pertains to antibodies directed against a polypeptide of the invention. The term "antibody" as used herein refers to immunoglobulin molecules and immunologically active portions of immunoglobulin molecules, i.e., molecules that contain an antigen binding site which specifically binds an antigen, such as a polypeptide of the invention, e.g., an epitope of a polypeptide of the invention. A molecule which specifically binds to a given polypeptide of the invention is a molecule which binds the polypeptide, but does not substantially bind other molecules in a sample, e.g., a biological sample, which naturally contains the polypeptide. Examples of immunologically active portions of immunoglobulin molecules include F(ab) and F(ab')$_2$ fragments which can be generated by treating the antibody with an enzyme such as pepsin or papain. The invention provides polyclonal and monoclonal antibodies. The term "monoclonal antibody" or "monoclonal antibody composition", as used herein, refers to a population of antibody molecules that contain only one species of an antigen binding site capable of immunoreacting with a particular epitope.

Polyclonal antibodies can be prepared as described above by immunizing a suitable subject with a polypeptide of the invention as an immunogen. Preferred polyclonal antibody compositions are ones that have been selected for antibodies directed against a polypeptide or polypeptides of the invention. Particularly preferred polyclonal antibody preparations are ones that contain only antibodies directed against a polypeptide or polypeptides of the invention. Particularly preferred immunogen compositions are those that contain no other human proteins such as, for example, immunogen compositions made using a non-human host cell for recombinant expression of a polypeptide of the invention. In such a manner, the only human epitope or epitopes recognized by the resulting antibody compositions raised against this immunogen will be present as part of a polypeptide or polypeptides of the invention.

The antibody titer in the immunized subject can be monitored over time by standard techniques, such as with an enzyme linked immunosorbent assay (ELISA) using immobilized polypeptide. If desired, the antibody molecules can be isolated from the mammal (e.g., from the blood) and further purified by well-known techniques, such as protein A chromatography to obtain the IgG fraction. Alternatively, antibodies specific for a protein or polypeptide of the invention can be selected for (e.g., partially purified) or purified by, e.g., affinity chromatography. For example, a recombinantly expressed and purified (or partially purified) protein of the invention is produced as described herein, and covalently or non-covalently coupled to a solid support such as, for example, a chromatography column. The column can then be used to affinity purify antibodies specific for the proteins of the invention from a sample containing antibodies directed against a large number of different epitopes, thereby generating a substantially purified antibody composition, i.e., one that is substantially free of contaminating antibodies. By a substantially purified antibody composition is meant, in this context, that the antibody sample contains at most only 30% (by dry weight) of contaminating antibodies directed against epitopes other than those on the desired protein or polypeptide of the invention, and preferably at most 20%, yet more preferably at most 10%, and most preferably at most 5% (by dry weight) of the sample is contaminating antibodies. A purified antibody composition means that at least 99% of the antibodies in the composition are directed against the desired protein or polypeptide of the invention.

At an appropriate time after immunization, e.g., when the specific antibody titers are highest, antibody-producing cells can be obtained from the subject and used to prepare monoclonal antibodies by standard techniques, such as the hybridoma technique originally described by Kohler and Milstein (1975) *Nature* 256:495-497, the human B cell hybridoma technique (Kozbor et al. (1983) *Immunol. Today* 4:72), the EBV-hybridoma technique (Cole et al. (1985), *Monoclonal Antibodies and Cancer Therapy*, Alan R. Liss, Inc., pp. 77-96) or trioma techniques. The technology for producing hybridomas is well known (see generally *Current Protocols in Immunology* (1994) Coligan et al. (eds.) John Wiley & Sons, Inc., New York, N.Y.). Hybridoma cells producing a monoclonal antibody of the invention are detected by screening the hybridoma culture supernatants for antibodies that bind the polypeptide of interest, e.g., using a standard ELISA assay.

Alternative to preparing monoclonal antibody-secreting hybridomas, a monoclonal antibody directed against a polypeptide of the invention can be identified and isolated by screening a recombinant combinatorial immunoglobulin library (e.g., an antibody phage display library) with the polypeptide of interest. Kits for generating and screening phage display libraries are commercially available (e.g., the Pharmacia *Recombinant Phage Antibody System*, Catalog No. 27-9400-01; and the Stratagene *StufZAP™ Phage Display Kit*, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) *Bio/Technology* 9:1370-1372; Hay et al. (1992) *Hum. Antibod. Hybridomas* 3:81-85; Huse et al. (1989) *Science* 246:1275-1281; Griffiths et al. (1993) *EMBO J.* 12:725-734.

Additionally, recombinant antibodies, such as chimeric and humanized monoclonal antibodies, comprising both human and non-human portions, which can be made using standard recombinant DNA techniques, are within the scope of the invention. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816,397, which are incorporated herein by reference in their entirety.) Humanized antibodies are antibody molecules from non-human species having one or more complementarily determining regions (CDRs) from the non-human species and a framework region from a human immunoglobulin molecule. (See, e.g., Queen, U.S. Pat. No. 5,585,089, which is incorporated herein by reference in its entirety.) Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Canc. Res.* 47:999-1005; Wood et al. (1985) *Nature* 314:446-449; and Shaw et al. (1988) *J. Natl. Cancer Inst.* 80:1553-1559); Morrison (1985) *Science* 229:1202-1207; Oi et al. (1986) *Bio/Techniques* 4:214; U.S. Pat. No. 5,225,539; Jones et al. (1986) *Nature*

321:552-525; Verhoeyan et al. (1988) *Science* 239:1534; and Beidler et al. (1988) *J. Immunol.* 141:4053-4060.

Completely human antibodies are particularly desirable for therapeutic treatment of human patients. Such antibodies can be produced, for example, using transgenic mice which are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995, *Int. Rev. Immunol.* 13:65-93). For a detailed discussion of this technology for producing human antibodies and human monoclonal antibodies and protocols for producing such antibodies, see, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806. In addition, companies such as Abgenix, Inc. (Fremont, Calif.), can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al. (1994) *Bio/technology* 12:899-903).

An antibody directed against a polypeptide of the invention (e.g., monoclonal antibody) can be used to isolate the polypeptide by standard techniques, such as affinity chromatography or immunoprecipitation. Moreover, such an antibody can be used to detect the protein (e.g., in a cellular lysate or cell supernatant) in order to evaluate the abundance and pattern of expression of the polypeptide. The antibodies can also be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Further, an antibody (or fragment thereof) can be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincnstme, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, .alpha.-interferon, .beta.-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating a therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Alternatively, an antibody can be conjugated to a second antibody to form an antibody heteroconjugate as described by Segal in U.S. Pat. No. 4,676,980.

Accordingly, in one aspect, the invention provides substantially purified antibodies or fragment thereof, and non-human antibodies or fragments thereof, which antibodies or fragments specifically bind to a polypeptide comprising an amino acid sequence selected from the group consisting of: the amino acid sequence of SEQ ID NO:3 or 16, or the amino acid sequence encoded by the cDNA insert of the plasmid deposited with ATCC as Accession Number 207180, or the amino acid sequence encoded by the cDNA insert of the plasmid deposited with ATCC as PTA-225; a fragment of at least 15 amino acid residues of the amino acid sequence of SEQ ID NO:3 or 16; an amino acid sequence which is at least 95% identical to the amino acid sequence of SEQ ID NO:3 or 16, wherein the percent identity is determined using the ALIGN program of the GCG software package with a PAM120 weight residue table, a gap length penalty of 12, and a gap penalty of 4; and an amino acid sequence which is encoded by a nucleic acid molecule which hybridizes to the nucleic acid molecule consisting of SEQ ID NO:1, 2, 14, or 15 under conditions of hybridization of 6×SSC at 45° C. and washing in 0.2×SSC, 0.1% SDS at 65° C. In various embodiments, the substantially purified antibodies of the invention, or fragments thereof, can be human, non-human, chimeric and/or humanized antibodies.

In another aspect, the invention provides non-human antibodies or fragments thereof, which antibodies or fragments specifically bind to a polypeptide comprising an amino acid sequence selected from the group consisting of: the amino acid sequence of SEQ ID NO:3 or 16, or the amino acid sequence encoded by the cDNA insert of the plasmid deposited with ATCC as Accession Number 207180, or the amino acid sequence encoded by the cDNA insert of the plasmid deposited with ATCC as PTA-225; a fragment of at least 15 amino acid residues of the amino acid sequence of SEQ ID NO:3 or 16; an amino acid sequence which is at least 95% identical to the amino acid sequence of SEQ ID NO:3 or 16, wherein the percent identity is determined using the ALIGN program of the GCG software package with a PAM120 weight residue table, a gap length penalty of 12, and a gap penalty of 4; and an amino acid sequence which is encoded by a nucleic acid molecule which hybridizes to the nucleic acid molecule consisting of SEQ ID NO:1, 2, 14, or 15 under conditions of hybridization of 6×SSC at 45° C. and washing in 0.2×SSC, 0.1% SDS at 65° C. Such non-human antibodies can be goat, mouse, sheep, horse, chicken, rabbit, or rat antibodies. Alternatively, the non-human antibodies of the invention can be chimeric and/or humanized antibodies. In addition, the non-human antibodies of the invention can be polyclonal antibodies or monoclonal antibodies.

In still a further aspect, the invention provides monoclonal antibodies or fragments thereof, which antibodies or fragments specifically bind to a polypeptide comprising an amino acid sequence selected from the group consisting of: the amino acid sequence of SEQ ID NO:3 or 16, or the amino acid sequence encoded by the cDNA insert of the plasmid deposited with ATCC as Accession Number 207180, or the amino acid sequence encoded by the cDNA insert of the plasmid deposited with ATCC as PTA-225; a fragment of at least 15 amino acid residues of the amino acid sequence of SEQ ID NO:3 or 16; an amino acid sequence which is at least 95% identical to the amino acid sequence of SEQ ID NO:3 or 16, wherein the percent identity is determined using the ALIGN program of the GCG software package with a PAM120 weight residue table, a gap length penalty of 12, and a gap penalty of 4; and an amino acid sequence which is encoded by a nucleic acid molecule which hybridizes to the nucleic acid molecule consisting of SEQ ID NO:1, 2, 14, or 15 under conditions of hybridization of 6×SSC at 45° C. and washing in 0.2×SSC, 0.1% SDS at 65° C. The monoclonal antibodies can be human, humanized, chimeric and/or non-human antibodies.

In a particularly preferred embodiment, the substantially purified antibodies or fragments thereof, the non-human antibodies or fragments thereof, and/or the monoclonal antibodies or fragments thereof, of the invention specifically bind to an extracellular domain of the amino acid sequence of SEQ ID NO:3 or 16. Preferably, the extracellular domain to which the antibody, or fragment thereof, binds comprises amino acid residues 21 to 269 of SEQ ID NO:3 or amino acid residues 22 to 267 of SEQ ID NO:16. In an alternative embodiment, the extracellular domain to which the substantially purified antibody binds comprises an immunoglobulin-like domain. In one aspect, such an immunoglobulin-like domain comprises amino acid residues 48 to 88 or 134 to 180 of SEQ ID NO:3 or amino acid residues 49 to 89 or 135 to 181 of SEQ ID NO:16.

Any of the antibodies of the invention can be conjugated to a therapeutic moiety or to a detectable substance. Non-limiting examples of detectable substances that can be conjugated to the antibodies of the invention are an enzyme, a prosthetic group, a fluorescent material, a luminescent material, a bioluminescent material, and a radioactive material.

The invention also provides a kit containing an antibody of the invention conjugated to a detectable substance, and instructions for use. Still another aspect of the invention is a pharmaceutical composition comprising an antibody of the invention and a pharmaceutically acceptable carrier. In preferred embodiments, the pharmaceutical composition contains an antibody of the invention, a therapeutic moiety, and a pharmaceutically acceptable carrier.

Still another aspect of the invention is a method of making an antibody that specifically recognizes GPVI, the method comprising immunizing a mammal with a polypeptide. The polypeptide used as an immungen comprises an amino acid sequence selected from the group consisting of: the amino acid sequence of SEQ ID NO:3 or 16, or the amino acid sequence encoded by the cDNA insert of the plasmid deposited with ATCC as Accession Number 207180, or the amino acid sequence encoded by the cDNA insert of the plasmid deposited with ATCC as PTA-225; a fragment of at least 15 amino acid residues of the amino acid sequence of SEQ ID NO:3 or 16; an amino acid sequence which is at least 95% identical to the amino acid sequence of SEQ ID NO:3 or 16, wherein the percent identity is determined using the ALIGN program of the GCG software package with a PAM120 weight residue table, a gap length penalty of 12, and a gap penalty of 4; and an amino acid sequence which is encoded by a nucleic acid molecule which hybridizes to the nucleic acid molecule consisting of SEQ ID NO:1, 2, 14, or 15 under conditions of hybridization of 6×SSC at 45° C. and washing in 0.2×SSC, 0.1% SDS at 65° C. After immunization, a sample is collected from the mammal that contains an antibody that specifically recognizes GPVI. Preferably, the polypeptide is recombinantly produced using a non-human host cell. Optionally, the antibodies can be further purified from the sample using techniques well known to those of skill in the art. The method can further comprise producing a monoclonal antibody-producing cell from the cells of the mammal. Optionally, antibodies are collected from the antibody-producing cell.

In instances wherein the antibody is to be utilized as a therapeutic, characterization of the antibody can routinely be assayed and ascertained via the methods presented herein. For example, the fact that platelets are readily available, coupled with the availability of multiple assays for platelet function provide for routine testing and analysis (e.g., for in vitro testing and analysis) of such antibodies.

For example, the in vivo pharmacodynamic characterization of anti-TANGO 268 antibodies can be facilitated via the availability of various platelet assays (e.g., prolongation of bleeding time, quantitative measurement of TANGO 268 receptor blockade, inhibition of ex vivo platelet aggregation) such as those described herein that can be correlated with each other to permit more effective assessment of a modulator's functional consequences. The correlation available for such assays, therefore, allows for the in vitro characterization of an anti-TANGO 268 antibody to more directly apply to the measurement of the antibody's therapeutic effect.

In addition to utilizing the availability of platelets and platelet assays for assessing the therapeutic efficacy, including clinical efficacy, of an anti-TANGO 268 antibody, this availability can also be utilized for preclinical drug development aspects such as determining antibody dosage response, toxicology, magnitude of effect (e.g., magnitude of initial effect and magnitude of effect's duration), function, specificity (e.g., specificity with respect to particular platelet functions), receptor specificity, and species specificity (which, in turn, can identify appropriate animal models for pharmacology studies).

III. Recombinant Expression Vectors and Host Cells

Another aspect of the invention pertains to vectors, preferably expression vectors, containing a nucleic acid encoding a polypeptide of the invention (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

The recombinant expression vectors of the invention can be designed for expression of a polypeptide of the invention in prokaryotic (e.g., *E. coli*) or eukaryotic cells (e.g., insect cells (using baculovirus expression vectors), yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., (1988) *Gene* 69:301-315) and pET 11d (Studier et al., *Gene Expression Technology: Methods in Enzymology* 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident λ prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, *Gene Expression Technology: Methods in Enzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111-2118). Such alteration of nucleic acid sequences of the invention can be carried out by standard DNA synthesis techniques.

In another embodiment, the expression vector is a yeast expression vector. Examples of vectors for expression in yeast *S. cerivisae* include pYepSec1 (Baldari et al. (1987) *EMBO J.* 6:229-234), pMFa (Kurjan and Herskowitz, (1982) *Cell* 30:933-943), pJRY88 (Schultz et al. (1987) *Gene* 54:113-123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf 9 cells) include the pAc series (Smith et al. (1983) *Mol. Cell. Biol.* 3:2156-2165) and the pVL series (Lucklow and Summers (1989) *Virology* 170:31-39).

In yet another embodiment, a nucleic acid of the invention is expressed in mammalian cells using a mammalian expression vector. Examples of mammalian expression vectors include pCDM8 (Seed (1987) *Nature* 329:840) and pMT2PC (Kaufman et al. (1987) *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example the mouse hox promoters (Kessel and Gruss (1990) *Science* 249:374-379) and the beta-fetoprotein promoter (Camper and Tilghman (1989) *Genes Dev.* 3:537-546).

The invention further provides a recombinant expression vector comprising a DNA molecule of the invention cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (*Reviews—Trends in Genetics*, Vol. 1(1) 1986).

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

In another embodiment, the expression characteristics of an endogenous (e.g., TANGO 268 genes) within a cell, cell line or microorganism may be modified by inserting a DNA regulatory element heterologous to the endogenous gene of interest into the genome of a cell, stable cell line or cloned microorganism such that the inserted regulatory element is operatively linked with the endogenous gene (e.g., TANGO 268 genes) and controls, modulates or activates. For example, endogenous TANGO 268 genes which are normally "transcriptionally silent", i.e., a TANGO 268 genes which is normally not expressed, or are expressed only at very low levels in a cell line or microorganism, may be activated by inserting a regulatory element which is capable of promoting the expression of a normally expressed gene product in that cell line or microorganism. Alternatively, transcriptionally silent, endogenous TANGO 268 genes may be activated by insertion of a promiscuous regulatory element that works across cell types.

A heterologous regulatory element may be inserted into a stable cell line or cloned microorganism, such that it is operatively linked with and activates expression of endogenous TANGO 268 genes, using techniques, such as targeted homologous recombination, which are well known to those of skill in the art, and described e.g., in Chappel, U.S. Pat. No. 5,272,071; PCT publication No. WO 91/06667, published May 16, 1991.

A host cell of the invention, such as a prokaryotic or eukaryotic host cell in culture, can be used to produce a polypeptide of the invention. Accordingly, the invention further provides methods for producing a polypeptide of the invention using the host cells of the invention. In one embodiment, the method comprises culturing the host cell of invention (into which a recombinant expression vector encoding a polypeptide of the invention has been introduced) in a suitable medium such that the polypeptide is produced. In another embodiment, the method further comprises isolating the polypeptide from the medium or the host cell.

The host cells of the invention can also be used to produce nonhuman transgenic animals. For example, in one embodiment, a host cell of the invention is a fertilized oocyte or an embryonic stem cell into which a sequence encoding a polypeptide of the invention has been introduced. Such host cells can then be used to create non-human transgenic animals in which exogenous sequences encoding a polypeptide of the invention have been introduced into their genome or homologous recombinant animals in which endogenous encoding a polypeptide of the invention sequences have been altered. Such animals are useful for studying the function and/or activity of the polypeptide and for identifying and/or evaluating modulators of polypeptide activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

A transgenic animal of the invention can be created by introducing nucleic acid encoding a polypeptide of the invention (or a homologue thereof) into the male pronuclei of a fertilized oocyte, e.g., by microinjection, retroviral infection, and allowing the oocyte to develop in a pseudopregnant female foster animal. Intronic sequences and polyadenylation signals can also be included in the transgene to increase the efficiency of expression of the transgene. A tissue-specific regulatory sequence(s) can be operably linked to the transgene to direct expression of the polypeptide of the invention to particular cells. Methods for generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191 and in Hogan, *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of mRNA encoding the transgene in tissues or cells of the animals. A transgenic founder animal can then be used to breed additional animals carrying the transgene. Moreover, transgenic animals carrying the transgene can further be bred to other transgenic animals carrying other transgenes.

To create an homologous recombinant animal, a vector is prepared which contains at least a portion of a gene encoding a polypeptide of the invention into which a deletion, addition or substitution has been introduced to thereby alter, e.g., functionally disrupt, the gene. In a preferred embodiment, the vector is designed such that, upon homologous recombination, the endogenous gene is functionally disrupted (i.e., no longer encodes a functional protein; also referred to as a "knock out" vector). Alternatively, the vector can be designed such that, upon homologous recombination, the endogenous gene is mutated or otherwise altered but still encodes functional protein (e.g., the upstream regulatory region can be altered to thereby alter the expression of the endogenous protein). In the homologous recombination vector, the altered portion of the gene is flanked at its 5' and 3' ends by additional nucleic acid of the gene to allow for homologous recombination to occur between the exogenous gene carried by the vector and an endogenous gene in an embryonic stem cell. The additional flanking nucleic acid sequences are of sufficient length for successful homologous recombination with the endogenous gene. Typically, several kilobases of flanking DNA (both at the 5' and 3' ends) are included in the vector (see, e.g., Thomas and Capecchi (1987) *Cell* 51:503 for a description of homologous recombination vectors). The vector is introduced into an embryonic stem cell line (e.g., by electroporation) and cells in which the introduced gene has homologously recombined with the endogenous gene are selected (see, e.g., Li et al. (1992) *Cell* 69:915). The selected cells are then injected into a blastocyst of an animal (e.g., a mouse) to form aggregation chimeras (see, e.g., Bradley in *Teratocarcinomas and Embryonic Stem Cells: A Practical Approach*, Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823-829 and in PCT Publication Nos. WO 90/11354, WO 91/01140, WO 92/0968, and WO 93/04169.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232-6236. Another example of a recombinase system is the FLP recombinase system of *Saccharomyces cerevisiae* (O'Gorman et al. (1991) *Science* 251:1351-1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810-813 and PCT Publication NOS. WO 97/07668 and WO 97/07669.

IV. Pharmaceutical Compositions

The nucleic acid molecules, polypeptides, and antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes methods for preparing pharmaceutical compositions for modulating the expression or activity of a polypeptide or nucleic acid of the invention. Such methods comprise formulating a pharmaceutically acceptable carrier with an agent which modulates expression or activity of a polypeptide or nucleic acid of the invention. Such compositions can further include additional active agents. Thus, the invention further includes methods for preparing a pharmaceutical composition by formulating a pharmaceutically acceptable carrier with an agent which modulates expression or activity of a polypeptide or nucleic acid of the invention and one or more additional active compounds.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a polypeptide or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

For antibodies, the preferred dosage is 0.1 mg/kg to 100 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

Preferably, administration of the TANGO 268 modulator is at or near the site of the cells or tissue to be treated, e.g., administration is at or near the site of a platelet aggregation-induced disorder such as one of those described herein.

In certain embodiments, the TANGO 268 modulator is administered or co-administered with at least one other desirable agent, e.g., heparin or aspirin.

In certain instances, it is preferred that administration of a TANGO 268 modulator comprises an initial bolus followed by continuous infusion. For example, such instances will generally include those wherein the modulator exhibits appreciable reversibility in platelet binding, as, e.g., assayed via the techniques described herein.

In one example, presented by way of illustration and not by way of limitation, a dosage and administration regimen for treatment of ischemic heart disease or thromboses comprises: in patients undergoing percutaneous coronary angioplasty (PCA), the TANGO 268 modulator (e.g., anti-TANGO 268 antibody) is administered as a 0.25 mg/kg IV bolus plus infusion of 10 µg/min or 0.125 µg/kg/min (this can, alternatively, be performed in conjunction with heparin and aspirin) for 12 hours. In patients with refractory unstable angina in whom PCA is planned within 24 hours, the bolus and infusion are given 18-24 hours before the procedure and the infusion is continued for 1 hour or 12 hours after the procedure.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The nucleic acid molecules of the invention can be inserted into vectors and used as gene therapy vectors. Gene therapy vectors can be delivered to a subject by, for example, intravenous injection, local administration (U.S. Pat. No. 5,328, 470) or by stereotactic injection (see, e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) detection assays (e.g., chromosomal mapping, tissue typing, forensic biology); c) predictive medicine (e.g., diagnostic assays, prognostic assays, monitoring clinical trials, and pharmacogenomics); and d) methods of treatment (e.g., therapeutic and prophylactic). The isolated nucleic acid molecules of the invention can be used to express proteins (e.g., via a recombinant expression vector in a host cell in gene therapy applications), to detect mRNA (e.g., in a biological sample) or a genetic lesion, and to modulate activity of a polypeptide of the invention. In addition, the polypeptides of the invention can be used to screen drugs compounds which modulate activity or expression of a polypeptide of the invention as well as to treat disorders characterized by insufficient or excessive production of a protein of the invention or production of a form of a protein of the invention which has decreased or aberrant activity compared to the wild type protein. In addition, the antibodies of the invention can be used to detect and isolate a protein of the invention or to modulate activity of a protein of the invention.

This invention further pertains to novel agents identified by the above-described screening assays and uses thereof for treatments as described herein.

A. Screening Assays

The invention provides a method (also referred to herein as a "screening assay") for identifying modulators, i.e., candidate or test compounds or agents (e.g., peptides, peptidomimetics, small molecules or other drugs) which bind to polypeptide of the invention or have a stimulatory or inhibitory effect on, for example, expression or activity of a polypeptide of the invention.

In one embodiment, the invention provides assays for screening candidate or test compounds which bind to or modulate the activity of the membrane-bound form of a polypeptide of the invention or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Bio/Techniques* 13:412-421), or on beads (Lam (1991) *Nature* 354:82-84), chips (Fodor (1993) *Nature* 364:555-556), bacteria (U.S. Pat. No. 5,223,409), spores U.S. Pat. Nos. 5,571,698; 5,403,484; and 5,223,409), plasmids (Cull et al. (1992) *Proc. Natl. Acad. Sci. USA* 89:1865-1869) or phage (Scott and Smith (1990) *Science* 249:386-390; Devlin (1990) *Science* 249:404-406; Cwirla et al. (1990) *Proc. Natl. Acad. Sci. USA* 87:6378-6382; and Felici (1991) *J. Mol. Biol.* 222:301-310).

In one embodiment, an assay is a cell-based assay in which a cell which expresses a membrane-bound form of a polypeptide of the invention, or a biologically active portion thereof, on the cell surface is contacted with a test compound and the ability of the test compound to bind to the polypeptide determined. The cell, for example, can be a yeast cell or a cell of mammalian origin. Determining the ability of the test compound to bind to the polypeptide can be accomplished, for example, by coupling the test compound with a radioisotope or enzymatic label such that binding of the test compound to the polypeptide or biologically active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product. In a preferred embodiment, the assay comprises contacting a cell which expresses a membrane-bound form of a polypeptide of the invention, or a biologically active portion thereof, on the cell surface with a known compound which binds the polypeptide to form an assay mixture, contacting the assay mixture with a test compound, and determining the ability of the test compound to interact with the polypeptide, wherein determining the ability of the test compound to interact with the polypeptide comprises determining the ability of the test compound to preferentially bind to the polypeptide or a biologically active portion thereof as compared to the known compound.

In another embodiment, an assay is a cell-based assay comprising contacting a cell expressing a membrane-bound form of a polypeptide of the invention, or a biologically active portion thereof, on the cell surface with a test compound and determining the ability of the test compound to modulate (e.g., stimulate or inhibit) the activity of the polypeptide or biologically active portion thereof. Determining the ability of the test compound to modulate the activity of the polypeptide or a biologically active portion thereof can be accomplished, for example, by determining the ability of the polypeptide protein to bind to or interact with a target molecule.

Determining the ability of a polypeptide of the invention to bind to or interact with a target molecule can be accomplished by one of the methods described above for determining direct binding. As used herein, a "target molecule" is a molecule with which a selected polypeptide (e.g., a polypeptide of the invention) binds or interacts with in nature, for example, a molecule on the surface of a cell which expresses the selected protein, a molecule on the surface of a second cell, a molecule in the extracellular milieu, a molecule associated with the internal surface of a cell membrane or a cytoplasmic molecule. A target molecule can be a polypeptide of the invention or some other polypeptide or protein. For example, a target molecule can be a component of a signal transduction pathway which facilitates transduction of an extracellular signal (e.g., a signal generated by binding of a compound to a polypeptide of the invention) through the cell membrane and into the cell or a second intercellular protein which has catalytic activity or a protein which facilitates the association of downstream signaling molecules with a polypeptide of the invention. Determining the ability of a polypeptide of the invention to bind to or interact with a target molecule can be accomplished by determining the activity of the target molecule. For example, the activity of the target molecule can be determined by detecting induction of a cellular second messenger of the target (e.g., intracellular $Ca^{2+}$, diacylglycerol, IP3, etc.), detecting catalytic/enzymatic activity of the target on an appropriate substrate, detecting the induction of a reporter gene (e.g., a regulatory element that is responsive to a polypeptide of the invention operably linked to a nucleic acid encoding a detectable marker, e.g., luciferase), or detecting a cellular response, for example, cellular differentiation, or cell proliferation.

In yet another embodiment, an assay of the present invention is a cell-free assay comprising contacting a polypeptide of the invention or biologically active portion thereof with a test compound and determining the ability of the test compound to bind to the polypeptide or biologically active portion thereof. Binding of the test compound to the polypeptide can be determined either directly or indirectly as described above. In a preferred embodiment, the assay includes contacting the polypeptide of the invention or biologically active portion thereof with a known compound which binds the polypeptide to form an assay mixture, contacting the assay mixture with a test compound, and determining the ability of the test compound to interact with the polypeptide, wherein determining the ability of the test compound to interact with the polypeptide comprises determining the ability of the test compound to preferentially bind to the polypeptide or biologically active portion thereof as compared to the known compound.

In another embodiment, an assay is a cell-free assay comprising contacting a polypeptide of the invention or biologically active portion thereof with a test compound and determining the ability of the test compound to modulate (e.g., stimulate or inhibit) the activity of the polypeptide or biologically active portion thereof. Determining the ability of the test compound to modulate the activity of the polypeptide can be accomplished, for example, by determining the ability of the polypeptide to bind to a target molecule by one of the methods described above for determining direct binding. In an alternative embodiment, determining the ability of the test compound to modulate the activity of the polypeptide can be accomplished by determining the ability of the polypeptide of the invention to further modulate the target molecule. For example, the catalytic/enzymatic activity of the target molecule on an appropriate substrate can be determined as previously described.

In yet another embodiment, the cell-free assay comprises contacting a polypeptide of the invention or biologically active portion thereof with a known compound which binds the polypeptide to form an assay mixture, contacting the assay mixture with a test compound, and determining the ability of the test compound to interact with the polypeptide, wherein determining the ability of the test compound to interact with the polypeptide comprises determining the ability of the polypeptide to preferentially bind to or modulate the activity of a target molecule.

The cell-free assays of the present invention are amenable to use of both a soluble form or the membrane-bound form of a polypeptide of the invention. In the case of cell-free assays comprising the membrane-bound form of the polypeptide, it may be desirable to utilize a solubilizing agent such that the membrane-bound form of the polypeptide is maintained in solution. Examples of such solubilizing agents include non-ionic detergents such as n-octylglucoside, n-dodecylglucoside, n-octylmaltoside, octanoyl-N-methylglucamide, decanoyl-N-methylglucamide, Triton X-100, Triton X-114, Thesit, Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either the polypeptide of the invention or its target molecule to facilitate separation of complexed from uncomplexed forms of one or both of the proteins, as well as to accommodate automation of the assay. Binding of a test compound to the polypeptide, or interaction of the polypeptide with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase fusion proteins or glutathione-S-transferase fusion proteins can be adsorbed onto glutathione sepharose beads (Sigma Chemical; St. Louis, Mo.) or glutathione derivatized microtitre plates, which are then combined with the test compound or the test compound and either the non-adsorbed target protein or A polypeptide of the invention, and the mixture incubated under conditions conducive to complex formation (e.g., at physiological conditions for salt and pH). Following incubation, the beads or microtitre plate wells are washed to remove any unbound components and complex formation is measured either directly or indirectly, for example, as described above. Alternatively, the complexes can be dissociated from the matrix, and the level of binding or activity of the polypeptide of the invention can be determined using standard techniques.

Other techniques for immobilizing proteins on matrices can also be used in the screening assays of the invention. For example, either the polypeptide of the invention or its target molecule can be immobilized utilizing conjugation of biotin and streptavidin. Biotinylated polypeptide of the invention or target molecules can be prepared from biotin-NHS (N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with the polypeptide of the invention or target molecules but which do not interfere with binding of the polypeptide of the invention to its target molecule can be derivatized to the wells of the plate, and unbound target or polypeptide of the invention trapped in the wells by antibody conjugation. Methods for detecting such complexes, in addition to those described above for the GST-immobilized complexes, include immunodetection of complexes using antibodies reactive with the polypeptide of the invention or target molecule, as well as enzyme-linked assays which rely on detecting an enzymatic activity associated with the polypeptide of the invention or target molecule.

In another embodiment, modulators of expression of a polypeptide of the invention are identified in a method in which a cell is contacted with a candidate compound and the expression of the selected mRNA or protein (i.e., the mRNA or protein corresponding to a polypeptide or nucleic acid of the invention) in the cell is determined. The level of expression of the selected mRNA or protein in the presence of the candidate compound is compared to the level of expression of the selected mRNA or protein in the absence of the candidate compound. The candidate compound can then be identified as a modulator of expression of the polypeptide of the invention based on this comparison. For example, when expression of the selected mRNA or protein is greater (statistically significantly greater) in the presence of the candidate compound than in its absence, the candidate compound is identified as a stimulator of the selected mRNA or protein expression. Alternatively, when expression of the selected mRNA or protein is less (statistically significantly less) in the presence of the candidate compound than in its absence, the candidate compound is identified as an inhibitor of the selected mRNA or protein expression. The level of the selected mRNA or protein expression in the cells can be determined by methods described herein.

In yet another aspect of the invention, a polypeptide of the inventions can be used as "bait proteins" in a two-hybrid assay or three hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Bio/Tech-* niques 14:920-924; Iwabuchi et al. (1993) *Oncogene* 8:1693-1696; and PCT Publication No. WO 94/10300), to identify other proteins, which bind to or interact with the polypeptide of the invention and modulate activity of the polypeptide of the invention. Such binding proteins are also likely to be involved in the propagation of signals by the polypeptide of the inventions as, for example, upstream or downstream elements of a signaling pathway involving the polypeptide of the invention.

This invention further pertains to novel agents identified by the above-described screening assays and uses thereof for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. Accordingly, nucleic acid molecules described herein or fragments thereof, can be used to map the location of the corresponding genes on a chromosome. The mapping of the sequences to chromosomes is an important first step in correlating these sequences with genes associated with disease.

Briefly, genes can be mapped to chromosomes by preparing PCR primers (preferably 15-25 bp in length) from the sequence of a gene of the invention. Computer analysis of the sequence of a gene of the invention can be used to rapidly select primers that do not span more than one exon in the genomic DNA, thus complicating the amplification process. These primers can then be used for PCR screening of somatic cell hybrids containing individual human chromosomes. Only those hybrids containing the human gene corresponding to the gene sequences will yield an amplified fragment. For a review of this technique, see D'Eustachio et al. ((1983) *Science* 220:919-924).

PCR mapping of somatic cell hybrids is a rapid procedure for assigning a particular sequence to a particular chromosome. Three or more sequences can be assigned per day using a single thermal cycler. Using the nucleic acid sequences of the invention to design oligonucleotide primers, sublocalization can be achieved with panels of fragments from specific chromosomes. Other mapping strategies which can similarly be used to map a gene to its chromosome include in situ hybridization (described in Fan et al. (1990) *Proc. Natl. Acad. Sci. USA* 87:6223-27), pre-screening with labeled flow-sorted chromosomes (CITE), and pre-selection by hybridization to chromosome specific cDNA libraries. Fluorescence in situ hybridization (FISH) of a DNA sequence to a metaphase chromosomal spread can further be used to provide a precise chromosomal location in one step. For a review of this technique, see Verma et al., (Human Chromosomes: A Manual of Basic Techniques (Pergamon Press, New York, 1988)).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between genes and disease, mapped to the same chromosomal region, can then be identified through linkage analysis (co-inheritance of physically adjacent genes), described in, e.g., Egeland et al. (1987) *Nature* 325:783-787.

Moreover, differences in the DNA sequences between individuals affected and unaffected with a disease associated with a gene of the invention can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

In the instant case, the human gene for GPVI was mapped on radiation hybrid panels to the long arm of chromosome 19, in the region 19q13. This region is syntenic to mouse chromosome 7. Multiple members of the immunoglobulin superfamily, including killer cell inhibitory receptors, immunoglobulin-like transcripts (ILT1, 2, 3), the gp49b family and the Fc_receptor (CD89) also map to this region of the human chromosome. These various receptors differ considerably with respect to function and expression and it may be hypothesized that functional differentiation occurred after duplication of a common ancestral gene.

The mouse gene for GPVI was mapped using the T31 Mouse/Hamster Radiation Hybrid (McCarthy, Terrett et al. 1997). PCR Amplification used the following mouse primers: forward primer 5'-CTGTAGCTGTTTTCAGACACACC-3' (SEQ ID NO:31) and reverse primer 5'-CCATCAC-CTCTTTCTGGTTAC-3' (SEQ ID NO:32). All PCRs were performed with an annealing temperature of 52_C and extension times of 50 s (72_C) and for 35 cycles, with a final extension of 5 minutes on an MJ Research Peltier PCT-225 Thermal Cycler.

2. Tissue Typing

The nucleic acid sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the nucleic acid sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The nucleic acid sequences of the invention uniquely represent portions of the human genome. Allelic variation occurs to some degree in the coding regions of these sequences, and to a greater degree in the noncoding regions. It is estimated that allelic variation between individual humans occurs with a frequency at about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 or 14 can comfortably provide positive individual identification with a panel of perhaps 10 to 1,000 primers which each yield a noncoding amplified sequence of 100 bases. If predicted coding sequences, such as those in SEQ ID NO:1 or 14 are used, a more appropriate number of primers for positive individual identification would be 500-2,000.

If a panel of reagents from the nucleic acid sequences described herein is used to generate a unique identification database for an individual, those same reagents can later be used to identify tissue from that individual. Using the unique identification database, positive identification of the individual, living or dead, can be made from extremely small tissue samples.

3. Use of Partial Gene Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions are particularly appropriate for this use as greater numbers of polymorphisms occur in the noncoding regions, making it easier to differentiate individuals using this technique. Examples of polynucleotide reagents include the nucleic acid sequences of the invention or portions thereof, e.g., fragments derived from noncoding regions having a length of at least 20 or 30 bases.

The nucleic acid sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such probes can be used to identify tissue by species and/or by organ type.

C. Predictive Medicine

The present invention also pertains to the field of predictive medicine in which diagnostic assays, prognostic assays, pharmacogenomics, and monitoring clinical trails are used for prognostic (predictive) purposes to thereby treat an individual prophylactically. Accordingly, one aspect of the present invention relates to diagnostic assays for determining expression of a polypeptide or nucleic acid of the invention and/or activity of a polypeptide of the invention, in the context of a biological sample (e.g., blood, serum, cells, tissue) to thereby determine whether an individual is afflicted with a disease or disorder, or is at risk of developing a disorder, associated with aberrant expression or activity of a polypeptide of the invention. The invention also provides for prognostic (or predictive) assays for determining whether an individual is at risk of developing a disorder associated with aberrant expression or activity of a polypeptide of the invention. For example, mutations in a gene of the invention can be assayed in a biological sample. Such assays can be used for prognostic or predictive purpose to thereby prophylactically treat an individual prior to the onset of a disorder characterized by or associated with aberrant expression or activity of a polypeptide of the invention.

Another aspect of the invention provides methods for expression of a nucleic acid or polypeptide of the invention or activity of a polypeptide of the invention in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent).

Yet another aspect of the invention pertains to monitoring the influence of agents (e.g., drugs or other compounds) on the expression or activity of a polypeptide of the invention in clinical trials. These and other agents are described in further detail in the following sections.

1. Diagnostic Assays

An exemplary method for detecting the presence or absence of a polypeptide or nucleic acid of the invention in a biological sample involves obtaining a biological sample from a test subject and contacting the biological sample with a compound or an agent capable of detecting a polypeptide or nucleic acid (e.g., mRNA, genomic DNA) of the invention such that the presence of a polypeptide or nucleic acid of the invention is detected in the biological sample. A preferred agent for detecting mRNA or genomic DNA encoding a polypeptide of the invention is a labeled nucleic acid probe capable of hybridizing to mRNA or genomic DNA encoding a polypeptide of the invention. The nucleic acid probe can be, for example, a full-length cDNA, such as the nucleic acid of SEQ ID NO:1, 2, 14 or 15, or a portion thereof, such as an oligonucleotide of at least 15, 30, 50, 100, 250 or 500 nucleotides in length and sufficient to specifically hybridize under stringent conditions to a mRNA or genomic DNA encoding a polypeptide of the invention. Other suitable probes for use in the diagnostic assays of the invention are described herein.

A preferred agent for detecting a polypeptide of the invention is an antibody capable of binding to a polypeptide of the invention, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect mRNA, protein, or genomic DNA in a biological sample in vitro as well as in vivo. For example, in vitro techniques for detection of mRNA include Northern hybridizations and in situ hybridizations. In vitro techniques for detection of a polypeptide of the invention include enzyme linked immunosorbent assays (ELISAs), Western blots, immunoprecipitations and immunofluorescence. In vitro techniques for detection of genomic DNA include Southern hybridizations. Furthermore, in vivo techniques for detection of a polypeptide of the invention include introducing into a subject a labeled antibody directed against the polypeptide. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

In another embodiment, the methods further involve obtaining a control biological sample from a control subject, contacting the control sample with a compound or agent capable of detecting a polypeptide of the invention or mRNA or genomic DNA encoding a polypeptide of the invention, such that the presence of the polypeptide or mRNA or genomic DNA encoding the polypeptide is detected in the biological sample, and comparing the presence of the polypeptide or mRNA or genomic DNA encoding the polypeptide in the control sample with the presence of the polypeptide or mRNA or genomic DNA encoding the polypeptide in the test sample.

The invention also encompasses kits for detecting the presence of a polypeptide or nucleic acid of the invention in a biological sample (a test sample). Such kits can be used to determine if a subject is suffering from or is at increased risk of developing a disorder associated with aberrant expression of a polypeptide of the invention as discussed, for example, n sections above relating to uses of the sequences of the invention.

For example, kits can be used to determine if a subject is suffering from or is at increased risk of disorders such as immunological disorders, (e.g. thrombocytopenia and platelet disorders), liver disorders, cerebral vascular diseases (e.g., stroke and ischemia), venous thromboembolisme diseases (e.g., diseases involving leg swelling, pain and ulceration, pulmonary embolism, abdominal venous thrombosis), coronary diseases (e.g., cardiovascular diseases including unstable angina, acute myocardial infarction, coronary artery disease, coronary revascularization, ventricular thromboembolism, atherosclerosis, coronary artery disease, and plaque formation), metastatic cancers (e.g., the metastasis of cancerous colon and liver cells) and embryonic disorders, which are associated with aberrant TANGO 268 expression. The kit, for example, can comprise a labeled compound or agent capable of detecting the polypeptide or mRNA encoding the polypeptide in a biological sample and means for determining the amount of the polypeptide or mRNA in the sample (e.g., an antibody which binds the polypeptide or an oligonucleotide probe which binds to DNA or mRNA encoding the polypeptide). Kits can also include instructions for observing that the tested subject is suffering from or is at risk of developing a disorder associated with aberrant expression of the polypeptide if the amount of the polypeptide or mRNA encoding the polypeptide is above or below a normal level.

For antibody-based kits, the kit can comprise, for example: (1) a first antibody (e.g., attached to a solid support) which binds to a polypeptide of the invention; and, optionally, (2) a second, different antibody which binds to either the polypeptide or the first antibody and is conjugated to a detectable agent.

For oligonucleotide-based kits, the kit can comprise, for example: (1) an oligonucleotide, e.g., a detectably labeled oligonucleotide, which hybridizes to a nucleic acid sequence encoding a polypeptide of the invention or (2) a pair of primers useful for amplifying a nucleic acid molecule encoding a polypeptide of the invention. The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples which can be assayed and compared to the test sample contained. Each component of the kit is usually enclosed within an individual container and all of the various containers are within a single package along with instructions for observing whether the tested subject is suffering from or is at risk of developing a disorder associated with aberrant expression of the polypeptide.

2. Prognostic Assays

The methods described herein can furthermore be utilized as diagnostic or prognostic assays to identify subjects having or at risk of developing a disease or disorder associated with aberrant expression or activity of a polypeptide of the invention. For example, the assays described herein, such as the preceding diagnostic assays or the following assays, can be utilized to identify a subject having or at risk of developing a disorder associated with aberrant expression or activity of a polypeptide of the invention, e.g., an immunologic disorder, or embryonic disorders. Alternatively, the prognostic assays can be utilized to identify a subject having or at risk for developing such a disease or disorder. Thus, the present invention provides a method in which a test sample is obtained from a subject and a polypeptide or nucleic acid (e.g., mRNA, genomic DNA) of the invention is detected, wherein the presence of the polypeptide or nucleic acid is diagnostic for a subject having or at risk of developing a disease or disorder associated with aberrant expression or activity of the polypeptide. As used herein, a "test sample" refers to a biological sample obtained from a subject of interest. For example, a test sample can be a biological fluid (e.g., serum), cell sample, or tissue.

The prognostic assays described herein, for example, can be used to identify a subject having or at risk of developing disorders such as disorders discussed, for example, in sections above relating to uses of the sequences of the invention. For example, such disorders can include immunological disorders, (e.g. thrombocytopenia and platelet disorders), liver disorders, cerebral vascular diseases (e.g., stroke and ischemia), venous thromboembolisme diseases (e.g., diseases involving leg swelling, pain and ulceration, pulmonary embolism, abdominal venous thrombosis), coronary diseases (e.g., cardiovascular diseases including unstable angina, acute myocardial infarction, coronary artery disease, coronary revascularization, ventricular thromboembolism, atherosclerosis, coronary artery disease, and plaque formation), metastatic cancers (e.g., the metastasis of cancerous colon and liver cells) and progression to such metastatic tumors, developmental disorders and embryonic disorders, which are associated with aberrant TANGO 268 expression.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant expression or activity of a polypeptide of the invention. For example, such methods can be used to determine whether a subject can be effectively treated with a specific agent or class of agents (e.g., agents of a type which decrease activity of the polypeptide). Thus, the present invention provides methods for determining whether a subject can be effectively treated with an agent for a disorder associated with aberrant expression or activity of a polypeptide of the invention in which a test sample is obtained and the polypeptide or nucleic acid encoding the polypeptide is detected (e.g., wherein the presence of the polypeptide or nucleic acid is diagnostic for a subject that can be administered the agent to treat a disorder associated with aberrant expression or activity of the polypeptide).

The methods of the invention can also be used to detect genetic lesions or mutations in a gene of the invention, thereby determining if a subject with the lesioned gene is at risk for a disorder characterized aberrant expression or activity of a polypeptide of the invention. In preferred embodiments, the methods include detecting, in a sample of cells from the subject, the presence or absence of a genetic lesion or mutation characterized by at least one of an alteration affecting the integrity of a gene encoding the polypeptide of the invention, or the mis-expression of the gene encoding the polypeptide of the invention. For example, such genetic lesions or mutations can be detected by ascertaining the existence of at least one of: 1) a deletion of one or more nucleotides from the gene; 2) an addition of one or more nucleotides to the gene; 3) a substitution of one or more nucleotides of the gene; 4) a chromosomal rearrangement of the gene; 5) an alteration in the level of a messenger RNA transcript of the gene; 6) an aberrant modification of the gene, such as of the methylation pattern of the genomic DNA; 7) the presence of a non-wild type splicing pattern of a messenger RNA transcript of the gene; 8) a non-wild type level of a the protein encoded by the gene; 9) an allelic loss of the gene; and 10) an inappropriate post-translational modification of the protein encoded by the gene. As described herein, there are a large number of assay techniques known in the art which can be used for detecting lesions in a gene.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077-1080; and Nakazawa et al. (1994) *Proc. Natl. Acad. Sci. USA* 91:360-364), the latter of which can be particularly useful for detecting point mutations in a gene (see, e.g., Abravaya et al. (1995) *Nucleic Acids Res.* 23:675-682). This method can include the steps of collecting a sample of cells from a patient, isolating nucleic acid (e.g., genomic, mRNA or both) from the cells of the sample, contacting the nucleic acid sample with one or more primers which specifically hybridize to the selected gene under conditions such that hybridization and amplification of the gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) *Proc. Natl. Acad. Sci. USA* 87:1874-1878), transcriptional amplification system (Kwoh, et al. (1989) *Proc. Natl. Acad. Sci. USA* 86:1173-1177), Q-Beta Replicase (Lizardi et al. (1988) *Bio/Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a selected gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations can be identified by hybridizing a sample and control nucleic acids, e.g., DNA or RNA, to high density arrays containing hundreds or thousands of oligonucleotides probes (Cronin et al. (1996) *Human Mutation* 7:244-255; Kozal et al. (1996) *Nature Medicine* 2:753-759). For example, genetic mutations can be identified in two-dimensional arrays containing light-generated DNA probes as described in Cronin et al., supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the selected gene and detect mutations by comparing the sequence of the sample nucleic acids with the corresponding wild-type (control) sequence. Examples of sequencing reactions include those based on techniques developed by Maxim and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Bio/Techniques* 19:448), including sequencing by mass spectrometry (see, e.g., PCT Publication No. WO 94/16101; Cohen et al. (1996) *Adv. Chromatogr.* 36:127-162; and Griffin et al. (1993) *Appl. Biochem. Biotechnol.* 38:147-159).

Other methods for detecting mutations in a selected gene include methods in which protection from cleavage agents is used to detect mismatched bases in RNA/RNA or RNA/DNA heteroduplexes (Myers et al. (1985) *Science* 230:1242). In general, the technique of "mismatch cleavage" entails providing heteroduplexes formed by hybridizing (labeled) RNA or DNA containing the wild-type sequence with potentially mutant RNA or DNA obtained from a tissue sample. The double-stranded duplexes are treated with an agent which cleaves single-stranded regions of the duplex such as which will exist due to basepair mismatches between the control and sample strands. RNA/DNA duplexes can be treated with RNase to digest mismatched regions, and DNA/DNA hybrids can be treated with S1 nuclease to digest mismatched regions.

In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton et al. (1988) *Proc. Natl. Acad. Sci. USA* 85:4397; Saleeba et al. (1992) *Methods Enzymol.* 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662). According to an exemplary embodiment, a probe based on a selected sequence, e.g., a wild-type sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in genes. For example, single strand conformation polymorphism (SSCP) may be used to detect differences in electrophoretic mobility between mutant and wild type nucleic acids (Orita et al. (1989) *Proc. Natl. Acad. Sci. USA* 86:2766; see also Cotton (1993) *Mutat. Res.* 285:125-144; Hayashi (1992) *Genet. Anal. Tech. Appl.* 9:73-79). Single-stranded DNA fragments of sample and control nucleic acids will be denatured and allowed to renature. The secondary structure of single-stranded nucleic acids varies according to sequence, and the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet.* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313: 495). When DGGE is used as the method of analysis, DNA will be modified to insure that it does not completely denature, for example by adding a 'GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl. Acad. Sci. USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent or reduce polymerase extension (Prossner (1993) *Tibtech* 11:238). In addition, it may be desirable to introduce a novel restriction site in the region of the mutation to create cleavage-based detection (Gasparini et al. (1992) *Mol. Cell. Probes* 6:1). It is anticipated that in certain embodiments amplification may also be performed using Taq ligase for amplification (Barany (1991) *Proc. Natl. Acad. Sci. USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a gene encoding a polypeptide of the invention. Furthermore, any cell type or tissue, e.g., chondrocytes, in which the polypeptide of the invention is expressed may be utilized in the prognostic assays described herein.

3. Pharmacogenomics

Agents, or modulators which have a stimulatory or inhibitory effect on activity or expression of a polypeptide of the invention as identified by a screening assay described herein can be administered to individuals to treat (prophylactically or therapeutically) disorders associated with aberrant activity of the polypeptide. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of a polypeptide of the invention, expression of a nucleic acid of the invention, or mutation content of a gene of the invention in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) Clin. Chem. 43(2):254-266. In general, two types of pharmacogenetic conditions can be differentiated. Genetic conditions transmitted as a single factor altering the way drugs act on the body are referred to as "altered drug action." Genetic conditions transmitted as single factors altering the way the body acts on drugs are referred to as "altered drug metabolism". These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, a PM will show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of a polypeptide of the invention, expression of a nucleic acid encoding the polypeptide, or mutation content of a gene encoding the polypeptide in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a modulator of activity or expression of the polypeptide, such as a modulator identified by one of the exemplary screening assays described herein.

4. Monitoring of TANGO 268 Modulator Effects

Monitoring the influence of agents (e.g., drugs, compounds) on the expression or activity of a polypeptide of the invention (e.g., the ability to modulate aberrant cell proliferation chemotaxis, and/or differentiation) can be applied in basic drug screening, preclinical studies, clinical trials and during therapeutic treatment regimens.

For example, the effectiveness of an agent, as determined by a screening assay as described herein, to increase gene expression, protein levels or protein activity, can be monitored in clinical trials of subjects exhibiting decreased gene expression, protein levels, or protein activity. Alternatively, the effectiveness of an agent, as determined by a screening assay, to decrease gene expression, protein levels or protein activity, can be monitored in clinical trials of subjects exhibiting increased gene expression, protein levels, or protein activity. In such clinical trials, expression or activity of a polypeptide of the invention and preferably, that of other polypeptide that have been implicated in for example, a cellular proliferation disorder, can be used as a marker of the immune responsiveness of a particular cell.

For example, and not by way of limitation, genes, including those of the invention, that are modulated in cells by treatment with an agent (e.g., compound, drug or small molecule) which modulates activity or expression of a polypeptide of the invention (e.g., as identified in a screening assay described herein) can be identified. Thus, to study the effect of agents on cellular proliferation disorders, for example, in a clinical trial, cells can be isolated and RNA prepared and analyzed for the levels of expression of a gene of the invention and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of a gene of the invention or other genes. In this way, the gene expression pattern can serve as a marker, indicative of the physiological response of the cells to the agent. Accordingly, this response state may be determined before, and at various points during, treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of the polypeptide or nucleic acid of the invention in the preadministration sample; (iii) obtaining one or more post-administration samples from the subject; (iv) detecting the level the of the polypeptide or nucleic acid of the invention in the post-administration samples; (v) comparing the level of the polypeptide or nucleic acid of the invention in the pre-administration sample with the level of the polypeptide or nucleic acid of the invention in the post-administration sample or samples; and (vi) altering the administration of the agent to the subject accordingly. For example, increased administration of the agent may be desirable to increase the expression or activity of the polypeptide to higher levels than detected, i.e., to increase the effectiveness of the agent. Alternatively, decreased administration of the agent may be desirable to decrease expression or activity of the polypeptide to lower levels than detected, i.e., to decrease the effectiveness of the agent.

TANGO 268 is expressed on the surface of platelets. As such, a cellular and therapeutic target of modulators of TANGO 268 (e.g., an anti-TANGO 268 antibody) is readily available for testing and analysis (e.g., for in vitro testing and analysis). This coupled with the availability of several different relevant platelet assays (see above) provides an unusual drug development opportunity for TANGO 268 modulators. For example, the in vivo pharmacodynamic characterization of TANGO 268 modulators can be facilitated via the availability of various platelet assays (e.g., prolongation of bleeding time, quantitative measurement of TANGO 268 receptor blockade, inhibition of ex vivo platelet aggregation) that can be correlated with each other to permit more effective assessment of a modulator's functional consequences. The correlation available for such assays, therefore, allows for the in vitro characterization of a TANGO 268 modulator to more directly apply to the measurement of the modulator's therapeutic effect.

In addition to utilizing the availability of platelets and platelet assays for assessing the therapeutic efficacy, including clinical efficacy, of a TANGO 268 modulator, this availability can also be utilized for preclinical drug development aspects such as determining modulator dosage response, toxicology, magnitude of effect (e.g., magnitude of initial effect and magnitude of effect's duration), function, specificity (e.g., specificity with respect to particular platelet functions), receptor specificity, and species specificity (which, in turn, can identify appropriate animal models for pharmacology studies).

In one embodiment, therefore, a method of the invention includes a method for identifying a TANGO 268 modulator, (e.g., an anti-TANGO 268 antibody), comprising: incubating a platelet (preferably human platelet)-rich sample with a compound and a platelet agonist (e.g., ADP, epinephrine, thrombin, collagen), and assaying platelet aggregation, such that if platelet aggregation in the sample differs from that of a corresponding platelet-rich sample incubated with the platelet agonist in the absence of the compound, then a modulator of TANGO 268 platelet aggregation is identified. In a variation of this embodiment, the sample is incubated with the compound prior to addition and concurrent incubation with the platelet agonist.

In another embodiment, a method of the invention includes a method for monitoring the clinical efficacy of a TANGO 268 modulator (or the effectiveness of treatment with a TANGO 268 modulator), comprising: incubating a patient sample comprising platelets (a platelet-rich sample, e.g., one containing approximately 200,000–/300,000 platelets per $ml^3$) with a platelet agonist, measuring the level of platelet aggregation in the sample, and comparing the level obtained with that of a corresponding control platelet sample, wherein the patient sample is obtained from a patient to whom a TANGO 268 modulator has been administered, and the control platelet sample is one that has been incubated with the platelet agonist but has not been treated with the TANGO 268 modulator. In instances wherein the aggregation level obtained in the patient sample is lower than that of the control sample, the monitoring of the clinical efficacy of the TANGO 268 modulator (or the effectiveness of treatment with the TANGO 268 modulator) is confirmed.

In yet another embodiment, a method of the invention includes a method for determining the therapeutic dosage of a TANGO 268 modulator to be administered to an individual in need of treatment for a TANGO 268-related disorder, comprising: administering a dose of a TANGO 268 modulator to a non-human animal model of a TANGO 268-related disorder, and assaying TANGO 268 function and/or assaying a symptom of the TANGO 268-related disorder in the animal, so that if TANGO 268 function and/or symptom in the animal is modulated in a manner that more closely resembles a corresponding animal not exhibiting the TANGO 268 disorder, a therapeutic dosage of the TANGO 268 modulator is determined, e.g., by extrapolating to the corresponding dosage in a human.

In a particular embodiment of such a method, platelet function and/or aggregation is assayed via, e.g., techniques such as those presented herein. Further, the animal model can be, e.g., one of the animal models described herein.

C. Methods of Treatment

The present invention provides for both prophylactic and therapeutic methods of treating a subject at risk of (or susceptible to) a disorder or having a disorder associated with aberrant expression or activity of a polypeptide of the invention, as discussed, for example, in sections above relating to uses of the sequences of the invention. For example, disorders characterized by aberrant expression or activity of the polypeptides of the invention include immunologic disorders, developmental disorders, embryonic disorders, liver disorders, cerebral vascular diseases (e.g., stroke and ischemia), venous thromboembolisme diseases (e.g., diseases involving leg swelling, pain and ulceration, pulmonary embolism, abdominal venous thrombosis), coronary diseases (e.g., cardiovascular diseases including unstable angina, acute myocardial infarction, coronary artery disease, coronary revascularization, ventricular thromboembolism, atherosclerosis, coronary artery disease, and plaque formation), and metastatic cancers (e.g., the metastasis of cancerous colon and liver cells). The nucleic acids, polypeptides, and modulators thereof of the invention can be used to treat immunologic diseases and disorders (e.g., platelet disorders), embryonic disorders liver disorders, cerebral vascular diseases (e.g., stroke and ischemia), venous thromboembolisme diseases (e.g., diseases involving leg swelling, pain and ulceration, pulmonary embolism, abdominal venous thrombosis), thrombotic disorders (e.g., thrombotic occlusion of coronary arteries), coronary diseases (e.g., cardiovascular diseases, including unstable angina pectoris, myocardial infarction, acute myocardial infarction, coronary artery disease, coronary revascularization, coronary restenosis, ventricular thromboembolism, atherosclerosis, coronary artery disease (e.g., arterial occulsive disorders), and plaque formation, cardiac ischemia, including complications related to coronary procedures, such as percutaneous coronary artery angioplasty (balloon angioplasty) procedures). With respect to coronary procedures, such modulation can be achieved via administration of GPVI modulators prior to, during, or subsequent to the procedure. In a preferred embodiment, such administration can be utilized to prevent acture cardiac ischemia following angioplasty and metastatic cancers (e.g., the metastasis of cancerous colon and liver cells), as well as other disorders described herein.

TANGO 268 nucleic acids, proteins and modulators thereof can, therefore, be used to modulate disorders resulting from any blood vessel insult that can result in platelet aggregation. Such blood vessel insults include, but are not limited to, vessel wall injury, such as vessel injuries that result in a highly thrombogenic surface exposed within an otherwise intact blood vessel e.g., vessel wall injuries that result in release of ADP, thrombin and/or epinephrine, fluid shear stress that occurs at the site of vessel narrowing, ruptures and/or tears at the sites of atherosclerotic plaques, and injury resulting from balloon angioplasty or atherectomy.

Preferably, the TANGO 268 nucleic acids, proteins and modulators (e.g., anti-TANGO 268 antibodies) thereof do not effect initial platelet adhesion to vessel surfaces, or effect such adhesion to a relatively lesser extent than the effect on platelet-platelet aggregation, e.g., unregulated platelet-platelet aggregation, following the initial platelet adhesion. Further, in certain embodiments, it is preferred that the TANGO 268 nucleic acids, proteins and modulators (e.g., anti-TANGO 268 antibodies) thereof do not effect other platelet attributes or functions, such as agonist-induced platelet shape change (e.g., GPIb-vWF-mediated platelet agglutination induced by ristocetin), release of internal platelet granule components, activation of signal transduction pathways or induction of calcium mobilization upon platelet activation.

1. Prophylactic Methods

In one aspect, the invention provides a method for preventing in a subject, a disease or condition associated with an aberrant expression or activity of a polypeptide of the invention, by administering to the subject an agent which modulates expression or at least one activity of the polypeptide. Subjects at risk for a disease which is caused or contributed to by aberrant expression or activity of a polypeptide of the invention can be identified by, for example, any or a combination of diagnostic or prognostic assays as described herein. Administration of a prophylactic agent can occur prior to the manifestation of symptoms characteristic of the aberrancy, such that a disease or disorder is prevented or, alternatively, delayed in its progression. Depending on the type of aberrancy, for example, an agonist or antagonist agent can be used for treating the subject. For example, an antagonist of a TANGO 240 protein may be used to treat an arthropathic disorder, e.g., rheumatoid arthritis. The appropriate agent can be determined based on screening assays described herein.

2. Therapeutic Methods

Another aspect of the invention pertains to methods of modulating expression or activity of a polypeptide of the invention for therapeutic purposes. The modulatory method of the invention involves contacting a cell with an agent that modulates one or more of the activities of the polypeptide. An agent that modulates activity can be an agent as described herein, such as a nucleic acid or a protein, a naturally-occurring cognate ligand of the polypeptide, a peptide, a peptidomimetic, or other small molecule. In one embodiment, the agent stimulates one or more of the biological activities of the polypeptide. Examples of such stimulatory agents include the active polypeptide of the invention and a nucleic acid molecule encoding the polypeptide of the invention that has been introduced into the cell. In another embodiment, the agent inhibits one or more of the biological activities of the polypeptide of the invention. Examples of such inhibitory agents include antisense nucleic acid molecules and antibodies. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a polypeptide of the invention. In one embodiment, the method involves administering an agent (e.g., an agent identified by a screening assay described herein), or combination of agents that modulates (e.g., upregulates or downregulates) expression or activity. In another embodiment, the method involves administering a polypeptide of the invention or a nucleic acid molecule of the invention as therapy to compensate for reduced or aberrant expression or activity of the polypeptide.

Stimulation of activity is desirable in situations in which activity or expression is abnormally low or downregulated and/or in which increased activity is likely to have a beneficial effect. Conversely, inhibition of activity is desirable in situations in which activity or expression is abnormally high or upregulated and/or in which decreased activity is likely to have a beneficial effect.

The contents of all references, patents and published patent applications cited throughout this application are hereby incorporated by reference.

Deposit of Clones

A clone containing a cDNA molecule encoding human TANGO 268 (clone EpthEa11d1) was deposited with the American Type Culture Collection, 10801 University Boulevard, Manassas, Va., 20110-2209, on Mar. 30, 1999 as Accession Number 207180.

A clone containing a cDNA molecule encoding mouse TANGO 268 (clone EpTm268) was deposited with the American Type Culture Collection, 10801 University Boulevard, Manassas, Va., 20110-2209, on Jun. 14, 1999 as PTA-225.

EQUIVALENTS

Those skilled in the art will recognize, or be able to ascertain using no more than routine experimentation, many equivalents to the specific embodiments of the invention described herein. Such equivalents are intended to be encompassed by the following claims.

SEQUENCE LISTING

```
<160> NUMBER OF SEQ ID NOS: 24

<210> SEQ ID NO 1
<211> LENGTH: 2047
<212> TYPE: DNA
<213> ORGANISM: Homo sapiens

<400> SEQUENCE: 1
ggagtcgacc cacgcgtccg cagggctgag gaaccatgtc tccatccccg accgccctct        60
tctgtcttgg gctgtgtctg gggcgtgtgc cagcgcagag tggaccgctc cccaagccct       120
ccctccaggc tctgcccagc tccctggtgc ccctggagaa gccagtgacc ctccggtgcc       180
agggacctcc gggcgtggac ctgtaccgcc tggagaagct gagttccagc aggtaccagg       240
atcaggcagt cctcttcatc ccggccatga agagaagtct ggctggacgc taccgctgct       300
cctaccagaa cggaagcctc tggtccctgc ccagcgacca gctggagctc gttgccacgg       360 gagttttttgc caaaccctcg ctctcagccc agcccggccc ggcggtgtcg tcaggagggg       420
acgtaaccct acagtgtcag actcggtatg gctttgacca atttgctctg tacaaggaag       480
```

```
gggaccctgc gccctacaag aatcccgaga gatggtaccg ggctagtttc cccatcatca      540
cggtgaccgc cgcccacagc ggaacctacc gatgctacag cttctccagc agggacccat      600
acctgtggtc ggccccagc gaccccctgg agcttgtggt cacaggaacc tctgtgaccc       660
ccagccggtt accaacagaa ccaccttcct cggtagcaga attctcagaa gccaccgctg      720
aactgaccgt ctcattcaca aacaaagtct tcacaactga acttctagg agtatcacca       780
ccagtccaaa ggagtcagac tctccagctg gtcctgcccg ccagtactac accaagggca     840
acctggtccg gatatgcctc ggggctgtga tcctaataat cctggcgggg tttctggcag     900
aggactggca cagccggagg aagcgcctgc ggcacagggg cagggctgtg cagaggccgc     960
ttccgcccct gccgcccctc ccgcagaccc ggaaatcaca cggggtcag gatggaggcc     1020
gacaggatgt tcacagccgc gggttatgtt catgaccgct gaaccccagg cacggtcgta    1080
tccaagggag ggatcatggc atgggaggcg actcaaagac tggcgtgtgt ggagcgtgga    1140
agcaggaggc cagaggctac agctgtggaa acgaggccat gctgcctcct cctggtgttc    1200
catcagggag ccgttcggcc agtgtctgtc tgtctgtctg cctctctgtc tgagggcacc    1260
ctccatttgg gatggaagga atctgtggag accccatcct cctccctgca cactgtggat    1320
gacatggtac cctggctgga ccacatactg gcctcttcct tcaacctctc taatatgggc    1380
tccagacgga tctctaaggt tcccagctct caggggttgac tctgttccat cctctgtgca   1440
aaatcctcct gtgcttccct ttggccctct gtgctcttgt ctggttttcc ccagaaactc    1500
tcaccctcac tccatctccc actgcggtct aacaaatctc ctttcgtctc tcagaacggg    1560
tcttgcaggc agtttgggta tgtcattcat tttccttagt gtaaaactag cacgttgccc    1620
gcttcccttc acattagaaa acaagatcag cctgtgcaac atggtgaaac ctcatctcta    1680
ccaacaaaac aaaaaaacac aaaaattagc caggtgtggt ggtgcatccc tatactccca    1740
gcaactcggg gggctgaggt gggagaatgg cttgagcctg ggaggcagag gttgcagtga    1800
gctgagatca caccactgca ctctagctcg ggtgacgaag cctgaccttg tctcaaaaaa    1860
tacagggatg aatatgtcaa ttaccctgat ttgatcatag cacgttgtat acatgtactg    1920
caatattgct gtccaccca taaatatgta caattatgta tacatttta aaatcataaa      1980
aataagataa tgaaaaaaaa aaaaaaaaa aaaaaaggg cgggccgcta gactagtcta      2040
gagaaca                                                              2047

<210> SEQ ID NO 2
<211> LENGTH: 1017
<212> TYPE: DNA
<213> ORGANISM: Homo sapiens

<400> SEQUENCE: 2
atgtctccat ccccgaccgc cctcttctgt cttgggctgt gtctggggcg tgtgccagcg      60
cagagtggac cgctccccaa gccctccctc caggctctgc ccagctccct ggtgcccctg     120
gagaagccag tgaccctccg gtgccaggga cctccgggcg tggacctgta ccgcctggag     180
aagctgagtt ccagcaggta ccaggatcag gcagtcctct tcatcccggc catgaagaga     240
agtctggctg gacgctaccg ctgctcctac cagaacggaa gcctctggtc cctgcccagc     300
gaccagctgg agctcgttgc cacgggagtt tttgccaaac cctcgctctc agcccagccc     360
ggcccggcgg tgtcgtcagg aggggacgta accctacagt gtcagactcg gtatggcttt     420
gaccaatttg ctctgtacaa ggaagggac cctgcgccct acaagaatcc cgagagatgg     480
taccgggcta gttcccccat catcacggtg accgccgccc acagcggaac ctaccgatgc     540
```

-continued

```
tacagcttct ccagcaggga cccatacctg tggtcggccc ccagcgaccc cctggagctt      600
gtggtcacag gaacctctgt gaccccagc cggttaccaa cagaaccacc ttcctcggta       660
gcagaattct cagaagccac cgctgaactg accgtctcat tcacaaacaa agtcttcaca      720
actgagactt ctaggagtat caccaccagt ccaaaggagt cagactctcc agctggtcct      780
gcccgccagt actacaccaa gggcaacctg gtccggatat gcctcggggc tgtgatccta     840
ataatcctgg cggggtttct ggcagaggac tggcacagcc ggaggaagcg cctgcggcac      900
aggggcaggg ctgtgcagag gccgcttccg cccctgccgc ccctcccgca gacccggaaa      960
tcacacgggg gtcaggatgg aggccgacag gatgttcaca gccgcgggtt atgttca       1017
```

<210> SEQ ID NO 3
<211> LENGTH: 339
<212> TYPE: PRT
<213> ORGANISM: Homo sapiens

<400> SEQUENCE: 3

```
Met Ser Pro Ser Pro Thr Ala Leu Phe Cys Leu Gly Leu Cys Leu Gly
  1               5                  10                  15

Arg Val Pro Ala Gln Ser Gly Pro Leu Pro Lys Pro Ser Leu Gln Ala
             20                  25                  30

Leu Pro Ser Ser Leu Val Pro Leu Glu Lys Pro Val Thr Leu Arg Cys
         35                  40                  45

Gln Gly Pro Pro Gly Val Asp Leu Tyr Arg Leu Glu Lys Leu Ser Ser
     50                  55                  60

Ser Arg Tyr Gln Asp Gln Ala Val Leu Phe Ile Pro Ala Met Lys Arg
 65                  70                  75                  80

Ser Leu Ala Gly Arg Tyr Arg Cys Ser Tyr Gln Asn Gly Ser Leu Trp
                 85                  90                  95

Ser Leu Pro Ser Asp Gln Leu Glu Leu Val Ala Thr Gly Val Phe Ala
            100                 105                 110

Lys Pro Ser Leu Ser Ala Gln Pro Gly Pro Ala Val Ser Ser Gly Gly
        115                 120                 125

Asp Val Thr Leu Gln Cys Gln Thr Arg Tyr Gly Phe Asp Gln Phe Ala
    130                 135                 140

Leu Tyr Lys Glu Gly Asp Pro Ala Pro Tyr Lys Asn Pro Glu Arg Trp
145                 150                 155                 160

Tyr Arg Ala Ser Phe Pro Ile Ile Thr Val Thr Ala Ala His Ser Gly
                165                 170                 175

Thr Tyr Arg Cys Tyr Ser Phe Ser Ser Arg Asp Pro Tyr Leu Trp Ser
            180                 185                 190

Ala Pro Ser Asp Pro Leu Glu Leu Val Val Thr Gly Thr Ser Val Thr
        195                 200                 205

Pro Ser Arg Leu Pro Thr Glu Pro Pro Ser Ser Val Ala Glu Phe Ser
    210                 215                 220

Glu Ala Thr Ala Glu Leu Thr Val Ser Phe Thr Asn Lys Val Phe Thr
225                 230                 235                 240

Thr Glu Thr Ser Arg Ser Ile Thr Thr Ser Pro Lys Glu Ser Asp Ser
                245                 250                 255

Pro Ala Gly Pro Ala Arg Gln Tyr Tyr Thr Lys Gly Asn Leu Val Arg
            260                 265                 270

Ile Cys Leu Gly Ala Val Ile Leu Ile Ile Leu Ala Gly Phe Leu Ala
        275                 280                 285

Glu Asp Trp His Ser Arg Arg Lys Arg Leu Arg His Arg Gly Arg Ala
    290                 295                 300
```

```
Val Gln Arg Pro Leu Pro Pro Leu Pro Pro Leu Pro Gln Thr Arg Lys
305                 310                 315                 320

Ser His Gly Gly Gln Asp Gly Arg Gln Asp Val His Ser Arg Gly
            325                 330                 335

Leu Cys Ser

<210> SEQ ID NO 4
<211> LENGTH: 20
<212> TYPE: PRT
<213> ORGANISM: Homo sapiens

<400> SEQUENCE: 4

Met Ser Pro Ser Pro Thr Ala Leu Phe Cys Leu Gly Leu Cys Leu Gly
1               5                   10                  15

Arg Val Pro Ala
            20

<210> SEQ ID NO 5
<211> LENGTH: 319
<212> TYPE: PRT
<213> ORGANISM: Homo sapiens

<400> SEQUENCE: 5

Gln Ser Gly Pro Leu Pro Lys Pro Ser Leu Gln Ala Leu Pro Ser Ser
1               5                   10                  15

Leu Val Pro Leu Glu Lys Pro Val Thr Leu Arg Cys Gln Gly Pro Pro
                20                  25                  30

Gly Val Asp Leu Tyr Arg Leu Glu Lys Leu Ser Ser Ser Arg Tyr Gln
            35                  40                  45

Asp Gln Ala Val Leu Phe Ile Pro Ala Met Lys Arg Ser Leu Ala Gly
    50                  55                  60

Arg Tyr Arg Cys Ser Tyr Gln Asn Gly Ser Leu Trp Ser Leu Pro Ser
65                  70                  75                  80

Asp Gln Leu Glu Leu Val Ala Thr Gly Val Phe Ala Lys Pro Ser Leu
                85                  90                  95

Ser Ala Gln Pro Gly Pro Ala Val Ser Ser Gly Gly Asp Val Thr Leu
            100                 105                 110

Gln Cys Gln Thr Arg Tyr Gly Phe Asp Gln Phe Ala Leu Tyr Lys Glu
        115                 120                 125

Gly Asp Pro Ala Pro Tyr Lys Asn Pro Glu Arg Trp Tyr Arg Ala Ser
    130                 135                 140

Phe Pro Ile Ile Thr Val Thr Ala Ala His Ser Gly Thr Tyr Arg Cys
145                 150                 155                 160

Tyr Ser Phe Ser Ser Arg Asp Pro Tyr Leu Trp Ser Ala Pro Ser Asp
                165                 170                 175

Pro Leu Glu Leu Val Val Thr Gly Thr Ser Val Thr Pro Ser Arg Leu
            180                 185                 190

Pro Thr Glu Pro Pro Ser Ser Val Ala Glu Phe Ser Glu Ala Thr Ala
        195                 200                 205

Glu Leu Thr Val Ser Phe Thr Asn Lys Val Phe Thr Thr Glu Thr Ser
    210                 215                 220

Arg Ser Ile Thr Thr Ser Pro Lys Glu Ser Asp Ser Pro Ala Gly Pro
225                 230                 235                 240

Ala Arg Gln Tyr Tyr Thr Lys Gly Asn Leu Val Arg Ile Cys Leu Gly
                245                 250                 255

Ala Val Ile Leu Ile Ile Leu Ala Gly Phe Leu Ala Glu Asp Trp His
```

```
                    260                 265                 270
Ser Arg Arg Lys Arg Leu Arg His Arg Gly Arg Ala Val Gln Arg Pro
        275                 280                 285
Leu Pro Pro Leu Pro Pro Leu Pro Gln Thr Arg Lys Ser His Gly Gly
        290                 295                 300
Gln Asp Gly Gly Arg Gln Asp Val His Ser Arg Gly Leu Cys Ser
305                 310                 315

<210> SEQ ID NO 6
<211> LENGTH: 41
<212> TYPE: PRT
<213> ORGANISM: Homo sapiens

<400> SEQUENCE: 6

Cys Gln Gly Pro Pro Gly Val Asp Leu Tyr Arg Leu Glu Lys Leu Ser
1               5                   10                  15

Ser Ser Arg Tyr Gln Asp Gln Ala Val Leu Phe Ile Pro Ala Met Lys
            20                  25                  30

Arg Ser Leu Ala Gly Arg Tyr Arg Cys
        35                  40

<210> SEQ ID NO 7
<211> LENGTH: 47
<212> TYPE: PRT
<213> ORGANISM: Homo sapiens

<400> SEQUENCE: 7

Cys Gln Thr Arg Tyr Gly Phe Asp Gln Phe Ala Leu Tyr Lys Glu Gly
1               5                   10                  15

Asp Pro Ala Pro Tyr Lys Asn Pro Glu Arg Trp Tyr Arg Ala Ser Phe
            20                  25                  30

Pro Ile Ile Thr Val Thr Ala Ala His Ser Gly Thr Tyr Arg Cys
        35                  40                  45

<210> SEQ ID NO 8
<211> LENGTH: 19
<212> TYPE: PRT
<213> ORGANISM: Homo sapiens

<400> SEQUENCE: 8

Leu Val Arg Ile Cys Leu Gly Ala Val Ile Leu Ile Ile Leu Ala Gly
1               5                   10                  15

Phe Leu Ala

<210> SEQ ID NO 9
<211> LENGTH: 249
<212> TYPE: PRT
<213> ORGANISM: Homo sapiens

<400> SEQUENCE: 9

Gln Ser Gly Pro Leu Pro Lys Pro Ser Leu Gln Ala Leu Pro Ser Ser
1               5                   10                  15

Leu Val Pro Leu Glu Lys Pro Val Thr Leu Arg Cys Gln Gly Pro Pro
            20                  25                  30

Gly Val Asp Leu Tyr Arg Leu Glu Lys Leu Ser Ser Ser Arg Tyr Gln
        35                  40                  45

Asp Gln Ala Val Leu Phe Ile Pro Ala Met Lys Arg Ser Leu Ala Gly
    50                  55                  60

Arg Tyr Arg Cys Ser Tyr Gln Asn Gly Ser Leu Trp Ser Leu Pro Ser
65                  70                  75                  80
```

Asp Gln Leu Glu Leu Val Ala Thr Gly Val Phe Ala Lys Pro Ser Leu
                85                  90                  95

Ser Ala Gln Pro Gly Pro Ala Val Ser Ser Gly Gly Asp Val Thr Leu
            100                 105                 110

Gln Cys Gln Thr Arg Tyr Gly Phe Asp Gln Phe Ala Leu Tyr Lys Glu
        115                 120                 125

Gly Asp Pro Ala Pro Tyr Lys Asn Pro Glu Arg Trp Tyr Arg Ala Ser
    130                 135                 140

Phe Pro Ile Ile Thr Val Thr Ala Ala His Ser Gly Thr Tyr Arg Cys
145                 150                 155                 160

Tyr Ser Phe Ser Ser Arg Asp Pro Tyr Leu Trp Ala Pro Ser Asp
                165                 170                 175

Pro Leu Glu Leu Val Val Thr Gly Thr Ser Val Thr Pro Ser Arg Leu
            180                 185                 190

Pro Thr Glu Pro Pro Ser Ser Val Ala Glu Phe Ser Glu Ala Thr Ala
        195                 200                 205

Glu Leu Thr Val Ser Phe Thr Asn Lys Val Phe Thr Thr Glu Thr Ser
    210                 215                 220

Arg Ser Ile Thr Thr Ser Pro Lys Glu Ser Asp Ser Pro Ala Gly Pro
225                 230                 235                 240

Ala Arg Gln Tyr Tyr Thr Lys Gly Asn
                245

<210> SEQ ID NO 10
<211> LENGTH: 51
<212> TYPE: PRT
<213> ORGANISM: Homo sapiens

<400> SEQUENCE: 10

Glu Asp Trp His Ser Arg Arg Lys Arg Leu Arg His Arg Gly Arg Ala
1               5                   10                  15

Val Gln Arg Pro Leu Pro Pro Leu Pro Pro Leu Pro Gln Thr Arg Lys
                20                  25                  30

Ser His Gly Gly Gln Asp Gly Arg Gln Asp Val His Ser Arg Gly
            35                  40                  45

Leu Cys Ser
    50

<210> SEQ ID NO 11
<211> LENGTH: 2170
<212> TYPE: DNA
<213> ORGANISM: Homo sapiens

<400> SEQUENCE: 11
ctgagggctc atccctctgc agagcgcggg gtcaccggga ggagacgcca tgacgcccgc      60
cctcacagcc ctgctctgcc ttgggctgag tctgggcccc aggacccgcg tgcaggcagg     120
gcccttcccc aaacccaccc tctgggctga gccaggctct gtgatcagct gggggagccc     180
cgtgaccatc tggtgtcagg ggagcctgga ggcccaggag taccgactgg ataaagaggg     240
aagcccagag cccttggaca gaaataaccc actggaaccc aagaacaagg ccagattctc     300
catcccatcc atgacagagc accatgcggg gagataccgc tgccactatt acagctctgc     360
aggctggtca gagcccagcg acccctgga gctggtgatg acaggattct acaacaaacc     420
caccctctca gccctgccca gcctgtggt ggctcagggg gggaatatga ccctccgatg     480
tggctcacag aagggatatc accattttgt tctgatgaag gaaggagaac accagctccc     540

```
ccggaccctg gactcacagc agctccacag tgggggttc caggccctgt ccctgtggg      600
ccccgtgaac cccagccaca ggtggaggtt cacatgctat tactattata tgaacacccc    660
ccaggtgtgg tcccacccca gtgaccccct ggagattctg ccctcaggcg tgtctaggaa    720
gccctccctc ctgaccctgc agggcccgt cctggcccct gggcagagcc tgaccctcca    780
gtgtggctct gatgtcggct acgacagatt tgttctgtat aaggagggg aacgtgactt     840
cctccagcgc cctggccagc agcccaggc tgggctctcc caggccaact tcaccctggg    900
ccctgtgagc cctcccacg ggggccagta caggtgctat ggtgcacaca acctctcctc    960
cgagtggtcg gcccccagcg accccctgaa catcctgatg caggacaga tctatgacac   1020
cgtctccctg tcagcacagc cgggcccac agtggcctca ggagagaacg tgaccctgct    1080
gtgtcagtca tggtggcagt ttgacacttt ccttctgacc aaagaagggg cagcccatcc    1140
cccactgcgt ctgagatcaa tgtacggagc tcataagtac caggctgaat tccccatgag    1200
tcctgtgacc tcagcccacg cggggaccta caggtgctac ggctcataca gctccaaccc    1260
ccacctgctg tcttccccca gtgagcccct ggaactcatg gtctcaggac actctggagg    1320
ctccagcctc ccacccacag gccgccctc cacacctggt ctgggaagat acctggaggt    1380
tttgattggg gtctcggtgg ccttcgtcct gctgctcttc ctcctcctct tcctcctcct    1440
ccgacgtcag cgtcacagca aacacaggac atctgaccag agaaagactg atttccagcg   1500
tcctgcaggg gctgcggaga cagagcccaa ggacaggggc ctgctgagga ggtccagccc    1560
agctgctgac gtccaggaag aaaacctcta tgctgccgtg aaggacacac agtctgagga    1620
cagggtggag ctggacagtc agagcccaca cgatgaagac ccccaggcag tgacgtatgc    1680
cccggtgaaa cactccagtc ctaggagaga aatggcctct cctcccctcct cactgtctgg    1740
ggaattcctg gacacaaagg acagacaggt ggaagaggac aggcagatgg acactgaggc    1800
tgctgcatct gaagcctccc aggatgtgac ctacgcccag ctgcacagct tgacccttag    1860
acggaaggca actgagcctc ctccatccca ggaaggggaa cctccagctg agcccagcat    1920
ctacgccact ctggccatcc actagcccgg ggggtacgca gaccccacac tcagcagaag    1980
gagactcagg actgctgaag gcacgggagc tgccccagt ggacaccagt gaaccccagt     2040
cagcctggac ccctaacaca gaccatgagg agacgctggg aacttgtggg actcacctga    2100
ctcaaagatg actaatatcg tcccattttg gaataaagc aacagacttc tcaacaatca    2160
atgagttaat                                                        2170

<210> SEQ ID NO 12
<211> LENGTH: 631
<212> TYPE: PRT
<213> ORGANISM: Homo sapiens

<400> SEQUENCE: 12

Met Thr Pro Ala Leu Thr Ala Leu Leu Cys Leu Gly Leu Ser Leu Gly
  1               5                  10                  15

Pro Arg Thr Arg Val Gln Ala Gly Pro Phe Pro Lys Pro Thr Leu Trp
                 20                  25                  30

Ala Glu Pro Gly Ser Val Ile Ser Trp Gly Ser Pro Val Thr Ile Trp
             35                  40                  45

Cys Gln Gly Ser Leu Glu Ala Gln Glu Tyr Arg Leu Asp Lys Glu Gly
         50                  55                  60

Ser Pro Glu Pro Leu Asp Arg Asn Asn Pro Leu Glu Pro Lys Asn Lys
 65                  70                  75                  80

Ala Arg Phe Ser Ile Pro Ser Met Thr Glu His His Ala Gly Arg Tyr
```

-continued

```
                85                  90                  95
Arg Cys His Tyr Tyr Ser Ser Ala Gly Trp Ser Glu Pro Ser Asp Pro
            100                 105                 110

Leu Glu Leu Val Met Thr Gly Phe Tyr Asn Lys Pro Thr Leu Ser Ala
            115                 120                 125

Leu Pro Ser Pro Val Val Ala Ser Gly Gly Asn Met Thr Leu Arg Cys
            130                 135                 140

Gly Ser Gln Lys Gly Tyr His His Phe Val Leu Met Lys Glu Gly Glu
145                 150                 155                 160

His Gln Leu Pro Arg Thr Leu Asp Ser Gln Gln Leu His Ser Gly Gly
                165                 170                 175

Phe Gln Ala Leu Phe Pro Val Gly Pro Val Asn Pro Ser His Arg Trp
            180                 185                 190

Arg Phe Thr Cys Tyr Tyr Tyr Met Asn Thr Pro Gln Val Trp Ser
            195                 200                 205

His Pro Ser Asp Pro Leu Glu Ile Leu Pro Ser Gly Val Ser Arg Lys
            210                 215                 220

Pro Ser Leu Leu Thr Leu Gln Gly Pro Val Leu Ala Pro Gly Gln Ser
225                 230                 235                 240

Leu Thr Leu Gln Cys Gly Ser Asp Val Gly Tyr Asp Arg Phe Val Leu
                245                 250                 255

Tyr Lys Glu Gly Glu Arg Asp Phe Leu Gln Arg Pro Gly Gln Gln Pro
            260                 265                 270

Gln Ala Gly Leu Ser Gln Ala Asn Phe Thr Leu Gly Pro Val Ser Pro
            275                 280                 285

Ser His Gly Gly Gln Tyr Arg Cys Tyr Gly Ala His Asn Leu Ser Ser
            290                 295                 300

Glu Trp Ser Ala Pro Ser Asp Pro Leu Asn Ile Leu Met Ala Gly Gln
305                 310                 315                 320

Ile Tyr Asp Thr Val Ser Leu Ser Ala Gln Pro Gly Pro Thr Val Ala
                325                 330                 335

Ser Gly Glu Asn Val Thr Leu Leu Cys Gln Ser Trp Trp Gln Phe Asp
            340                 345                 350

Thr Phe Leu Leu Thr Lys Glu Gly Ala Ala His Pro Pro Leu Arg Leu
            355                 360                 365

Arg Ser Met Tyr Gly Ala His Lys Tyr Gln Ala Glu Phe Pro Met Ser
            370                 375                 380

Pro Val Thr Ser Ala His Ala Gly Thr Tyr Arg Cys Tyr Gly Ser Tyr
385                 390                 395                 400

Ser Ser Asn Pro His Leu Leu Ser Phe Pro Ser Glu Pro Leu Glu Leu
                405                 410                 415

Met Val Ser Gly His Ser Gly Ser Ser Leu Pro Pro Thr Gly Pro
            420                 425                 430

Pro Ser Thr Pro Gly Leu Gly Arg Tyr Leu Glu Val Leu Ile Gly Val
            435                 440                 445

Ser Val Ala Phe Val Leu Leu Leu Phe Leu Leu Leu Phe Leu Leu Leu
            450                 455                 460

Arg Arg Gln Arg His Ser Lys His Arg Thr Ser Asp Gln Arg Lys Thr
465                 470                 475                 480

Asp Phe Gln Arg Pro Ala Gly Ala Ala Glu Thr Glu Pro Lys Asp Arg
                485                 490                 495

Gly Leu Leu Arg Arg Ser Ser Pro Ala Ala Asp Val Gln Glu Glu Asn
            500                 505                 510
```

```
Leu Tyr Ala Ala Val Lys Asp Thr Gln Ser Glu Asp Arg Val Glu Leu
        515                 520                 525

Asp Ser Gln Ser Pro His Asp Glu Asp Pro Gln Ala Val Thr Tyr Ala
530                 535                 540

Pro Val Lys His Ser Ser Pro Arg Arg Glu Met Ala Ser Pro Pro Ser
545                 550                 555                 560

Ser Leu Ser Gly Glu Phe Leu Asp Thr Lys Asp Arg Gln Val Glu Glu
                565                 570                 575

Asp Arg Gln Met Asp Thr Glu Ala Ala Ala Ser Glu Ala Ser Gln Asp
            580                 585                 590

Val Thr Tyr Ala Gln Leu His Ser Leu Thr Leu Arg Arg Lys Ala Thr
        595                 600                 605

Glu Pro Pro Pro Ser Gln Glu Gly Pro Pro Ala Glu Pro Ser Ile
    610                 615                 620

Tyr Ala Thr Leu Ala Ile His
625                 630

<210> SEQ ID NO 13
<211> LENGTH: 50
<212> TYPE: PRT
<213> ORGANISM: Homo sapiens

<400> SEQUENCE: 13

Gly Gln Ser Val Ile Leu Arg Cys Gln Gly Pro Pro Asp Val Asp Leu
1               5                   10                  15

Tyr Arg Leu Glu Lys Leu Lys Pro Glu Lys Tyr Glu Ala Gln Asp Phe
            20                  25                  30

Leu Phe Ile Pro Thr Met Glu Arg Ser Asn Ala Gly Arg Tyr Arg Cys
        35                  40                  45

Ser Tyr
    50

<210> SEQ ID NO 14
<211> LENGTH: 1163
<212> TYPE: DNA
<213> ORGANISM: Mus musculus

<400> SEQUENCE: 14
gagtcgaccc acgcgtccgc ttccctgctt ggccacatag ctcaggactg ggttgcagaa      60
ccatgtctcc agcctcaccc actttcttct gtattgggct gtgtgtactg caagtgatcc     120
aaacacagag tggcccactc cccaagcctt ccctccaggc tcagcccagt tccctggtac     180
ccctgggtca gtcagttatt ctgaggtgcc agggacctcc agatgtggat ttatatcgcc     240
tggagaaact gaaaccggag aagtatgaag atcaagactt tctcttcatt ccaaccatgg     300
aaagaagtaa tgctggacgg tatcgatgct cttatcagaa tgggagtcac tggtctctcc     360
caagtgacca gcttgagcta attgctacag gtgtgtatgc taaaccctca ctctcagctc     420
atcccagctc agcagtccct caaggcaggg atgtgactct gaagtgccag agcccataca     480
gttttgatga attcgttcta tacaaagaag gggatactgg gccttataag agacctgaga     540
aatggtaccg ggccaatttc cccatcatca cagtgactgc tgctcacagt gggacgtacc     600
ggtgttacag cttctccagc tcatctccat acctgtggtc agccccgagt gaccctctag     660
tgcttgtggt tactggactc tctgccactc ccagccaggt acccacggaa gaatcatttc     720
ctgtgacaga atcctccagg agaccttcca tcttacccac aaacaaaata tctacaactg     780
aaaagcctat gaatatcact gcctctccag aggggctgag ccctccaatt ggttttgctc     840
```

```
atcagcacta tgccaagggg aatctggtcc ggatatgcct tggtgccacg attataataa      900
ttttgttggg gcttctagca gaggattggc acagtcggaa gaaatgcctg caacacagga      960
tgagagcttt gcaaaggcca ctaccacccc tcccactggc ctagaaataa cttggctttc     1020
agcagaggga ttgaccagac atccatgcac aaccatggac atcaccacta gagccacaga     1080
catggacata ctcaagagtg gggaggttat ataaaaaaat gagtgtggag aataaatgca     1140
gagccaacaa ggtgaaaaaa aaa                                             1163

<210> SEQ ID NO 15
<211> LENGTH: 939
<212> TYPE: DNA
<213> ORGANISM: Mus musculus

<400> SEQUENCE: 15
atgtctccag cctcacccac tttcttctgt attgggctgt gtgtactgca agtgatccaa       60
acacagagtg gcccactccc caagccttcc ctccaggctc agcccagttc cctggtaccc      120
ctgggtcagt cagttattct gaggtgccag ggacctccag atgtggattt atatcgcctg      180
gagaaactga accggagaa gtatgaagat caagactttc tcttcattcc aaccatggaa      240
agaagtaatg ctggacggta tcgatgctct tatcagaatg ggagtcactg gtctctccca      300
agtgaccagc ttgagctaat tgctacaggt gtgtatgcta accctcact ctcagctcat      360 cccagctcag cagtccctca aggcagggat gtgactctga agtgccagag cccatacagt      420
tttgatgaat tcgttctata caagaaggg gatactgggc cttataagag acctgagaaa      480
tggtaccggg ccaatttccc catcatcaca gtgactgctg ctcacagtgg gacgtaccgg      540
tgttacagct tctccagctc atctccatac ctgtggtcag ccccgagtga ccctctagtg      600
cttgtggtta ctggactctc tgccactccc agccaggtac ccacggaaga atcatttcct      660
gtgacagaat cctccaggag accttccatc ttacccacaa acaaaatatc tacaactgaa      720
aagcctatga atatcactgc ctctccagag gggctgagcc ctccaattgg ttttgctcat      780
cagcactatg ccaaggggaa tctggtccgg atatgccttg gtgccacgat tataataatt      840
ttgttggggc ttctagcaga ggattggcac agtcggaaga aatgcctgca acacaggatg      900
agagctttgc aaaggccact accaccctc ccactggcc                              939

<210> SEQ ID NO 16
<211> LENGTH: 313
<212> TYPE: PRT
<213> ORGANISM: Mus musculus

<400> SEQUENCE: 16

Met Ser Pro Ala Ser Pro Thr Phe Phe Cys Ile Gly Leu Cys Val Leu
 1               5                  10                  15

Gln Val Ile Gln Thr Gln Ser Gly Pro Leu Pro Lys Pro Ser Leu Gln
                20                  25                  30

Ala Gln Pro Ser Ser Leu Val Pro Leu Gly Gln Ser Val Ile Leu Arg
            35                  40                  45

Cys Gln Gly Pro Pro Asp Val Asp Leu Tyr Arg Leu Glu Lys Leu Lys
        50                  55                  60

Pro Glu Lys Tyr Glu Asp Gln Asp Phe Leu Phe Ile Pro Thr Met Glu
65                  70                  75                  80

Arg Ser Asn Ala Gly Arg Tyr Arg Cys Ser Tyr Gln Asn Gly Ser His
                85                  90                  95

Trp Ser Leu Pro Ser Asp Gln Leu Glu Leu Ile Ala Thr Gly Val Tyr
               100                 105                 110
```

```
Ala Lys Pro Ser Leu Ser Ala His Pro Ser Ser Ala Val Pro Gln Gly
            115                 120                 125

Arg Asp Val Thr Leu Lys Cys Gln Ser Pro Tyr Ser Phe Asp Glu Phe
        130                 135                 140

Val Leu Tyr Lys Glu Gly Asp Thr Gly Pro Tyr Lys Arg Pro Glu Lys
145                 150                 155                 160

Trp Tyr Arg Ala Asn Phe Pro Ile Ile Thr Val Thr Ala Ala His Ser
                165                 170                 175

Gly Thr Tyr Arg Cys Tyr Ser Phe Ser Ser Ser Pro Tyr Leu Trp
            180                 185                 190

Ser Ala Pro Ser Asp Pro Leu Val Leu Val Thr Gly Leu Ser Ala
        195                 200                 205

Thr Pro Ser Gln Val Pro Thr Glu Glu Ser Phe Pro Val Thr Glu Ser
        210                 215                 220

Ser Arg Arg Pro Ser Ile Leu Pro Thr Asn Lys Ile Ser Thr Thr Glu
225                 230                 235                 240

Lys Pro Met Asn Ile Thr Ala Ser Pro Glu Gly Leu Ser Pro Pro Ile
                245                 250                 255

Gly Phe Ala His Gln His Tyr Ala Lys Gly Asn Leu Val Arg Ile Cys
                260                 265                 270

Leu Gly Ala Thr Ile Ile Ile Leu Leu Gly Leu Leu Ala Glu Asp
            275                 280                 285

Trp His Ser Arg Lys Lys Cys Leu Gln His Arg Met Arg Ala Leu Gln
            290                 295                 300

Arg Pro Leu Pro Pro Leu Pro Leu Ala
305                 310

<210> SEQ ID NO 17
<211> LENGTH: 21
<212> TYPE: PRT
<213> ORGANISM: Mus musculus

<400> SEQUENCE: 17

Met Ser Pro Ala Ser Pro Thr Phe Phe Cys Ile Gly Leu Cys Val Leu
1               5                   10                  15

Gln Val Ile Gln Thr
            20

<210> SEQ ID NO 18
<211> LENGTH: 292
<212> TYPE: PRT
<213> ORGANISM: Mus musculus

<400> SEQUENCE: 18

Gln Ser Gly Pro Leu Pro Lys Pro Ser Leu Gln Ala Gln Pro Ser Ser
1               5                   10                  15

Leu Val Pro Leu Gly Gln Ser Val Ile Leu Arg Cys Gln Gly Pro Pro
            20                  25                  30

Asp Val Asp Leu Tyr Arg Leu Glu Lys Leu Lys Pro Glu Lys Tyr Glu
        35                  40                  45

Asp Gln Asp Phe Leu Phe Ile Pro Thr Met Glu Arg Ser Asn Ala Gly
    50                  55                  60

Arg Tyr Arg Cys Ser Tyr Gln Asn Gly Ser His Trp Ser Leu Pro Ser
65                  70                  75                  80

Asp Gln Leu Glu Leu Ile Ala Thr Gly Val Tyr Ala Lys Pro Ser Leu
                85                  90                  95
```

```
Ser Ala His Pro Ser Ser Ala Val Pro Gln Gly Arg Asp Val Thr Leu
            100                 105                 110

Lys Cys Gln Ser Pro Tyr Ser Phe Asp Glu Phe Val Leu Tyr Lys Glu
            115                 120                 125

Gly Asp Thr Gly Pro Tyr Lys Arg Pro Glu Lys Trp Tyr Arg Ala Asn
130                 135                 140

Phe Pro Ile Ile Thr Val Thr Ala Ala His Ser Gly Thr Tyr Arg Cys
145                 150                 155                 160

Tyr Ser Phe Ser Ser Ser Pro Tyr Leu Trp Ser Ala Pro Ser Asp
            165                 170                 175

Pro Leu Val Leu Val Thr Gly Leu Ser Ala Thr Pro Ser Gln Val
            180                 185                 190

Pro Thr Glu Glu Ser Phe Pro Val Thr Glu Ser Ser Arg Arg Pro Ser
            195                 200                 205

Ile Leu Pro Thr Asn Lys Ile Ser Thr Thr Glu Lys Pro Met Asn Ile
            210                 215                 220

Thr Ala Ser Pro Glu Gly Leu Ser Pro Pro Ile Gly Phe Ala His Gln
225                 230                 235                 240

His Tyr Ala Lys Gly Asn Leu Val Arg Ile Cys Leu Gly Ala Thr Ile
            245                 250                 255

Ile Ile Ile Leu Leu Gly Leu Leu Ala Glu Asp Trp His Ser Arg Lys
            260                 265                 270

Lys Cys Leu Gln His Arg Met Arg Ala Leu Gln Arg Pro Leu Pro Pro
            275                 280                 285

Leu Pro Leu Ala
            290

<210> SEQ ID NO 19
<211> LENGTH: 267
<212> TYPE: PRT
<213> ORGANISM: Mus musculus

<400> SEQUENCE: 19

Met Ser Pro Ala Ser Pro Thr Phe Phe Cys Ile Gly Leu Cys Val Leu
1               5                   10                  15

Gln Val Ile Gln Thr Gln Ser Gly Pro Leu Pro Lys Pro Ser Leu Gln
            20                  25                  30

Ala Gln Pro Ser Ser Leu Val Pro Leu Gly Gln Ser Val Ile Leu Arg
            35                  40                  45

Cys Gln Gly Pro Pro Asp Val Asp Leu Tyr Arg Leu Glu Lys Leu Lys
            50                  55                  60

Pro Glu Lys Tyr Glu Asp Gln Asp Phe Leu Phe Ile Pro Thr Met Glu
65                  70                  75                  80

Arg Ser Asn Ala Gly Arg Tyr Arg Cys Ser Tyr Gln Asn Gly Ser His
            85                  90                  95

Trp Ser Leu Pro Ser Asp Gln Leu Glu Leu Ile Ala Thr Gly Val Tyr
            100                 105                 110

Ala Lys Pro Ser Leu Ser Ala His Pro Ser Ser Ala Val Pro Gln Gly
            115                 120                 125

Arg Asp Val Thr Leu Lys Cys Gln Ser Pro Tyr Ser Phe Asp Glu Phe
130                 135                 140

Val Leu Tyr Lys Glu Gly Asp Thr Gly Pro Tyr Lys Arg Pro Glu Lys
145                 150                 155                 160

Trp Tyr Arg Ala Asn Phe Pro Ile Ile Thr Val Thr Ala Ala His Ser
            165                 170                 175
```

```
Gly Thr Tyr Arg Cys Tyr Ser Phe Ser Ser Ser Pro Tyr Leu Trp
            180                 185                 190

Ser Ala Pro Ser Asp Pro Leu Val Leu Val Thr Gly Leu Ser Ala
        195                 200                 205

Thr Pro Ser Gln Val Pro Thr Glu Glu Ser Phe Pro Val Thr Glu Ser
210                 215                 220

Ser Arg Arg Pro Ser Ile Leu Pro Thr Asn Lys Ile Ser Thr Glu
225                 230                 235                 240

Lys Pro Met Asn Ile Thr Ala Ser Pro Glu Gly Leu Ser Pro Pro Ile
                245                 250                 255

Gly Phe Ala His Gln His Tyr Ala Lys Gly Asn
            260                 265
```

<210> SEQ ID NO 20
<211> LENGTH: 19
<212> TYPE: PRT
<213> ORGANISM: Mus musculus

<400> SEQUENCE: 20

```
Leu Val Arg Ile Cys Leu Gly Ala Thr Ile Ile Ile Leu Leu Gly
1               5                   10                  15

Leu Leu Ala
```

<210> SEQ ID NO 21
<211> LENGTH: 27
<212> TYPE: PRT
<213> ORGANISM: Mus musculus

<400> SEQUENCE: 21

```
Glu Asp Trp His Ser Arg Lys Lys Cys Leu Gln His Arg Met Arg Ala
1               5                   10                  15

Leu Gln Arg Pro Leu Pro Pro Leu Pro Leu Ala
            20                  25
```

<210> SEQ ID NO 22
<211> LENGTH: 41
<212> TYPE: PRT
<213> ORGANISM: Mus musculus

<400> SEQUENCE: 22

```
Cys Gln Gly Pro Pro Asp Val Asp Leu Tyr Arg Leu Glu Lys Leu Lys
1               5                   10                  15

Pro Glu Lys Tyr Glu Asp Gln Asp Phe Leu Phe Ile Pro Thr Met Glu
            20                  25                  30

Arg Ser Asn Ala Gly Arg Tyr Arg Cys
        35                  40
```

<210> SEQ ID NO 23
<211> LENGTH: 47
<212> TYPE: PRT
<213> ORGANISM: Mus musculus

<400> SEQUENCE: 23

```
Cys Gln Ser Pro Tyr Ser Phe Asp Glu Phe Val Leu Tyr Lys Glu Gly
1               5                   10                  15

Asp Thr Gly Pro Tyr Lys Arg Pro Glu Lys Trp Tyr Arg Ala Asn Phe
            20                  25                  30

Pro Ile Ile Thr Val Thr Ala Ala His Ser Gly Thr Tyr Arg Cys
        35                  40                  45
```

<210> SEQ ID NO 24
<211> LENGTH: 1896
<212> TYPE: DNA
<213> ORGANISM: Homo sapiens

<400> SEQUENCE: 24

```
atgacgcccg ccctcacagc cctgctctgc cttgggctga gtctgggccc caggacccgc    60
gtgcaggcag ggcccttccc caaacccacc ctctgggctg agccaggctc tgtgatcagc   120
tgggggagcc ccgtgaccat ctggtgtcag gggagcctgg aggcccagga gtaccgactg   180
gataaagagg gaagcccaga gcccttggac agaaataacc cactggaacc caagaacaag   240
gccagattct ccatcccatc catgacagag caccatgcgg ggagataccg ctgccactat   300
tacagctctg caggctggtc agagcccagc gaccccctgg agctggtgat gacaggattc   360
tacaacaaac ccaccctctc agccctgccc agccctgtgg tggcctcagg ggggaatatg   420
accctccgat gtggctcaca gaagggatat caccattttg ttctgatgaa ggaaggagaa   480
caccagctcc cccggaccct ggactcacag cagctccaca gtgggggtt ccaggccctg   540
ttccctgtgg gccccgtgaa ccccagccac aggtggaggt tcacatgcta ttactattat   600
atgaacaccc cccaggtgtg gtcccacccc agtgaccccc tggagattct gccctcaggc   660
gtgtctagga agccctccct cctgaccctg cagggccctg tcctggcccc tgggcagagc   720
ctgacctcc agtgtggctc tgatgtcggc tacgacagat ttgttctgta taaggagggg   780
gaacgtgact tcctccagcg ccctggccag cagccccagg ctgggctctc ccaggccaac   840
ttcaccctgg gcctgtgag ccctcccac ggggccagt acaggtgcta tggtgcacac   900
aacctctcct ccgagtggtc ggccccagc gacccctga acatcctgat ggcaggacag   960
atctatgaca ccgtctccct gtcagcacag ccggccca cagtggcctc aggagagaac  1020
gtgaccctgc tgtgtcagtc atggtggcag tttgacactt tccttctgac caaagaaggg  1080
gcagcccatc ccccactgcg tctgagatca atgtacggag ctcataagta ccaggctgaa  1140
ttccccatga gtcctgtgac ctcagcccac gcggggacct acaggtgcta cggctcatac  1200
agctccaacc cccacctgct gtctttcccc agtgagcccc tggaactcat ggtctcagga  1260
cactctggag gctccagcct cccacccaca gggccgccct ccacacctgg tctgggaaga  1320
tacctggagg ttttgattgg ggtctcggtg gccttcgtcc tgctgctctt cctcctcctc  1380
ttcctcctcc tccgacgtca gcgtcacagc aaacacagga catctgacca gagaaagact  1440
gatttccagc gtcctgcagg ggctgcggag acagagccca aggacagggg cctgctgagg  1500
aggtccagcc cagctgctga cgtccaggaa gaaaacctct atgctgccgt gaaggacaca  1560
cagtctgagg acagggtgga gctggacagt cagagcccac acgatgaaga cccccaggca  1620
gtgacgtatg ccccggtgaa acactccagt cctaggagag aaatggcctc tcctccctcc  1680
tcactgtctg gggaattcct ggacacaaag gacagacagg tggaagagga caggcagatg  1740
gacactgagg ctgctgcatc tgaagcctcc caggatgtga cctacgccca gctgcacagc  1800
ttgacccta gacggaaggc aactgagcct cctccatccc aggaagggga acctccagct  1860
gagcccagca tctacgccac tctggccatc cactag                             1896
```

What is claimed is:

1. A method of detecting a TANGO268 polypeptide, comprising the step of: contacting a sample with an antibody or antigen binding fragment thereof that binds to an amino acid sequence selected from the group consisting of SEQ ID NO:3, SEQ ID NO:16, and the amino acid sequence encoded by the cDNA insert of the plasmid deposited with ATCC as Accession Number 207180; wherein said antibody or binding fragment thereof specifically binds to an extracellular domain of said TANGO268 polypeptide.

2. The method of claim 1, wherein the antibody or binding fragment thereof is selected from the group consisting of:
   a) an antibody or binding fragment thereof which specifically binds to the extracellular domain comprising amino acid residues 21 to 269 of SEQ ID NO:3 or amino acid residues 21 to 269 of the amino acid sequence encoded by the cDNA insert of the plasmid deposited with ATCC as Accession Number 207180; and
b) an antibody or binding fragment thereof which specifically binds to the extracellular domain of the amino acid sequence of SEQ ID NO:3, or the extracellular domain of the amino acid sequence encoded by the cDNA insert of the plasmid deposited with ATCC as Accession Number 207180.

3. The method of claim 2, wherein the antibody or binding fragment thereof is selected from the group consisting of:
a) a monoclonal antibody or binding fragment thereof;
b) a polyclonal antibody or binding fragment thereof; and
c) a chimeric antibody or binding fragment thereof.

4. The method of claim 2, wherein the antibody or binding fragment thereof is a humanized antibody or binding fragment thereof.

5. The method of claim 2, wherein the antibody or binding fragment thereof is a human antibody or binding fragment thereof.

6. The method of claim 2, wherein the antigen binding fragment thereof is selected from the group consisting of:
a) a Fab fragment; and
b) a F(ab')$_2$ fragment.

7. The method of claim 2, wherein the antibody or binding fragment thereof is conjugated to a detectable substance.

8. The method of claim 7, wherein the detectable substance is an enzyme, a prosthetic group, a fluorescent material, a luminescent material, a bioluminescent material, or a radioactive material.

9. The method of claim 1, wherein the extracellular domain consists of amino acid residues 21 to 269 of SEQ ID NO:3.

10. The method of claim 1, wherein the extracellular domain comprises an immunoglobulin-like domain comprising amino acid residues 48 to 88 or 134 to 180 of SEQ ID NO:3.

11. The method of claim 10, wherein the immunoglobulin-like domain consists of amino acid residues 48 to 88 or 134 to 180 of SEQ ID NO:3.

* * * * *